(12) United States Patent
Goshoo et al.

(10) Patent No.: US 8,198,071 B2
(45) Date of Patent: Jun. 12, 2012

(54) SUBSTRATE FOR BIOCHIP, BIOCHIP, METHOD FOR MANUFACTURING SUBSTRATE FOR BIOCHIP, AND METHOD FOR MANUFACTURING BIOCHIP

(75) Inventors: Yasuhiro Goshoo, Tokyo (JP); Takaaki Kuroiwa, Tokyo (JP); Naohiro Ishikawa, Tokyo (JP); Daisuke Obara, Tokyo (JP); Shinsuke Yamasaki, Tokyo (JP); Kazuko Sasaki, Tokyo (JP); Yasuko Horiguchi, Tokyo (JP)

(73) Assignee: Azbil Corporation, Tokyo (JP)

( * ) Notice: Subject to any disclaimer, the term of this patent is extended or adjusted under 35 U.S.C. 154(b) by 0 days.

(21) Appl. No.: 13/079,483

(22) Filed: Apr. 4, 2011

(65) Prior Publication Data

US 2011/0174773 A1    Jul. 21, 2011

Related U.S. Application Data

(62) Division of application No. 11/991,796, filed as application No. PCT/JP2006/317634 on Sep. 6, 2006, now abandoned.

(30) Foreign Application Priority Data

Sep. 16, 2005  (JP) .................................. 2005-270252
Sep. 26, 2005  (JP) .................................. 2005-277963

(51) Int. Cl.
   *C12M 1/00*     (2006.01)
   *C12M 1/36*     (2006.01)
   *C07H 21/04*    (2006.01)

(52) U.S. Cl. .................. 435/283.1; 435/174; 435/287.2; 422/68.1; 536/23.1

(58) Field of Classification Search .................... None
    See application file for complete search history.

(56) References Cited

U.S. PATENT DOCUMENTS

| 5,658,734 | A  |   | 8/1997  | Brock et al. |
| 5,874,219 | A  |   | 2/1999  | Rava et al. |
| 5,959,098 | A  | * | 9/1999  | Goldberg et al. ............ 536/25.3 |
| 6,359,125 | B1 | * | 3/2002  | Kim et al. .................... 536/23.1 |
| 6,476,215 | B1 |   | 11/2002 | Okamoto et al. |
| 6,500,587 | B1 |   | 12/2002 | Ghandehari et al. |
| 6,803,228 | B1 |   | 10/2004 | Caillat et al. |
| 6,852,524 | B2 |   | 2/2005  | Okamura et al. |
| 6,902,705 | B1 |   | 6/2005  | Caillat et al. |

(Continued)

FOREIGN PATENT DOCUMENTS

EP        1 245 278 A2    10/2002

(Continued)

OTHER PUBLICATIONS

Mutin, P.N., et al., "Selective Surface Modification of SiO2-TiO2 Supports with Phosphonic Acids", Chem. Mater., vol. 16, pp. 5670-5675, (2004).

(Continued)

*Primary Examiner* — Betty Forman
(74) *Attorney, Agent, or Firm* — The Nath Law Group; Jerald L. Meyer; Stanley N. Protigal

(57) ABSTRACT

A base plate having a surface on which a plurality of hydroxyl groups can be introduced, a metallic membrane disposed on the base plate and having a plurality of wells reaching the base plate, and a crosslinkable polymer membrane disposed on the metallic membrane are included.

14 Claims, 56 Drawing Sheets

U.S. PATENT DOCUMENTS

| | | | |
|---|---|---|---|
| 2002/0081588 A1 | 6/2002 | De Lumley-woodyear et al. | |
| 2002/0192600 A1 | 12/2002 | Okamura et al. | |
| 2002/0197568 A1 | 12/2002 | Neriishi et al. | |
| 2003/0082587 A1* | 5/2003 | Seul et al. | 435/6 |
| 2005/0019799 A1 | 1/2005 | Grasso et al. | |
| 2005/0121782 A1* | 6/2005 | Nakamura et al. | 257/730 |
| 2005/0158738 A1 | 7/2005 | Okamura et al. | |

FOREIGN PATENT DOCUMENTS

| | | |
|---|---|---|
| EP | 1 445 613 A2 | 8/2004 |
| EP | 1 614 460 A1 | 1/2006 |
| JP | 61-215947 A | 9/1986 |
| JP | 06-102182 A | 4/1994 |
| JP | 11-187900 A | 7/1999 |
| JP | 2001-337096 A | 12/2001 |
| JP | 2002-525573 A | 8/2002 |
| JP | 2002-532699 A | 10/2002 |
| JP | 2002-537869 A | 11/2002 |
| JP | 2002-350348 A | 12/2002 |
| JP | 2002-350447 A | 12/2002 |
| JP | 2003-014760 A | 1/2003 |
| JP | 2003-083974 A | 3/2003 |
| JP | 2003-156495 A | 5/2003 |
| JP | 2004-020280 A | 1/2004 |
| JP | 2004-045346 A | 2/2004 |
| JP | 2004-205340 A | 7/2004 |
| JP | 2005-025246 A | 1/2005 |
| JP | 2005-118049 A | 5/2005 |
| JP | 2005-156527 A | 6/2005 |
| JP | 2006-023301 A | 1/2006 |
| WO | 98/59243 A1 | 12/1998 |
| WO | 2006/060753 A2 | 6/2006 |

OTHER PUBLICATIONS

Official Action issued on Nov. 10, 2010, in counterpart European Patent Application No. 06 797 529.2 four (4) pages.

* cited by examiner

PROTECTED ADENINE

PROTECTED CYTOSINE

PROTECTED GUANINE

FIG. 25
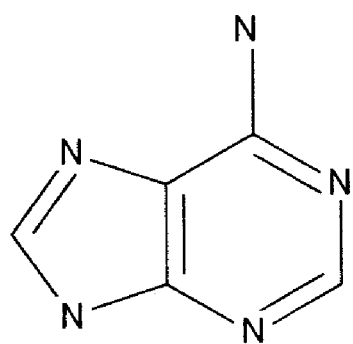
ADENINE
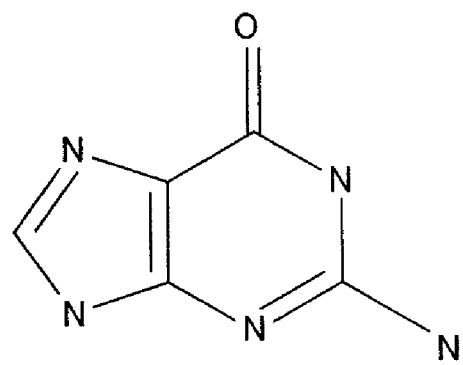
GUANINE
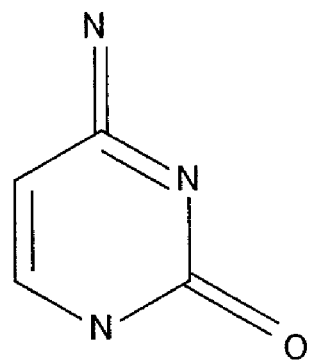
CYTOSINE

SUBSTRATE FOR BIOCHIP, BIOCHIP, METHOD FOR MANUFACTURING SUBSTRATE FOR BIOCHIP, AND METHOD FOR MANUFACTURING BIOCHIP

This is a Divisional Application of U.S. patent application Ser. No. 11/991,796, filed on Mar. 11, 2008, which is a National Phase Application filed under 35 USC 371 of International Application No. PCT/JP2006/317634, filed on Sep. 6, 2006, an application claiming foreign priority benefits under 35 USC 119 of Japanese Application No. 2005-270252, filed on Sep. 16, 2005, and claiming foreign priority benefits under 35 USC 119 of Japanese Application No. 2005-277963, filed on Sep. 26, 2005, the content of each of which is hereby incorporated by reference in its entirety.

TECHNICAL FIELD

This invention relates to a technique for detecting a biomolecule, especially to a substrate for a biochip, the biochip, a method for manufacturing the substrate for the biochip, and a method for manufacturing the biochip.

BACKGROUND ART

"Biochip" is the generic term for devices in which probe biomolecules that react with to-be-detected target biomolecules in a specific manner are fixed at predetermined positions on a chip surface. A deoxyribonucleic acid (DNA) chip that is atypical example of the biochip is used to detect the types and amounts of target DNA included in blood or cell extract. The DNA chip has, for example, a structure in which thousands to tens of thousands of types of probe DNA, each being single-chain DNA having a known sequence, are arranged in an array on a substrate such as a glass slide.

When a to-be-examined liquid containing fluorescence-marked target DNA is supplied to the DNA chip, only the target DNA which has sequences complementary to the sequences of the probe DNA is bonded to the probe DNA by hydrogen-bonding to form a complementary double chain. As a result, the parts to which the target DNA is fixed is fluorescent-colored. By measuring the position and coloring intensity of the fluorescent-colored parts on the chip, the types and amounts of the target DNA can be detected. Therefore, as described in a published Japanese translations of PCT international publication for patent applications 2002-537869, when the DNA chip is manufactured, the probe DNA having a predetermined sequence should be fixed only on a predetermined portion on a surface of the substrate. However, it is difficult to fix the probe DNA only in the specific location. Therefore, the target DNA bonded to the probe DNA fixed in location other than the specific location becomes background noise in a detection process. It becomes a factor to decrease a detection accuracy of the DNA chip.

DISCLOSURE OF INVENTION

By a first aspect of present invention, a substrate for a biochip comprising a base plate having a surface on which a plurality of hydroxyl groups can be introduced, a metallic membrane disposed on the base plate and having a plurality of wells reaching the base plate, and a crosslinkable polymer membrane disposed on the metallic membrane is provided.

By a second aspect of present invention, a biochip comprising a base plate, a metallic membrane disposed on the base plate and having a plurality of wells reaching the base plate, and a plurality of probe biomolecules bonded on a surface of the base plate exposed from the plurality of wells is provided.

By a third aspect of present invention, a method for manufacturing a substrate for a biochip including a step for preparing a base plate having a surface on which a plurality of hydroxyl groups can be introduced, a step for forming a metallic membrane on the base plate, a step for forming a crosslinkable polymer membrane on the metallic membrane, a step for selectively removing portions of the polymer membrane, and a step for delineating a plurality of wells reaching the base plate in the metallic membrane, by using the polymer membrane of which the portions were selectively removed as an etching mask is provided.

By a fourth aspect of present invention, a method for manufacturing a biochip including a step for preparing a base plate, a step for forming a metallic membrane on the base plate, a step for forming a crosslinkable polymer membrane on the metallic membrane, a step for selectively removing portions of the polymer membrane, a step for delineating a plurality of wells reaching the base plate in the metallic membrane, by using the polymer membrane of which the portions were selectively removed as an etching mask, a step for introducing a plurality of hydroxyl groups on a surface of the base plate exposed from the plurality of wells, a step for bonding a plurality of probe biomolecules to the plurality of hydroxyl groups, respectively, and a step for soaking the metallic membrane and the polymer membrane in an alkaline solution to peel off the polymer membrane from the metallic membrane is provided.

By a fifth aspect of present invention, a method for manufacturing a biochip including a step for preparing a substrate for the biochip comprising a base plate, a metallic membrane disposed on the base plate and having a plurality of wells reaching the base plate, a crosslinkable polymer membrane disposed on the metallic membrane, and a plurality of hydroxyl groups introduced on a surface of the base plate exposed from the plurality of wells, a step for bonding a plurality of probe biomolecules to the plurality of hydroxyl groups, respectively, and a step for soaking the metallic membrane and the polymer membrane in an alkaline solution to peel off the polymer membrane from the metallic membrane is provided.

By a sixth aspect of present invention, a substrate for a biochip comprising a base plate having a surface on which a plurality of hydroxyl groups can be introduced, and a cover member disposed on the base plate when probe biomolecules are bonded to the plurality of hydroxyl groups, respectively, the cover member having a plurality of through holes to define binding regions where the probe biomolecules are bonded to the surface of the base plate, is provided.

By a seventh aspect of present invention, a biochip comprising an optical transparency base plate, a light shielding film disposed on the base plate and having a plurality of through holes reaching the base plate, and a plurality of probe biomolecules bonded to the base plate exposed from each of the plurality of through holes is provided.

By an eighth aspect of present invention, a biochip comprising an optical transparency base plate, a light shielding film disposed on a first surface of the base plate and having a plurality of through holes reaching the first surface, and a plurality of probe biomolecules bonded to a second surface of the base plate opposite to the first surface of the base plate is provided.

By a ninth aspect of present invention, a biochip comprising an optical transparency base member, a plurality of probe biomolecules bonded on the base member, and a light shielding member disposed around the base member is provided.

BRIEF DESCRIPTION OF DRAWINGS

FIG. 25 shows second chemical formulas of the bases of the nucleosides according to the second embodiment of the present invention.

BEST MODE FOR CARRYING OUT THE INVENTION

Figure 1:
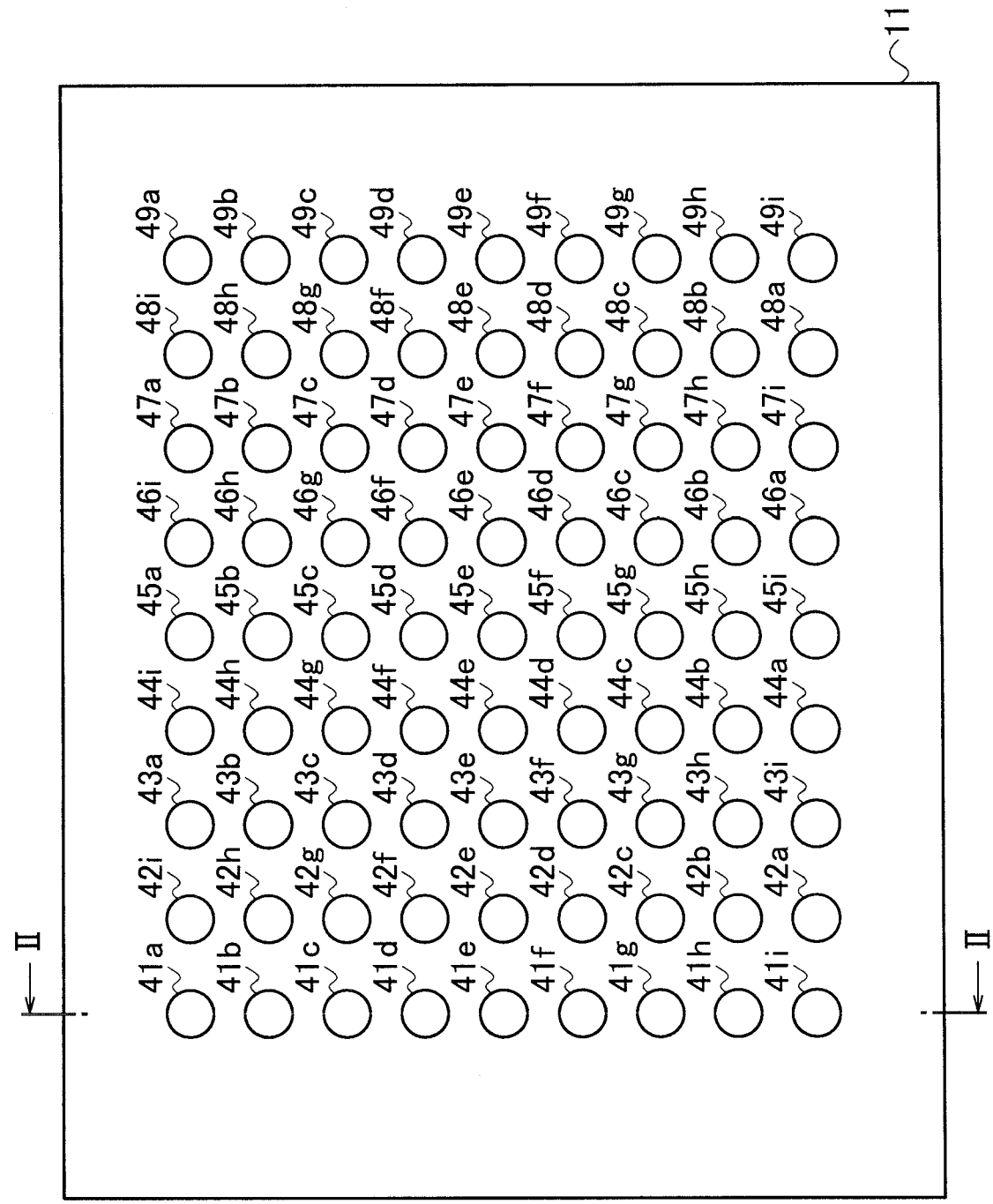
FIG. 1 shows a top view of a substrate for a biochip according to a first embodiment of the present invention.

Embodiments of the present invention will be described with reference to the accompanying drawings. It is to be noted that the same or similar reference numerals are applied to the same or similar parts. It should be noted that the drawing are typical ones. Therefore, concrete sizes should be determined by referring the following description, for example. Also, it is a matter of course that portions of which relationship between sizes and ratios of mutual drawings is different are included.

(FIRST EMBODIMENT)

Figure 2:
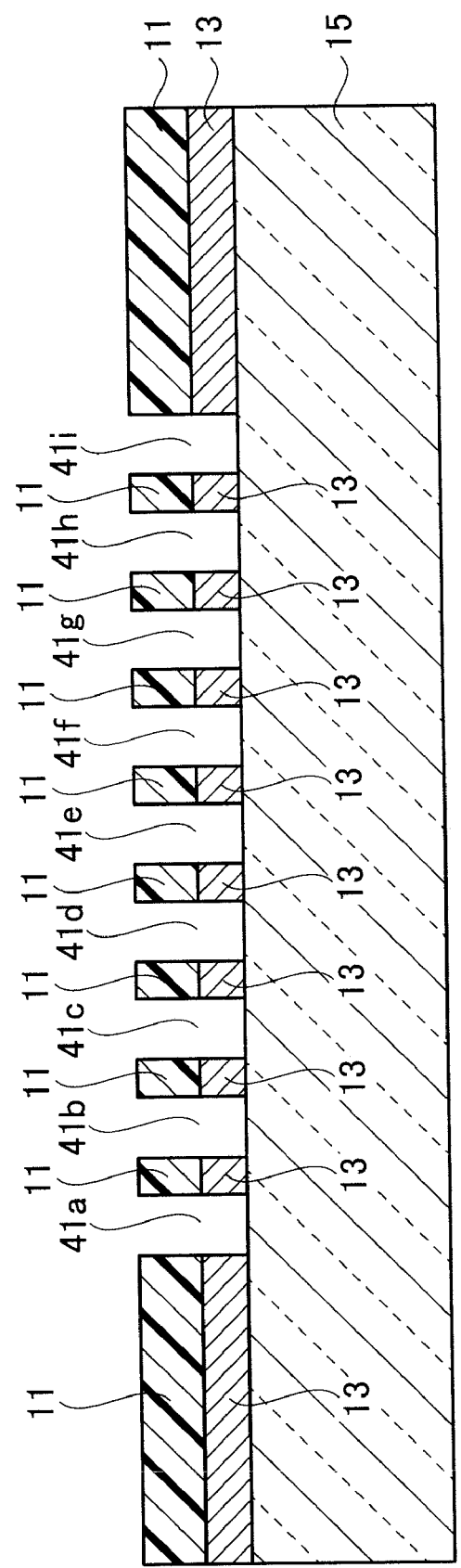
FIG. 2 shows a sectional view of the substrate for the biochip according to the first embodiment of the present invention.

With reference to FIG. 1 and FIG. 2 that is a sectional view taken on line II-II, a substrate for a biochip according to a first embodiment of the present invention includes a base plate 15 having a surface on which a plurality of hydroxyl groups (—OH) can be introduced, and a metallic membrane 13 disposed on the base plate 15, wherein a plurality of wells 41a, 41b, 41c, 41d, 41e, 41f, 41g, 41h, 41i, 42a, 42b, 42c, 42d, 42e, 42f, 42g, 42h, 42i, 43a, 43b, 43c, 43d, 43e, 43f, 43g, 43h, 43i, 44a, 44b, 44c, 44d, 44e, 44f, 44g, 44h, 44i, 45a, 45b, 45c, 45d, 45e, 45f, 45g, 45h, 45i, 46a, 46b, 46c, 46d, 46e, 46f, 46g, 46h, 46i, 47a, 47b, 47c, 47d, 47e, 47f, 47g, 47h, 47i, 48a, 48b, 48c, 48d, 48e, 48f, 48g, 48h, 48i, 49a, 49b, 49c, 49d, 49e, 49f, 49g, 49h, 49i that reach the base plate 15 are delineated in the metallic membrane 13. The film thickness of the base plate 15 is 550 micrometers, for example. Synthetic quarts ($SiO_2$) and a silicon substrate having a surface on which a natural oxide film is formed, etc., can be used for the material of the base plate 15. The film thickness of the metallic membrane 13 is from 10 nm to 10 micrometers, and preferably 50 nm, for example. Transition metal such as Titan (Ti), platinum (Pt), chrome (Cr), niobium (Nb), tantalum (Ta), tungsten (W), etc., or metal such as aluminum (Al), gold (Au), etc., can be used for a material of the metallic membrane 13. Especially, Ti is preferable. In addition, transition metal oxide such as titanium monoxide (TiO), titanium dioxide ($TiO_2$), etc., transition metal nitride such as titanium nitride (TiN), etc., and transition metal carbide such as titanium carbide (TiC) can be used for the material of the metallic membrane 13. Also, ITO (Indium Tin Oxide), etc., can be used for the material of the metallic membrane 13.

Figure 3:
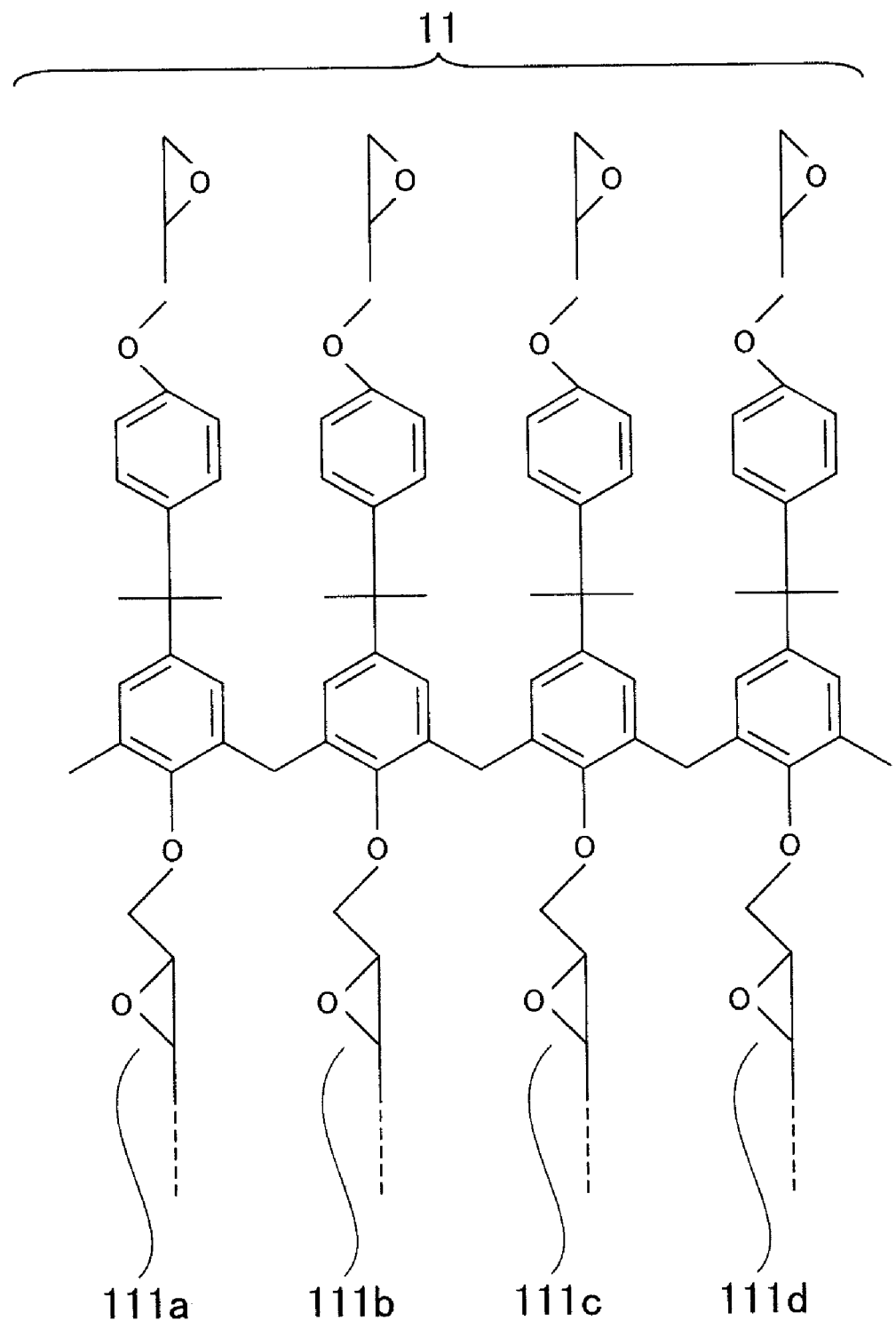
FIG. 3 shows chemical formulas of compositions of polymer membrane according to the first embodiment of the present invention.

Further, the substrate for the biochip according to the first embodiment includes a crosslinkable polymer membrane 11 disposed on the metallic membrane 13. The polymer membrane 11 is insoluble in an acid solution such as a mixed solution of hydrofluoric acid (HF), nitric acid ($HNO_3$), and water ($H_2O$). The film thickness is micrometers. An epoxy resin that is photosensitive to ultraviolet rays cab be used for a material of the polymer membrane 11. For example, SU-8-3000 series of KAYAKU MICROCHEM Corp. is preferable. As shown in FIG. 3, the polymer membrane 11 is composed of a plurality of epoxy resins 111a, 111b, 111c, 111d that are cross-linked to each other.

Figure 26:
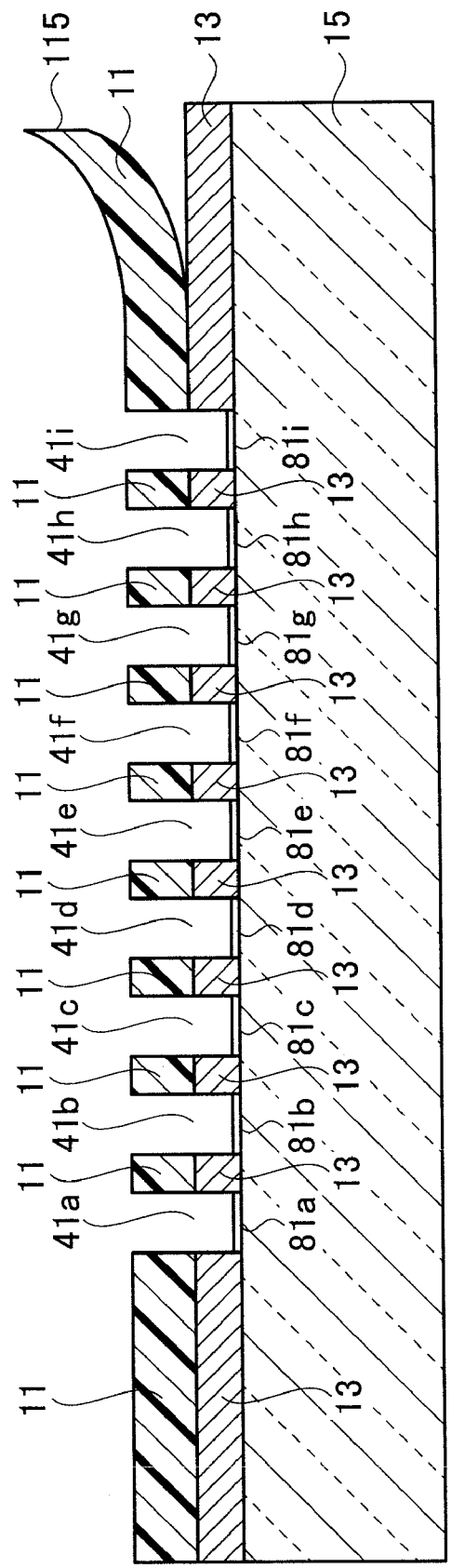
FIG. 26 shows an eleventh sectional process drawing of the biochip according to the second embodiment of the present invention.

When the biochip is manufactured by using the substrate for the biochip described above and shown in FIG. 1 to FIG. 3, as mentioned below with reference to FIG. 26, after probe biomolecules are introduced on a surface of the base plate 15 exposed from the plurality of wells 41a-41i, 42a-42i, 43a-43i, 44a-44i, 45a-45i, 46a-46i, 47a-47i, 48a-48i, 49a-49i and amino groups in the probe biomolecules are deprotected by an alkaline solution, it is possible to easily peel off the polymer membrane 11 from the metallic membrane 13. Especially, by using the SU-8 as the material of the polymer membrane 11, it becomes more easily to peel off it from the metallic membrane 13. After the probe biomolecules are introduced, the polymer membrane 11 can be easily peeled off from the metallic membrane 13. Therefore, it is possible to inhibit the probe biomolecules from being introduced on the surface of metallic membrane 13. Accordingly, the probe biomolecules are introduced only on the surface of the base plate 15 exposed from the plurality of wells 41a-41i, 42a-42i, 43a-43i, 44a-44i, 45a-45i, 46a-46i, 47a-47i, 48a-48i, 49a-49i, and the probe biomolecules do not adhere to the surface of the metallic membrane 13. Consequently, in a process for detecting target biomolecules, it is possible to cancel background noise. By adopting a combination of the polymer membrane 11 and the metallic membrane 13, such phenomenon of easy peel-off after the probe biomolecules are introduced can be observed. Therefore, in the substrate for the biochip according to the first embodiment, the metallic membrane 13 is disposed on the base plate 15, and the polymer membrane 11 is further disposed on the metallic membrane 13.

Figure 4:
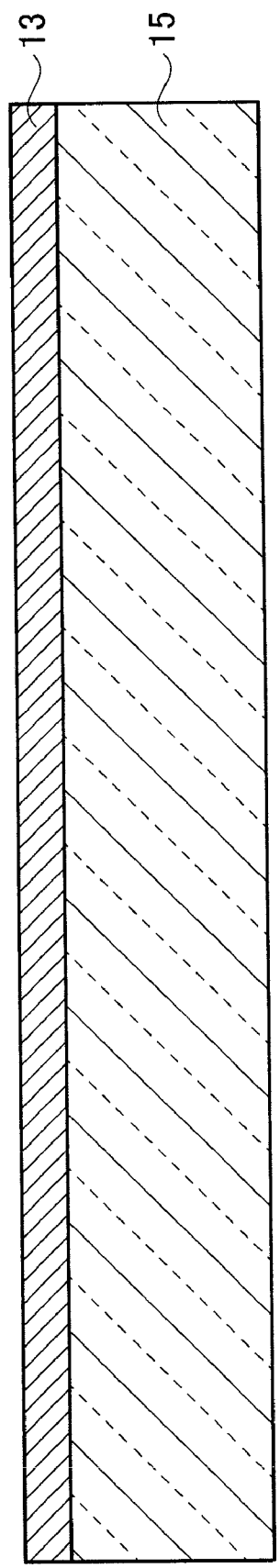
FIG. 4 shows a first sectional process drawing of the substrate for the biochip according to the first embodiment of the present invention.
Figure 5:
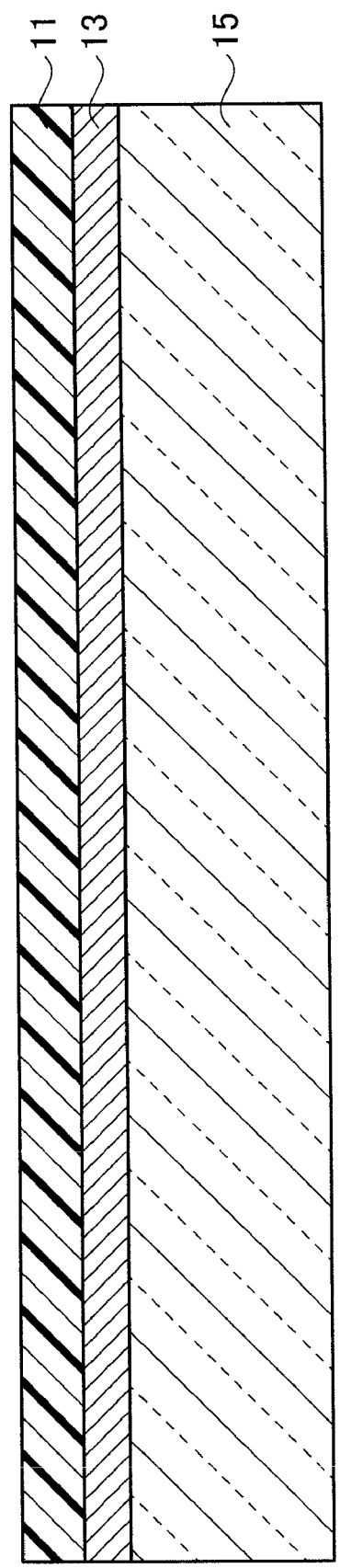
FIG. 5 shows a second sectional process drawing of the substrate for the biochip according to the first embodiment of the present invention.
Figure 6:
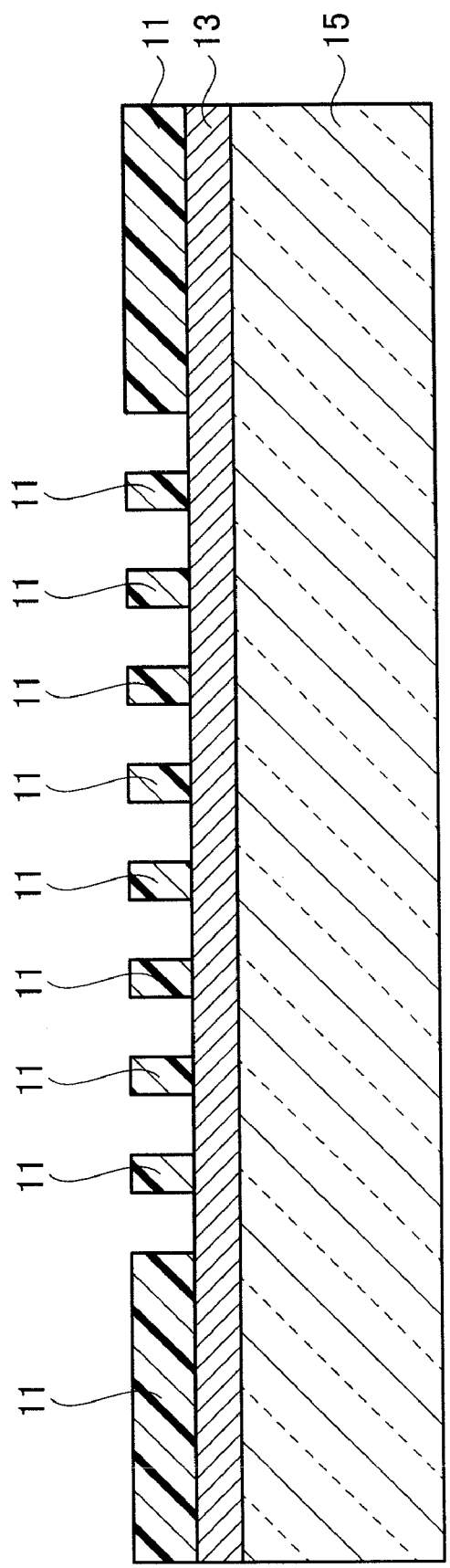
FIG. 6 shows a third sectional process drawing of the substrate for the biochip according to the first embodiment of the present invention.

Next, with reference to FIG. 4 to FIG. 6, a method for manufacturing the substrate for the biochip according to the first embodiment is described.

(a) As shown in FIG. 4, the base plate 15 composed of $SiO_2$, for example, is prepared and the metallic membrane 13 composed of Ti, for example, is formed on the base plate 15 by using a sputtering method or a chemical vapor deposition (CVD) method. After the metallic membrane 13 is formed, the surface is treated with oxygen ($O_2$) plasma for 5 minutes. Next, as shown in FIG. 5, a solution including the photosensitive epoxy resin such as SU-8-3000, etc., is spin coated on the metallic membrane 13 to form the polymer membrane 11. As to the condition of spin coating, it is accelerated to 300 revolutions per minute by taking 5 seconds, and 300 revolutions per minute is maintained for 10 seconds, for example. Further, it is accelerated to 500 revolutions per minute by taking 5 seconds, and 500 revolutions per minute is maintained for 15 seconds. Thereafter, it is accelerated to 4500 revolutions per minute by taking 5 seconds, and the 4500 revolutions per minute is maintained for 30 seconds. Finally, the spin is halted by taking 5 seconds.

(b) After the polymer membrane 11 is formed, the polymer membrane 11 is pre-baked. First, the base plate 15 is disposed on a hot plate set to 65 degrees C. After a lapse of 2 minutes, the hot plate is set to 80 degrees C. After a lapse of 20 minutes, the hot plate is set to 95 degrees C. and it is preserved for 15 minutes. After a lapse of 15 minutes, the hot plate is turned off and it is preserved for 1 hour. Thereafter, by using a photomask having a mask pattern corresponding to shapes of the plurality of wells 41a-41i, 42a-42i, 43a-43i, 44a-44i, 45a-45i, 46a-46i, 47a-47i, 48a-48i, 49a-49i shown in FIG. 1, portions of the polymer membrane 11 are selectively exposed to the ultraviolet rays. After the exposure, post exposure bake (PEB) for the polymer membrane 11 is performed. Concretely, the base plate 15 is disposed on the hot plate set to 65 degrees C. After a lapse of 2 minutes, the hot plate is set to 95 degrees C. and it is preserved for 6 minutes. After a lapse of 6 minutes, the hot plate is turned off and it is preserved for 1 hour. Thereafter, the polymer membrane 11 is developed by using a SU-8 developer solution, for example. Since the polymer membrane 11 has photosensitivity, the portions of the polymer membrane 11 are selectively removed, as shown in FIG. 6.

(c) By using the polymer membrane 11 of which the portions were selectively removed as an etching mask, portions of the metallic membrane 13 are selectively removed by isotopic wet etching. The mixture solution of hydrofluoric acid (HF), nitric acid (HNO$_3$), and water (H$_2$O), for example, can be used for the etching solution. By the selective removal, each of the plurality of wells 41a-41i, 42a-42i, 43a-43i, 44a-44i, 45a-45i, 46a-46i, 47a-47i, 48a-48i, 49a-49i, shown in FIG. 2, are formed and the method for manufacturing the substrate for the biochip according to the first embodiment is completed.

By adopting the method for manufacturing the substrate for the biochip according to the first embodiment described above, the crosslinkable polymer membrane 11 composed of SU-8-3000, etc., has strong solvent resistance against the etching solution. Therefore, there is no need to remove the polymer membrane 11 after the wet etching and to form a new protective film on the metallic membrane 13. Consequently, the polymer membrane 11 can be used as the etching mask for delineating each of the plurality of wells 41a-41i, 42a-42i, 43a-43i, 44a-44i, 45a-45i, 46a-46i, 47a-47i, 48a-48i, 49a-49i and can be utilized for a protective film of the metallic membrane 13 after the etching process. It should be noted that O$_2$ plasma process after formation of the metallic membrane 13 can be eliminated.

(SECOND EMBODIMENT)

Figure 7:
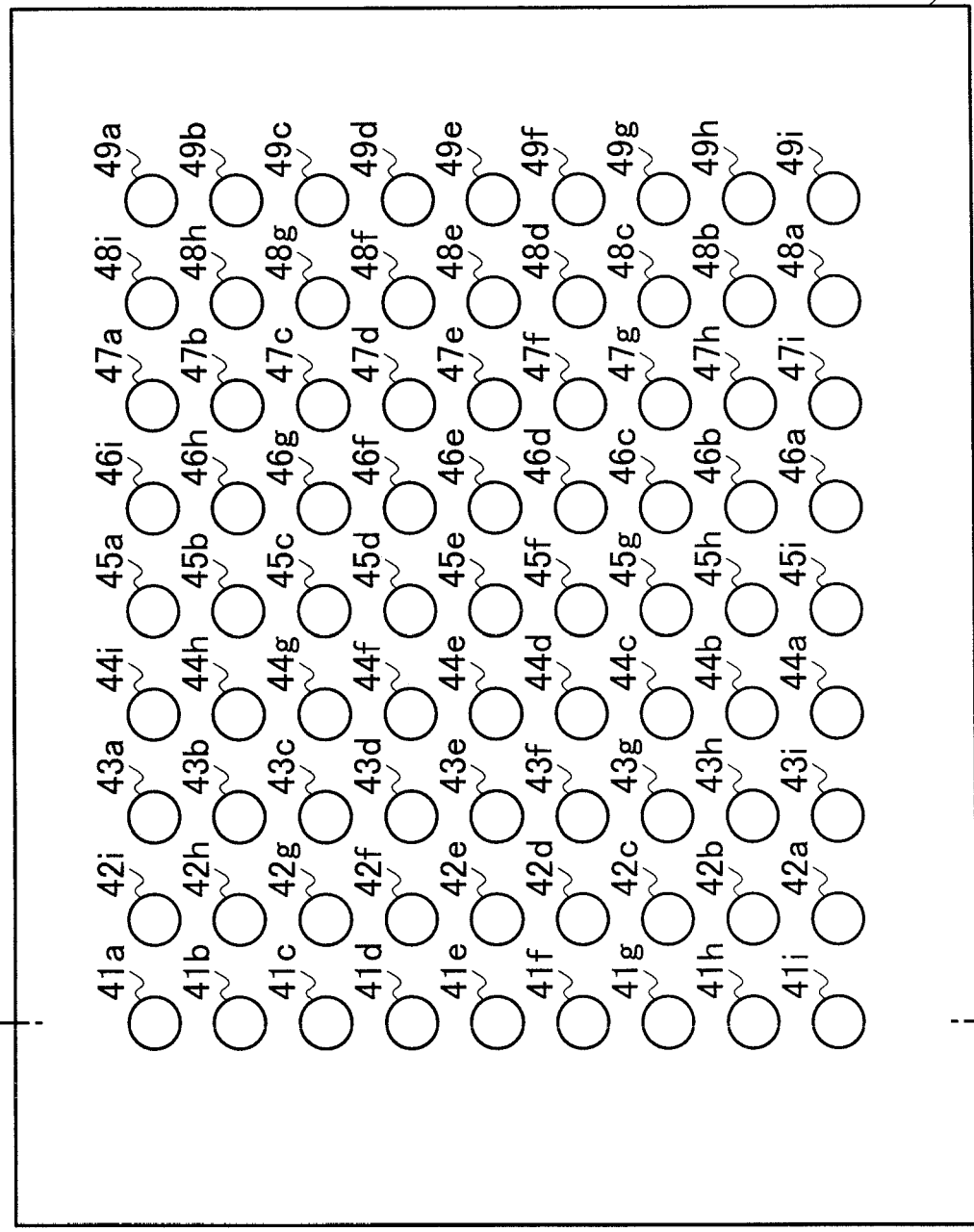
FIG. 7 shows a top view of a biochip according to a second embodiment of the present invention.
Figure 8:
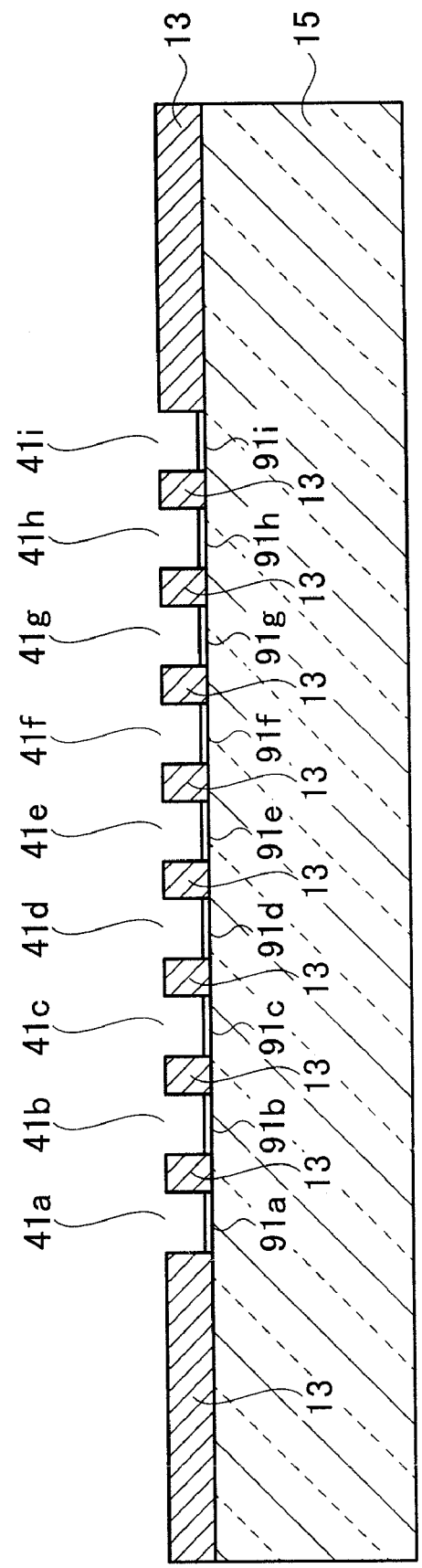
FIG. 8 shows a first sectional view of the biochip according to the second embodiment of the present invention.

With reference to FIG. 7 and FIG. 8 that is a sectional view taken on line VIII-VIII, the biochip according to a second embodiment of the present invention includes the base plate 15, and the metallic membrane 13 disposed on the base plate 15, wherein the plurality of wells 41a, 41b, 41c, 41d, 41e, 41f, 41g, 41h, 41i, 42a, 42b, 42c, 42d, 42e, 42f, 42g, 42h, 42i, 43a, 43b, 43c, 43d, 43e, 43f, 43g, 43h, 43i, 44a, 44b, 44c, 44d, 44e, 44f, 44g, 44h, 44i, 45a, 45b, 45c, 45d, 45e, 45f, 45g, 45h, 45i, 46a, 46b, 46c, 46d, 46e, 46f, 46g, 46h, 46i, 47a, 47b, 47c, 47d, 47e, 47f, 47g, 47h, 47i, 48a, 48b, 48c, 48d, 48e, 48f, 48g, 48h, 48i, 49a, 49b, 49c, 49d, 49e, 49f, 49g, 49h, 49i that reach the base plate 15 are delineated in the metallic membrane 13. Each film thickness and each material of the base plate 15 and the metallic membrane 13 are similar to the substrate for the biochip shown in FIG. 1. So, an explanation is omitted.

Figure 9:
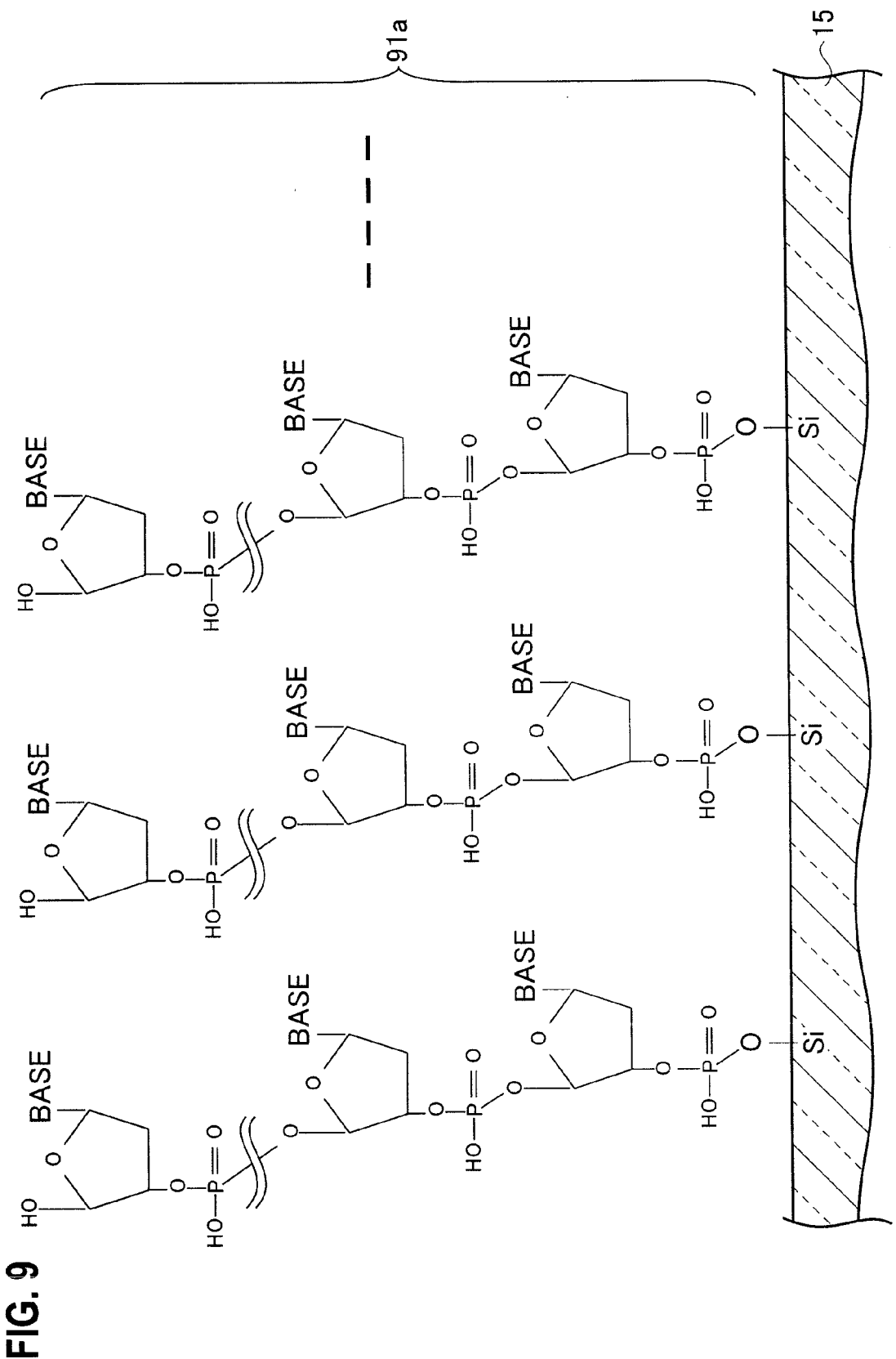
FIG. 9 shows an first enlarged sectional view of the biochip according to the second embodiment of the present invention.

With reference to FIG. 8, the biochip according to the second embodiment further includes a plurality of biomaterial films 91a, 91b, 91c, 91d, 91e, 91f, 91g, 91h, 91i disposed on the surface of the base plate 15 exposed from the plurality of wells 41a-41i, respectively. In each of the plurality of biomaterial films 91a-91i, each functional group of a plurality of probe biomolecules such as a plurality of DNAs, a plurality of ribonucleic acids (RNAs), a plurality of peptide nucleic acids (PNAs), a plurality of proteins, etc., is covalently bonded to the hydroxyl group (—OH) on the surface of the base plate, as shown in FIG. 9. In the case where the probe biomolecules are DNAs, RNAs, or PNAs, each sequence is designed to be complementary to a target biomolecule.

Figure 10:
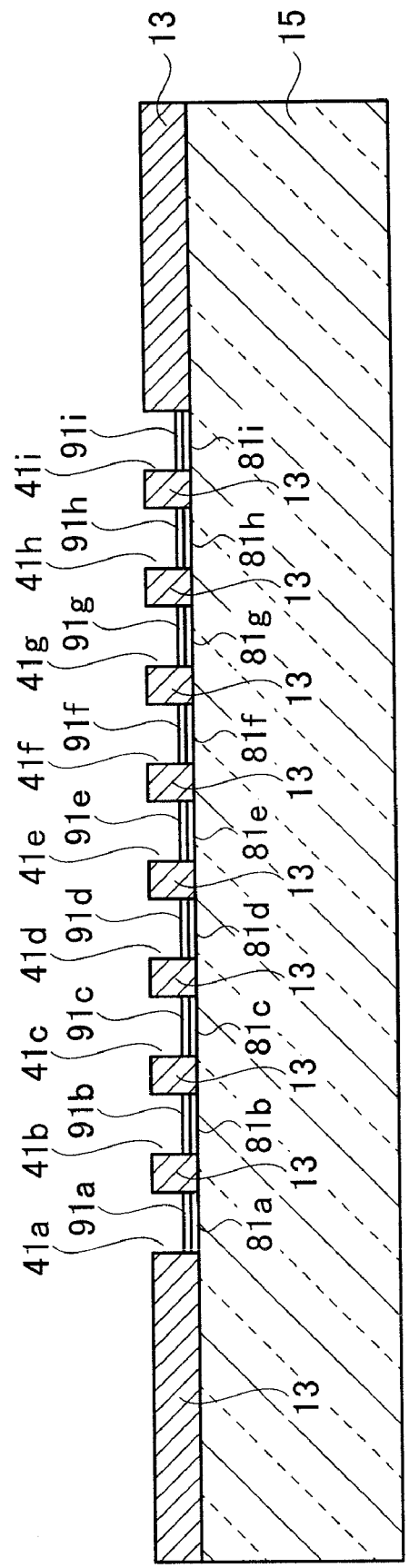
FIG. 10 shows a second sectional view of the biochip according to the second embodiment of the present invention.
Figure 11:
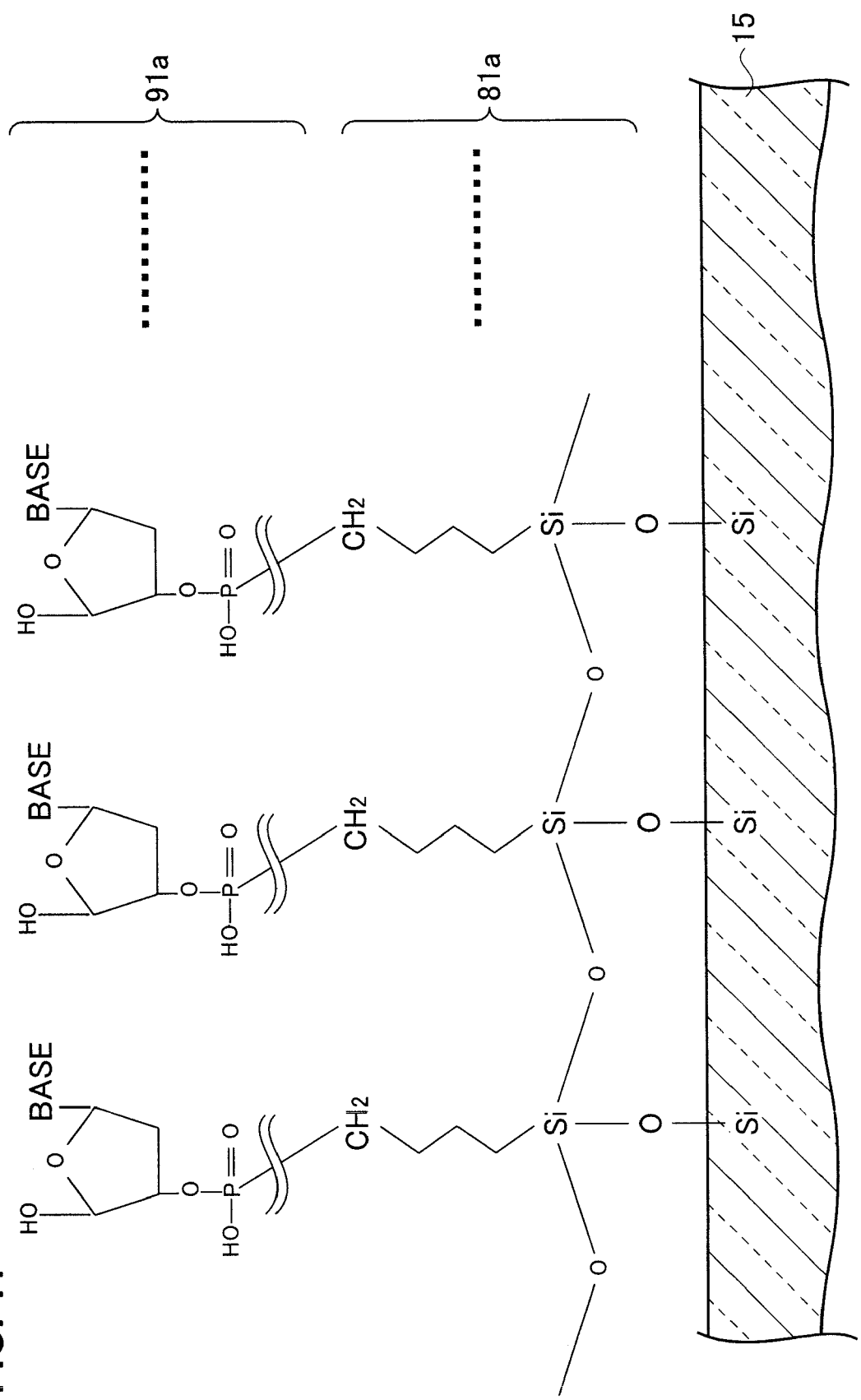
FIG. 11 shows a second enlarged sectional view of the biochip according to the second embodiment of the present invention.

It should be noted that the second embodiment is not limited to directly disposing each of the plurality of biomaterial films 91a-91i on the surface of the base plate 15. In the case shown in FIG. 10, silane coupling films 81a, 81b, 81c, 81d, 81e, 81f, 81g, 81h, 81i are disposed on the portions of the surface of the base plate 15 exposed from the plurality of wells 41a-41i, respectively. In each of the silane coupling films 81a-81i, as shown in FIG. 11, each methyl group (—CH$_3$) or each ethyl group (—C$_2$H$_5$) of a plurality of silane coupling agents is chemically bounded to the hydroxyl group (—OH) on the surface of the base plate 15 by acid-base reaction.

3-Glycidoxypropyltrimethoxysilane, 3-Glycidoxypropylmethyldiethoxysilane, 3-Glycidoxypropyltriethoxysilane, N-(2-Aminoethyl)-3-Aminopropylmethyldimethoxysilane, N-(2-Aminoethyl)-3-Aminopropyltrimethoxysilane, N-(2-Aminoethyl)-3-Aminopropyltriethoxysilane, 3-Aminopropyltrimethoxysilane, 3-Aminopropyltriethoxysilane, etc., can be used for each of the plurality of silane coupling agents.

The biomaterial films 91a, 91b, 91c, 91d, 91e, 91f, 91g, 91h, 91i are disposed on the silane coupling films 81a-81i, respectively. In each of the plurality of biomaterial films 91a-91i, each phosphoramidite derivative introduced in the plurality of probe biomolecules is covalently bonded to each epoxy group of the silane coupling agents in the silane coupling films 81a-81i, by hydrolysis reaction.

Alternatively, the silane coupling agent and the probe biomolecule may bond via cross linker. For example, a functional group such as amino group (—NH$_2$) of lysine (Lys), carboxyl group (—COOH) of aspartic acid (Asp) and glutamic acid (Glu), phenolic group (—C$_6$H$_4$(OH)) of tyrosine (Tyr), imidazole group (—C$_3$H$_3$N$_2$) of histidine (His), thiol group (—SH) of cysteine (Cys), etc., included in the protein such as a receptor, ligand, antagonist, antibody, antigen, etc., may be bonded to the amino group or the epoxy group of the silane coupling agent by the cross linker. In the case shown in FIG. 12, the amino group (—NH$_2$) of the silane coupling agent and each amino group (—NH$_2$) of the antibodies 95a, 95b, 95c are bonded by a Disuccinimidyl suberate (DSS) that is the cross linker reacting to the amino groups (—NH$_2$) at both terminals.

In addition, Bis[Sulfosuccinimidyl]suberate (BS$^3$), Dimethyl suberimidate HCl (DMS), Disuccinimidyl glutarate (DSG), Loman's Reagent, 3,3'-Dithiobis[sulfosuccinimidyl propionate] (DTSSP), and Ethylene glycol bis[succinimidylsuccinate] (EGS) that react to the amino groups at both terminals, and 1-Ethyl-3-[3-Dimethylaminopropyl]carbodiimide Hydrochloride (EDC) that react to the amino group and the carboxyl group can be used for the cross linker.

In addition, m-Maleimidobenzyl-N-hydroxysuccinimide ester (MBS), Succinimidyl 4-[N-maleimidomethyl]-cyclohexane-1-carboxylate (SMCC), Succinimidyl 4-[p-maleimidophenyl]-butyrate (SMPB), N-Succinimidyl 3-[2-pyridyldithio]propionate (SPDP), N-[γ-Maleimidobutyloxy]sulfosuccinimide ester (Sulfo-GMBS), Sulfosuccinimidyl 6-[3'(2-pyridyldithio)-propionamide]hexanoate (Sulfo-LC-SPDP), m-Maleimidebenzoyl-N-hydroxysulfo-succinimide ester (Sulfo-MBS), Sulfosuccinimidyl 4[N-maleimidomethyl]-cyclohexane-1-carboxylate (Sulfo-SMCC), and Sulfosuccinimidy 4-[p-maleimidophenyl]-butyrate (Sulfo-SMPB) that react to the amino group and the thiol group can also be used as the cross linker. It should be noted that each sectional view of the other plurality of wells 42a-42i, 43a-43i, 44a-44i, 45a-45i, 46a-46i, 47a-47i, 48a-48i, 49a-49i shown in FIG. 7 is similar to FIG. 8 to FIG. 12. So, an explanation is omitted.

Next, with reference to FIG. 13 to FIG. 27, a method for manufacturing the biochip according to the second embodiment is described.

Figure 13:
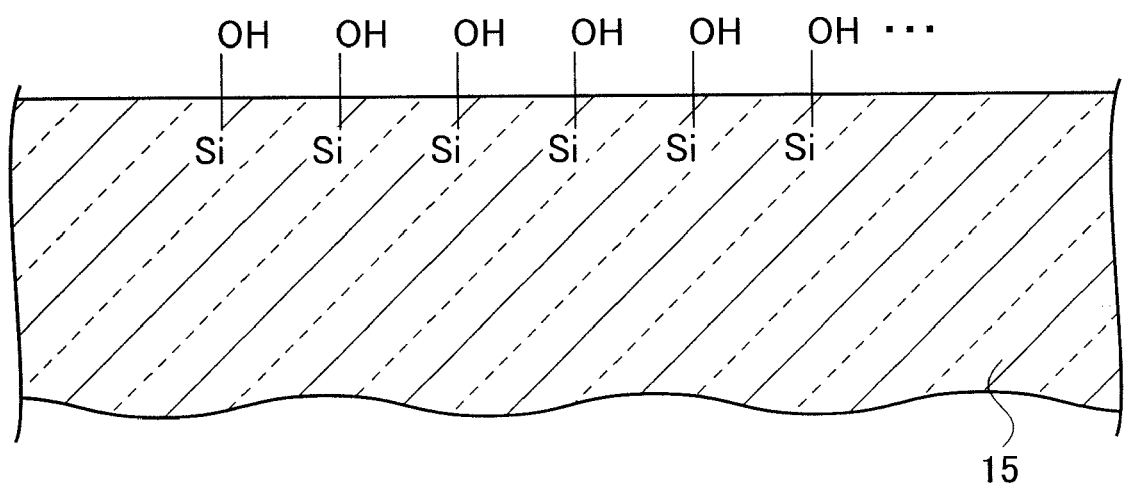
FIG. 13 shows a first sectional process drawing of the biochip according to the second embodiment of the present invention.

(a) First, the substrate for the biochip shown in FIG. 1 and FIG. 2 is prepared. Next, the substrate for the biochip is left in a stirred sodium hydroxide (NaOH) solution at room temperature for 2 hours. Here, the NaOH solution is a solution obtained by mixing 98 g of NaOH, 294 ml of distilled water, and 392 ml of ethanol. By leaving it in the NaOH solution, the plurality of hydroxyl groups (—OH) are introduced on the surface of base plate 15 exposed from each of the wells 41a-41i, as shown in FIG. 13. It should be noted that the hydroxyl groups (—OH) may also be introduced by using a UV ozone cleaner, for example.

Figure 14:
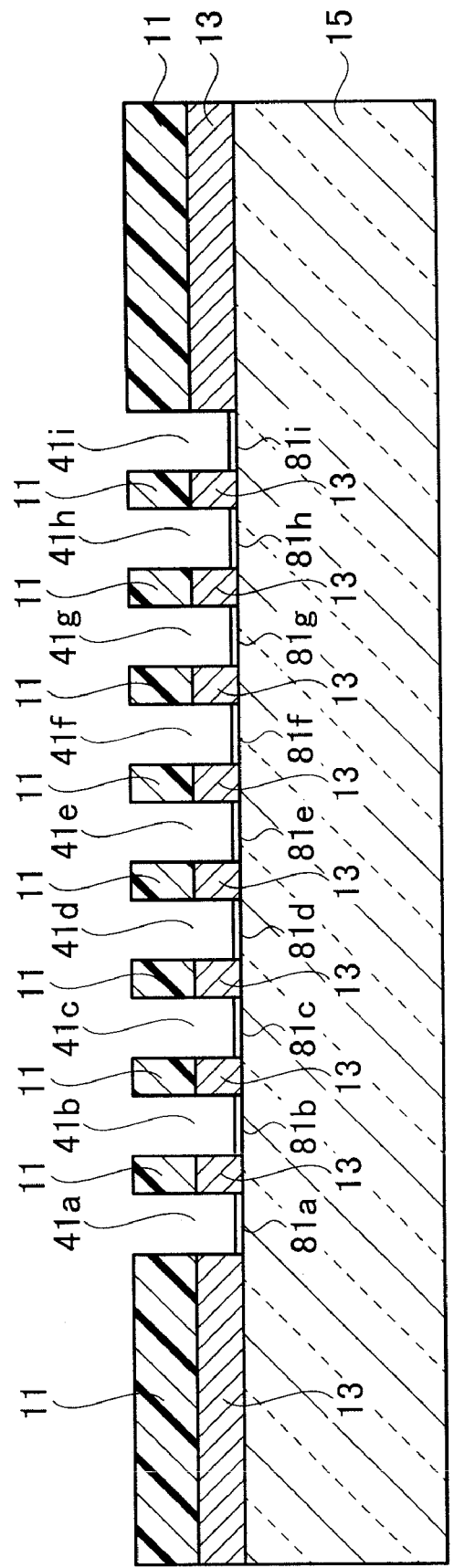
FIG. 14 shows a second sectional process drawing of the biochip according to the second embodiment of the present invention.
Figure 15:
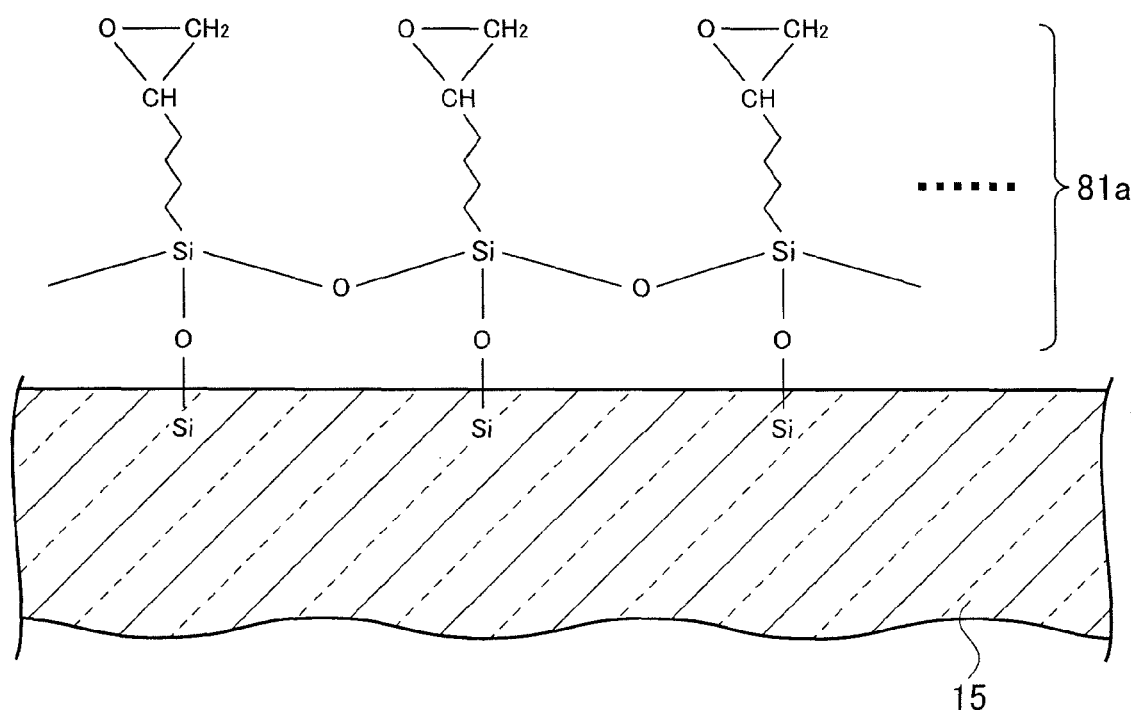
FIG. 15 shows a third sectional process drawing of the biochip according to the second embodiment of the present invention.

(b) For example, the silane coupling agent having the epoxy group as the functional group such as 3-Glycidoxypropylmethyldiethoxysilane 3-Glycidoxypropyltriethoxysilane, etc., or the silane coupling agent having the amine as the functional group such as N-(2-Aminoethyl)-3-Aminopropyltriethoxysilane, 3-Aminopropyltrimethoxysilane, 3-Aminopropyltriethoxysilane, etc., is dropped on the surface of the base plate 15 exposed from each of the wells 41a-41i shown in FIG. 2 to form each of the silane coupling films 81a, 81b, 81c, 81d, 81e, 81f, 81g, 81h, 81i shown in FIG. 14. For example, when the silane coupling agent having the epoxy group is dropped under 15 degrees C. condition, the plurality of epoxy groups are introduced on the surface of the base plate 15, as shown in FIG. 15. In the case where the metallic membrane 13 shown in FIG. 14 is opaque, it becomes easy to determine the locations of wells 41a-41i, when the silane coupling agent is dropped.

Figure 16:
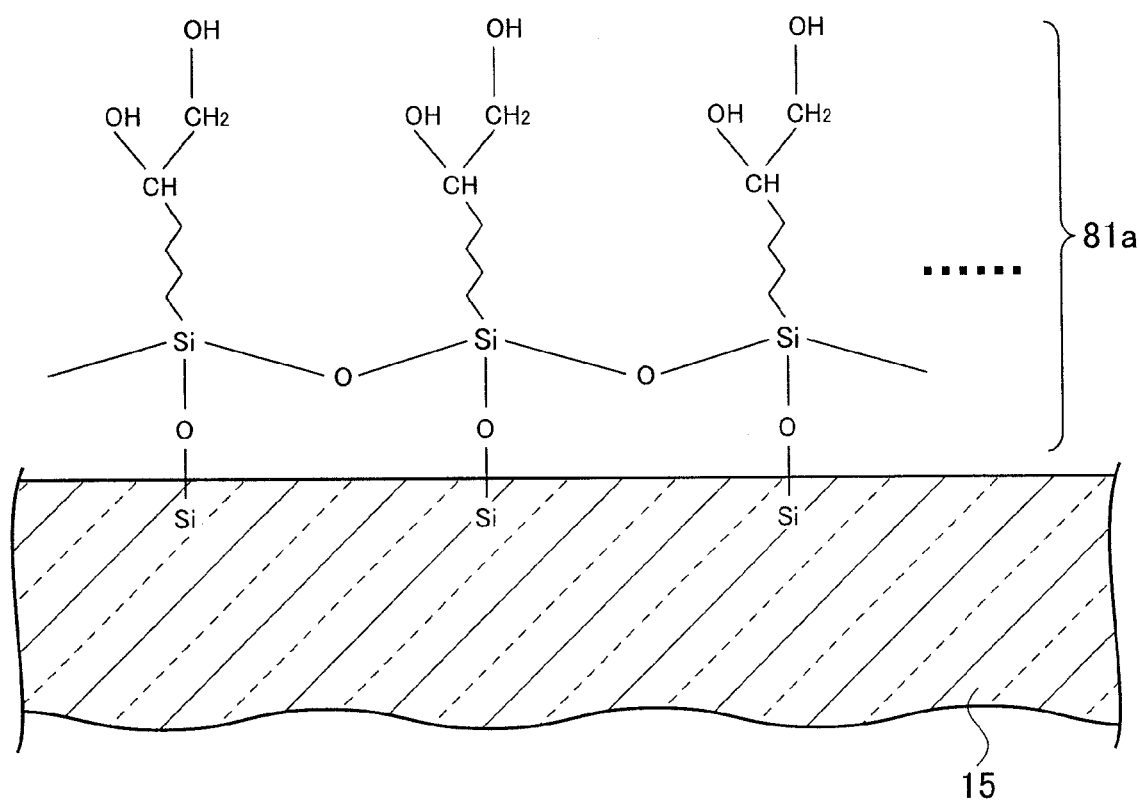
FIG. 16 shows a fourth sectional process drawing of the biochip according to the second embodiment of the present invention.

(c) Unreacted hydroxyl groups (—OH) remaining on the surface of the base plate 15 is acetylated to be capped by treatment with acetic anhydride and 1-methylimidazole (tetrahydrofuran solution). Next, as shown in FIG. 16, the epoxy groups of the silane coupling agent introduced on the surface of the base plate 15 is hydrolyzed and the hydroxyl groups (—OH) are introduced in each of the silane coupling films 81a-81i.

Figure 17:
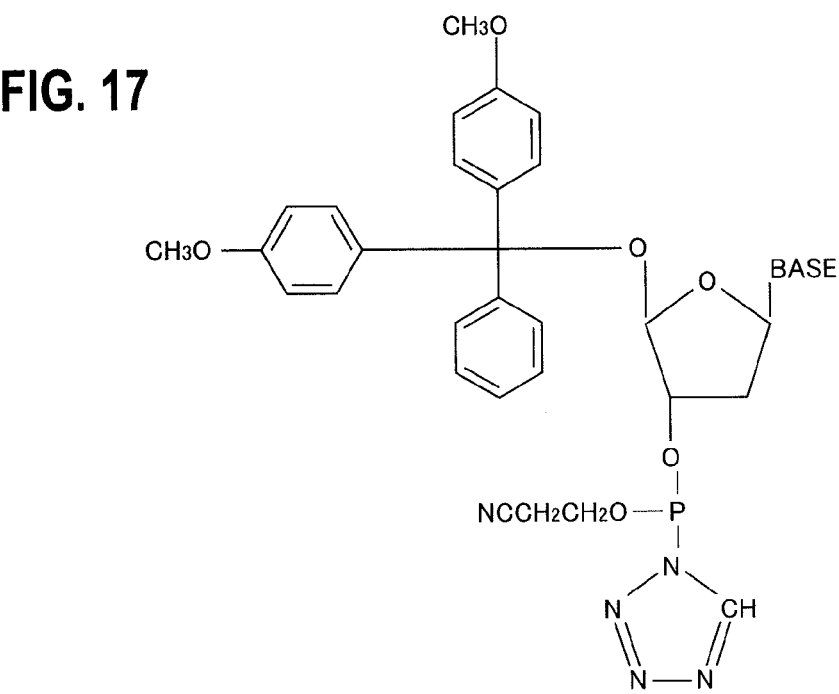
FIG. 17 shows a chemical formula of nucleoside phosphoramidite according to the second embodiment of the present invention.
Figure 18:
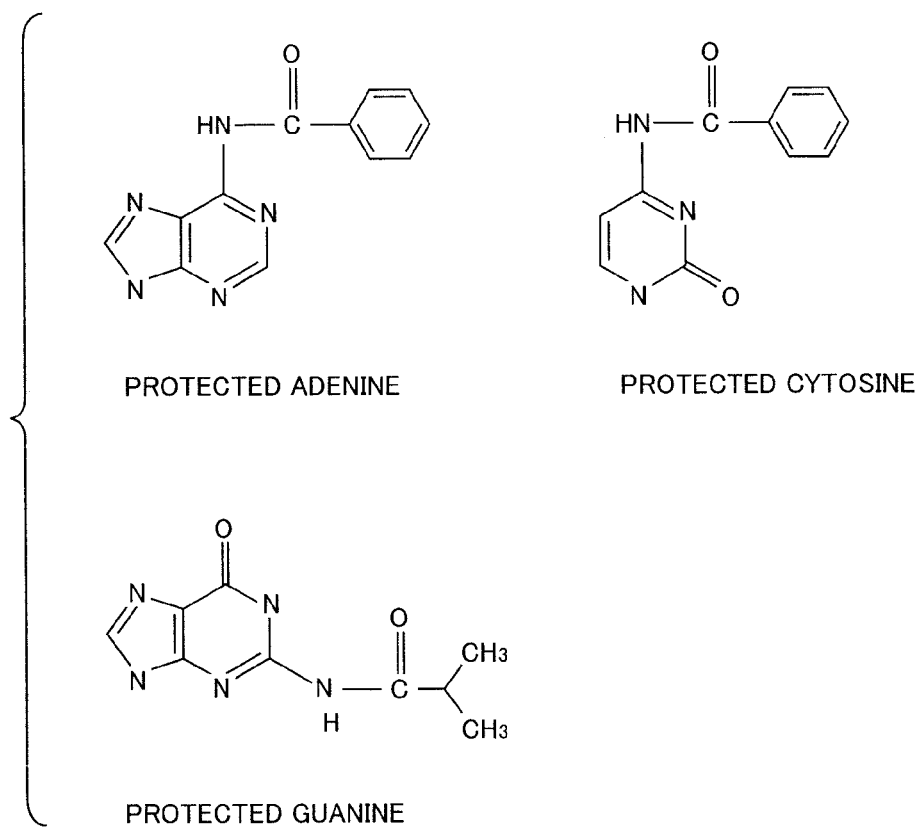
FIG. 18 shows first chemical formulas of bases of the nucleosides according to the second embodiment of the present invention.
Figure 19:
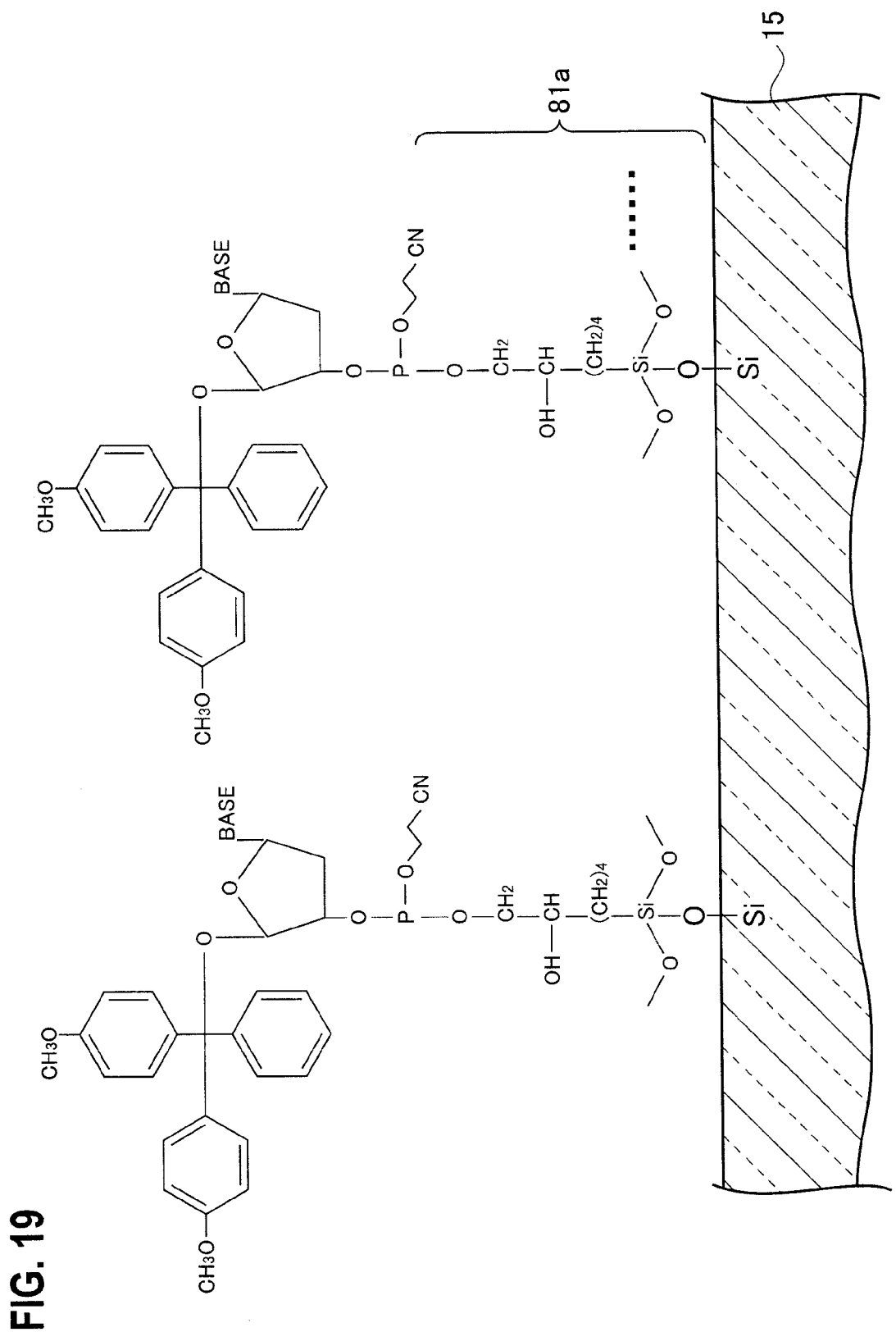
FIG. 19 shows a fifth sectional process drawing of the biochip according to the second embodiment of the present invention.

(d) As shown in FIG. 17, a nucleoside of which 5' terminal is protected by Dimethoxytrityl (DMTr) group and a trivalent phosphoramidite derivative is substituted for hydroxyl group of 3' terminal is prepared as a first base. Here, as shown in FIG. 18, amino group of adenine (A) and cytosine (C) included in the nucleoside is protected by the benzoyl group, and amino group of guanine (G) is protected by the isobutyl group. Next, the nucleoside as the first base is dropped onto each of the silane coupling films 81a-81i shown in FIG. 14. By the dropping, phosphoric cyanoethyl amidite derivative of the nucleoside as the first base is bonded to the hydroxyl group (—OH) of the silane coupling agent, as shown in FIG. 19, by using the base catalyst, for example.

Figure 20:
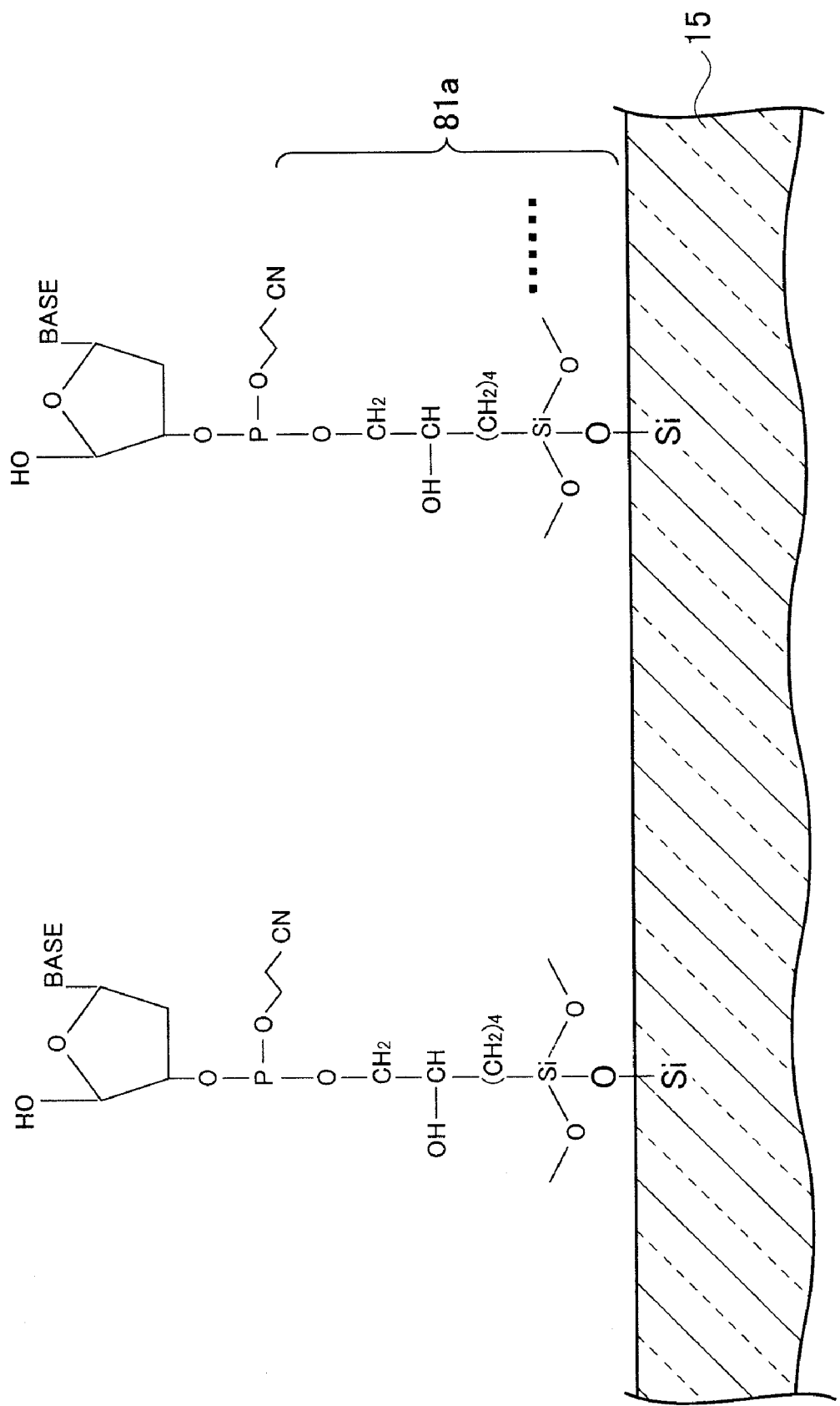
FIG. 20 shows a sixth sectional process drawing of the biochip according to the second embodiment of the present invention.

(e) The unreacted hydroxyl groups (—OH) of the silane coupling agents are acetylated by treatment with acetic anhydride and 1-methylimidazole (tetrahydrofuran solution) and bondings to the nucleosides from a second base onward are inhibited. Next, Dimethoxytrityl (DMTr) groups of the nucleosides as the first bases are deprotected by a 3% trichloroacetic acid/dichloromethane acid solution and 5' hydroxyl groups (—OH) are introduced in the nucleosides as the first bases, as shown in FIG. 20.

Figure 21:
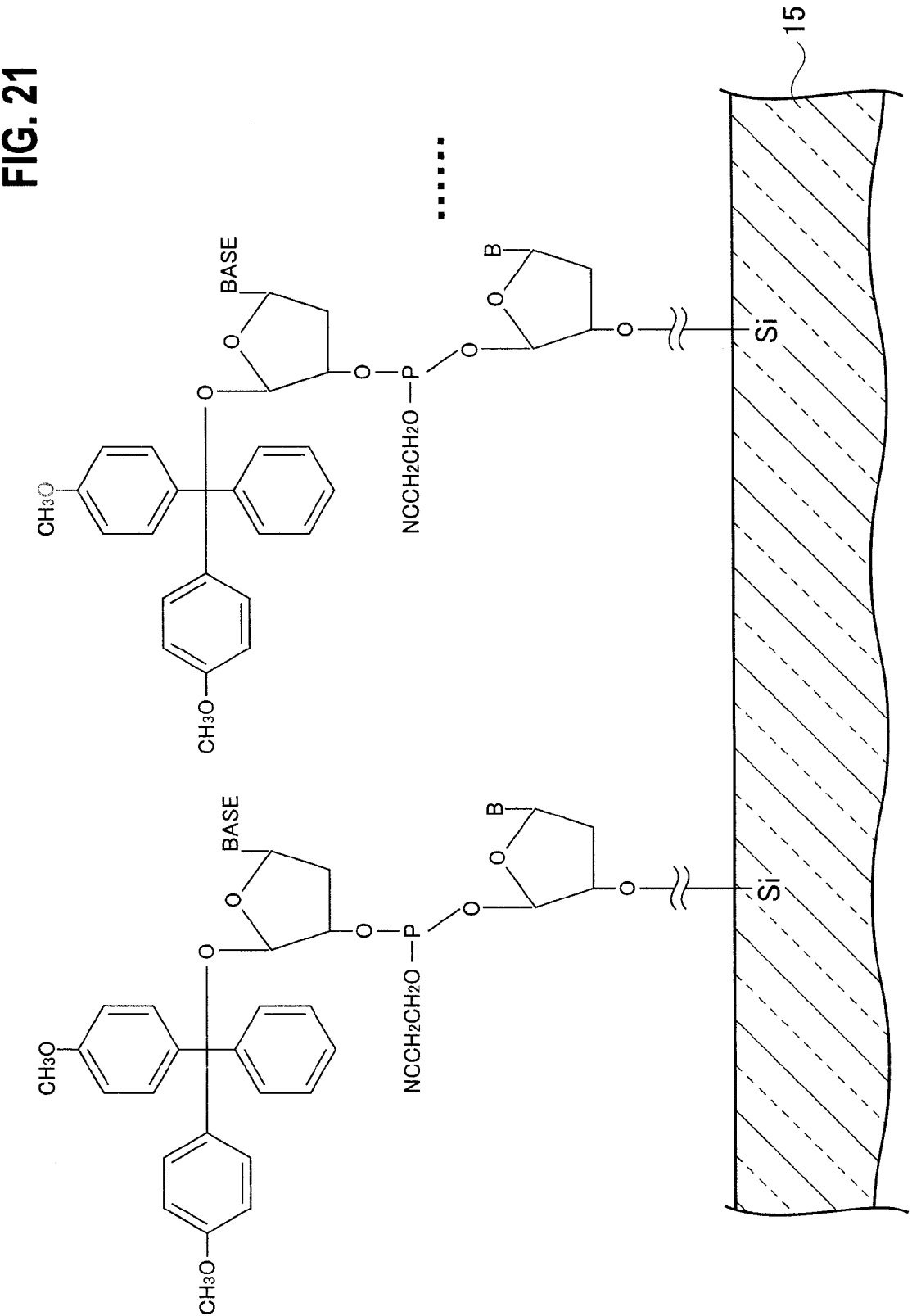
FIG. 21 shows a seventh sectional process drawing of the biochip according to the second embodiment of the present invention.

(f) The nucleosides as the second bases of which trivalent phosphoramidite derivatives are substituted for the 3' terminal hydroxyl groups are dropped onto the silane coupling films 81a-81i, and as shown in FIG. 21, the phosphoric cyanoethyl amidite derivatives of the nucleosides as the second bases are bonded to the 5' hydroxyl groups (—OH) of the nucleosides as the first bases by condensation reaction, with base catalyst, for example. Then, unreacted 5' hydroxyl groups (—OH) of the nucleosides as the first bases are acetylated to be capped by treatment with acetic anhydride and tetrahydrofuran solution.

Figure 22:
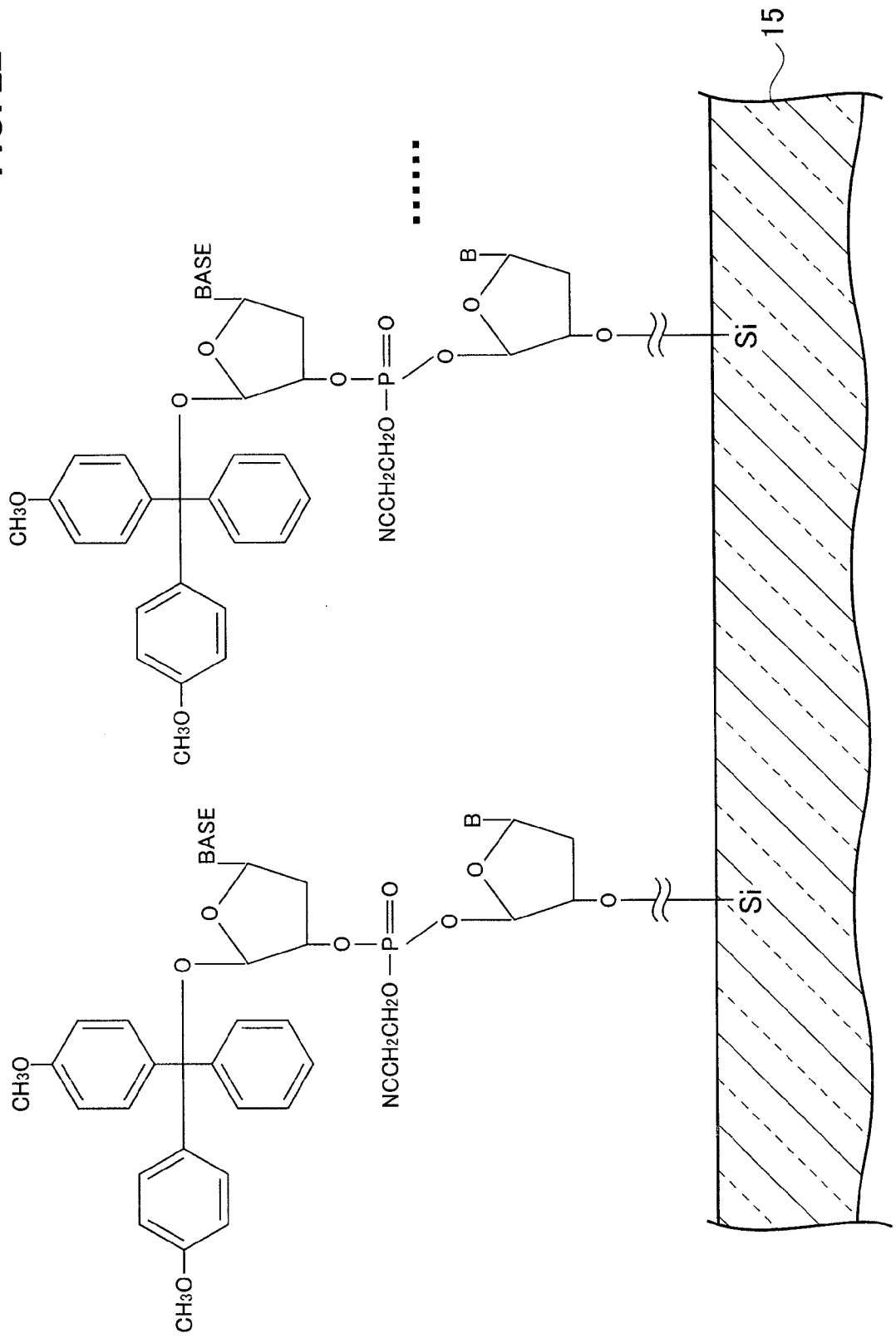
FIG. 22 shows an eighth sectional process drawing of the biochip according to the second embodiment of the present invention.
Figure 23:
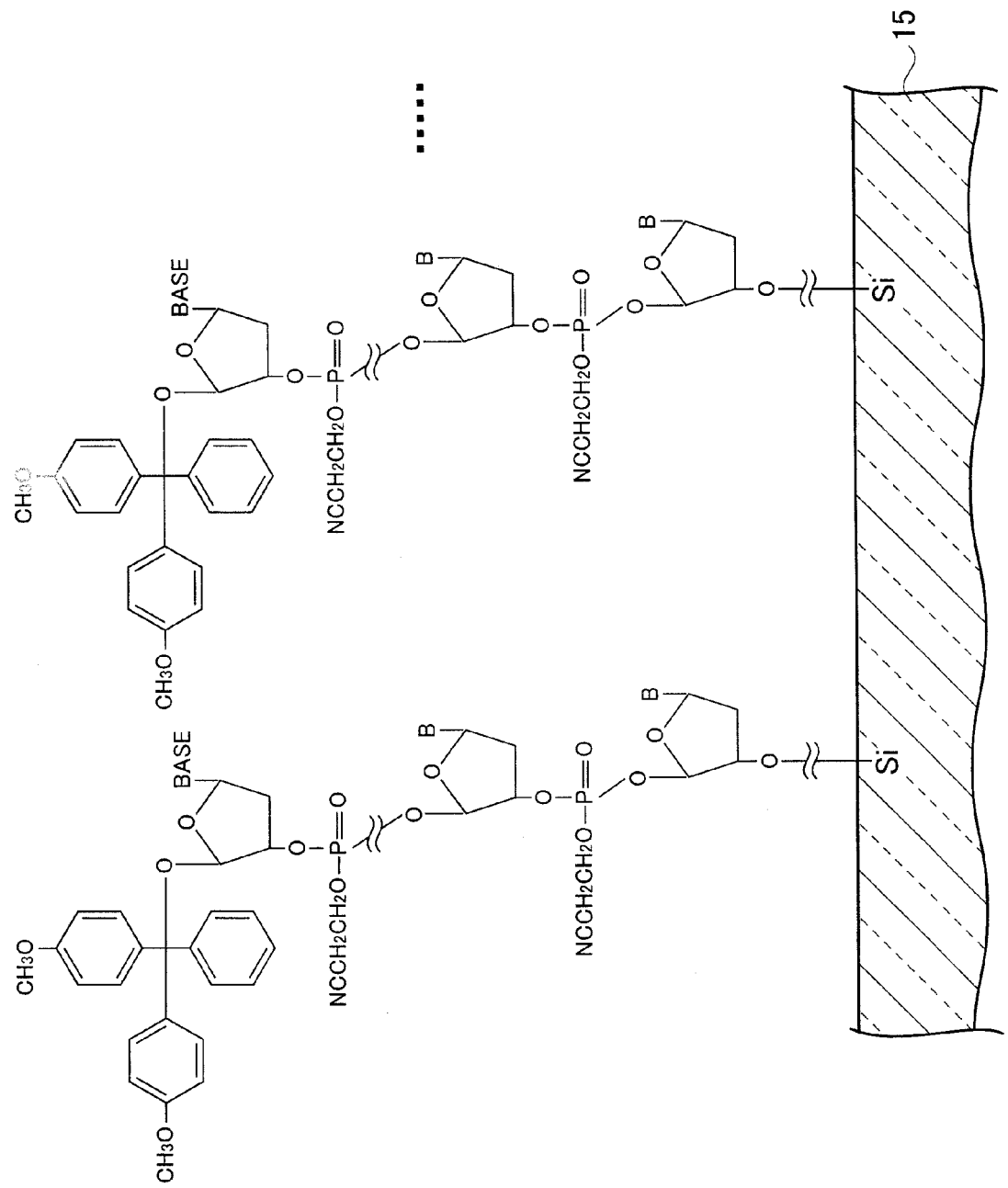
FIG. 23 shows a ninth sectional process drawing of the biochip according to the second embodiment of the present invention.

(g) Phosphite triester bonds formed by the condensation reaction are oxidized with iodine and water (pyridine-containing tetrahydrofuran solution) and they change to more stable phosphoric triester bonds, as shown in FIG. 22. Thereafter, Dimethoxytrityl (DMTr) groups of the second bases are removed. Then, the condensation reactions to the nucleoside phosphoramidites are repeated until the desired DNA chain length is obtained, as shown in FIG. 23, and the plurality of biomaterial films 91a-91i shown in FIG. 10 are formed.

Figure 24:
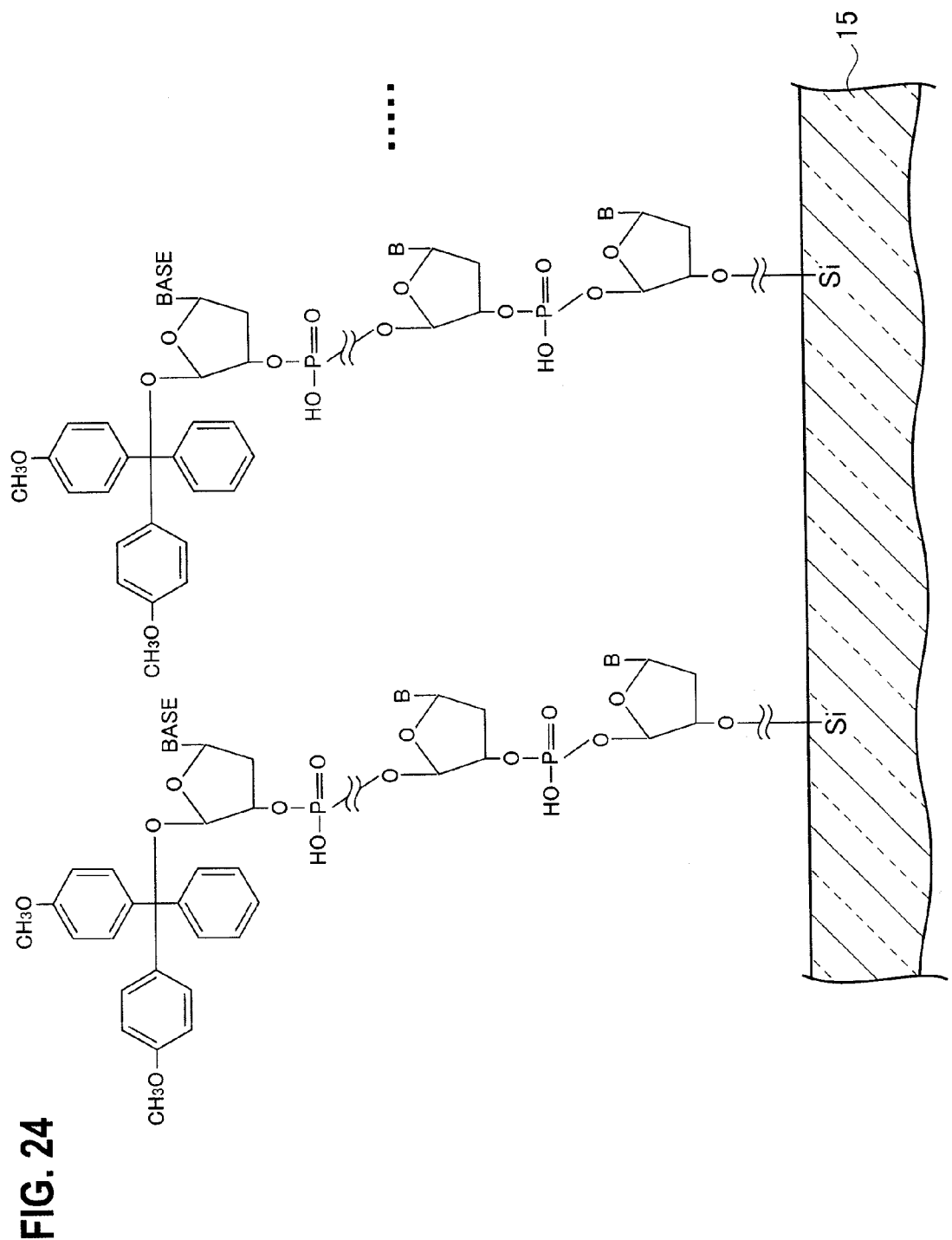
FIG. 24 shows a tenth sectional process drawing of the biochip according to the second embodiment of the present invention.
Figure 27:
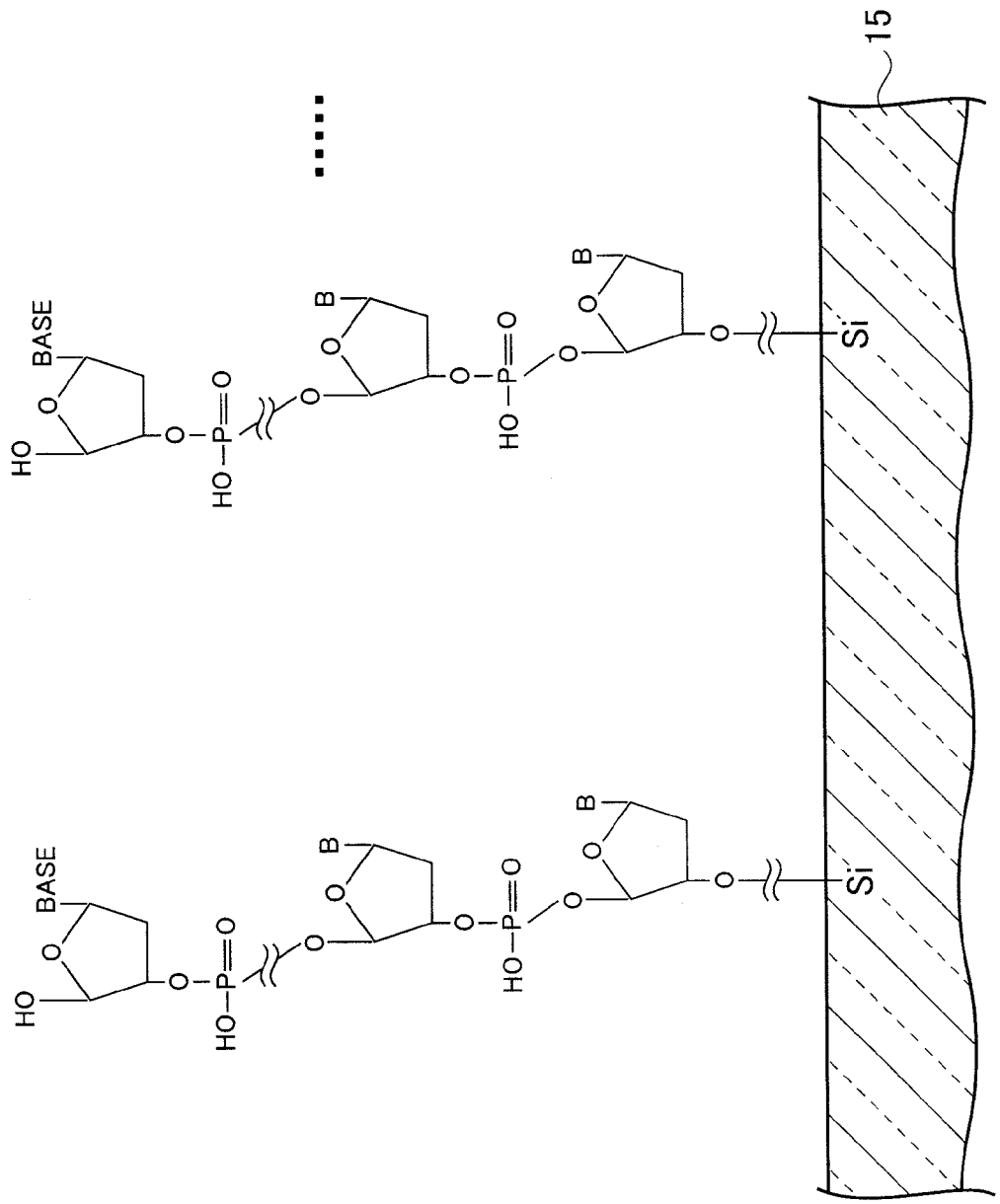
FIG. 27 shows a twelfth sectional process drawing of the biochip according to the second embodiment of the present invention.

(h) After the DNA is elongated, an alkaline solution treatment is performed. Here, the base plate 15 is sunk in the alkaline solution such as ammonia water ($NH_4OH$) at 55 degrees C. for 30 minutes so that the polymer membrane 11 is soaking. It should be noted that the weight percent concentration is 40% at the preparation time. By the alkaline solution treatment, as shown in FIG. 24, cyanoethyl protecting groups are detached. Also, bases such as adenine (A), cytosine (C), and guanine (G) are deprotected as shown in FIG. 25. Further, by the alkaline solution treatment, adhesion force between the metallic membrane 13 and the polymer membrane 11 is diminished. Thereafter, the base plate 15 is took out from the $NH_4OH$ water, and the lateral side 115 of the polymer membrane 11 shown in FIG. 26 is blown by gas such as air by using an air gun, for example, to peel off the polymer membrane 11 from the metallic membrane 13. Finally, the end terminal Dimethoxytrityl (DMTr) groups are deprotected, as shown in FIG. 27, and the method for manufacturing the biochip according to the second embodiment is completed.

In an earlier method for manufacturing the biochip, there was no technique for protecting the membrane having the plurality of wells by the polymer membrane during formation of the biomaterial film and then easily peeling off the polymer membrane from the membrane having the plurality of wells. Therefore, if the biomaterial film was formed without protecting the membrane having the plurality of wells, the silane coupling agents were bonded to the surface of the membrane having the plurality of wells, and the probe biomolecules were bonded to the silane coupling agents. Consequently, there was a problem that the fluorescently-labeled target biomolecules also bonded to the surface of the membrane having the plurality of wells and it became the background noise during the detection process. Especially in a micro amount assay, a technique for enhancing contrast in fluorescent assay by trapping the target biomolecules only on the surface of the substrate exposed from each of the plurality of wells and inhibiting the target biomolecule from being trapped on the surface of membrane having the wells was desired.

However, by the method for manufacturing the biochip according to the second embodiment, as shown in FIG. 13 to FIG. 27, the metallic membrane 13 is protected by the polymer membrane 11 during the formation of the plurality of biomaterial films 91a-91i, and the polymer membrane 11 is peeled off from the metallic membrane 13 after the formation of the plurality of biomaterial films 91a-91i. Therefore, the probe biomolecules are not introduced onto the metallic membrane 13. Consequently, the target biomolecules are not bonded on the metallic membrane 13. Accordingly, by using the biochip according to the second embodiment, it is possible to detect species and concentration of the target biomolecule with considerable accuracy, for example, since the background noise does not generate in the process for detecting the biomolecule. Further, in the process for synthesis of DNA shown in FIG. 17 to FIG. 25, it is possible to secure each depth of the plurality of wells 42a-49i, since the polymer membrane 11 is disposed on the metallic membrane 13. Therefore, it is possible to drop sufficient synthesis reagents for synthesis of DNA into each of the plurality of wells 42a-49i. Further, it is possible to easily peel off the polymer membrane 11 from the metallic membrane 13 by immersing it in the $NH_4OH$ water used for the desorption of cyanoethyl protecting group and the deprotection of adenine (A), cytosine (C), guanine (G), for example. Therefore, it is not necessary to prepare a specific stripping solution to peel off the polymer membrane 11. Also, it is not necessary to immerse the polymer membrane 11 into the specific stripping solution. Therefore, it is not feared that the probe biomolecules in the plurality of biomaterial films 91a-91i are damaged. The phenomenon of easy peeling off of the polymer membrane 11 can be specifically seen only when the polymer membrane 11 is formed on the metallic membrane 13. In earlier, there was no method for manufacturing the biochip including the formation of the polymer membrane 11 as the protecting film on the metallic membrane 13. Especially, in the case where the polymer membrane 11 is composed of SU-8-3000 and the metallic membrane 13 is composed of Ti, favorable peel-off is obtained. Though the method including forming the plurality of biomaterial films 91a-91i after the silane coupling films 81a-81i are formed on the base plate 15 exposed from each of the plurality of wells 42a-42i, 43a-43i, 44a-44i, 45a-45i, 46a-46i, 47a-47i, 48a-48i, 49a-49i shown in FIG. 13 to FIG. 27 is explained, the probe biomolecules can be bonded to the plurality of hydroxyl groups (—OH) shown in FIG. 13 without using the silane coupling films 81a-81i.

(MODIFICATION OF THE SECOND EMBODIMENT)

It is possible to synthesize the probe DNAs having different base sequences in each of the plurality of wells 41a-41i, 42a-42i, 43a-43i, 44a-44i, 45a-45i, 46a-46i, 47a-47i, 48a-48i, 49a-49i, shown in FIG. 7. A method for synthesizing the probe DNAs having the different base sequences in each of the plurality of wells 41a-41i, 42a-42i, 43a-43i, 44a-44i, 45a-45i, 46a-46i, 47a-47i, 48a-48i, 49a-49i is described below.

Figure 28:
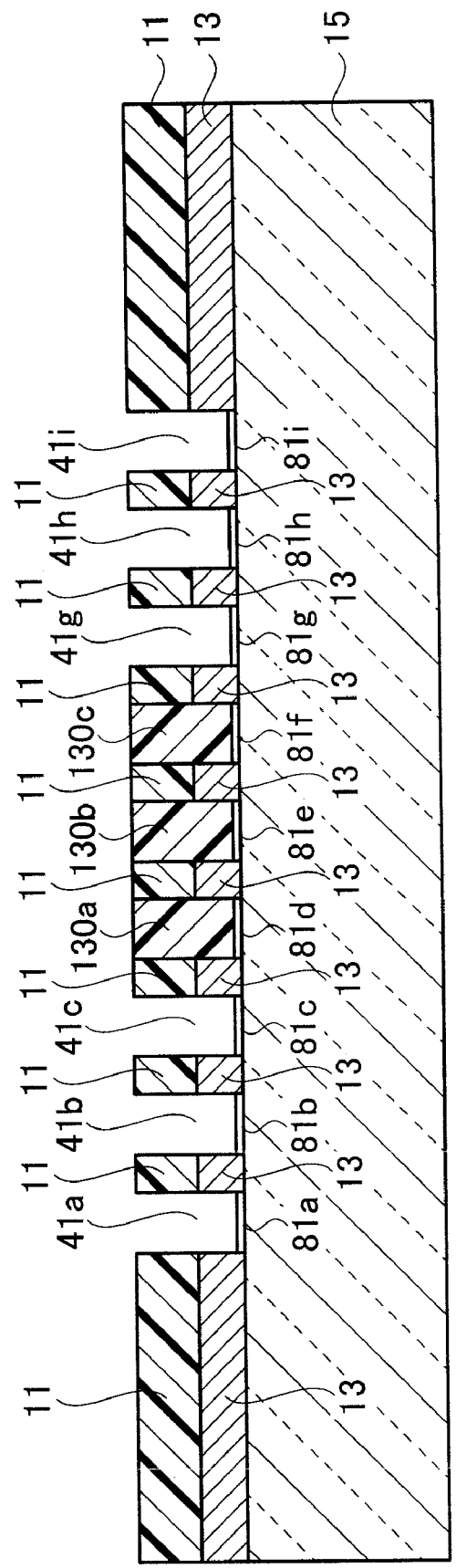
FIG. 28 shows a first sectional process drawing of the biochip according to a modification of the second embodiment of the present invention.

(a) As shown in FIG. 14, after each of the silane coupling films 81a-81i is formed, the epoxy groups of the silane coupling agents included in each of the silane coupling films 81a-81i are hydrolyzed and the hydroxyl groups (—OH) are introduced in each of the silane coupling films 81a-81i. Thereafter, the 5 bases of nucleosides having thymines (T) are bonded to the silane coupling agent in series. Next, as shown in FIG. 28, buried resins are embedded in the wells 41d, 41e, 41f to form block layer 130a, 130b, 130c. Polyhydroxy styrene (PHS) having 20,000 of average molecular weight dissolved in Dimethylsulfoxide (DMSO) at 5% of ratio by weight can be used as a material of the buried resin.

(b) Dimethoxytrityl (DMTr) groups of the nucleosides in each of the wells 41a, 41b, 41c, 41g, 41h, 41i where the buried resins were not embedded are deprotected by the 3% trichloroacetic acid/dichloromethane acid solution. Thereafter, the block layers 130a, 130b, 130c are removed by solvent. Next, new nucleosides of which 3' terminal hydroxyl groups are changed to trivalent phosphoramidite derivatives are dropped into the wells 41a-41i. The new nucleosides react and are bonded only to 5' hydroxyl groups (—OH) of the nucleosides of which Dimethoxytrityl (DMTr) groups were deprotected in the wells 41a, 41b, 41c, 41g, 41h, 41i.

Figure 29:
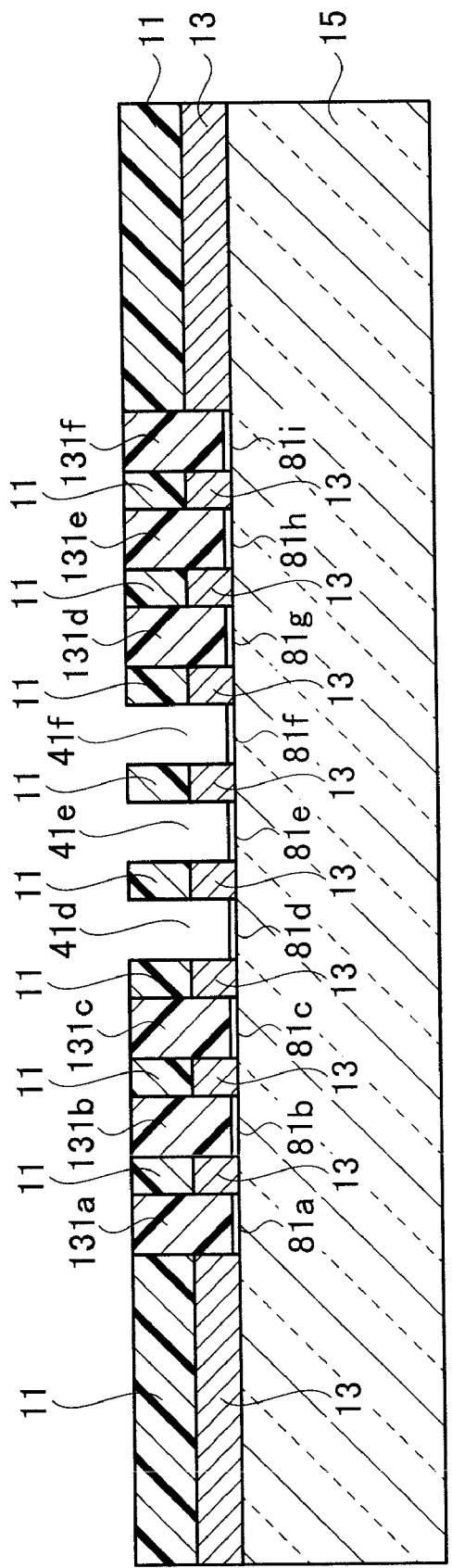
FIG. 29 shows a second sectional process drawing of the biochip according to the modification of the second embodiment of the present invention.

(c) The wells 41a, 41b, 41c, 41g, 41h, 41i shown in FIG. 14 are embedded with buried resins, as shown in FIG. 29, to form block layers 131a, 131b, 131c, 131d, 131e, 131f. Next, Dimethoxytrityl (DMTr) groups of the nucleosides in each of the wells 41d, 41e, 41f where the buried resins were not embedded are deprotected by the 3% trichloroacetic acid/dichloromethane acid solution. Then, the block layers 131a, 131b, 131c, 131d, 131e, 131f are removed by the solvent. Thereafter, new nucleosides of which 3' terminal hydroxyl groups are changed to trivalent phosphoramidite derivative are dropped in the wells 41a-41i. The new nucleosides react and are bonded to 5' hydroxyl groups (—OH) of nucleosides of which Dimethoxytrityl (DMTr) groups were deprotected in the wells 41d, 41e, 41f.

(d) Thereafter, embedding the buried resin in at least any one of the wells 41a-41i, deprotection of Dimethoxytrityl (DMTr) group, removal of the buried resin, and polymerization reaction of the nucleosides are repeated and the probe DNAs having the different base sequences in each of the plurality of wells 41a-41i, 42a-42i, 43a-43i, 44a-44i, 45a-45i, 46a-46i, 47a-47i, 48a-48i, 49a-49i are synthesized.

In the process of DNA synthesis shown in FIG. 28 and FIG. 29, it is possible to secure each depth of the plurality of wells 42a-49i, since the polymer membrane 11 is disposed on the metallic membrane 13. Therefore, it becomes easy to embed the buried resin in each of the plurality of wells 42a-49i.

(THIRD EMBODIMENT)

Figure 30:
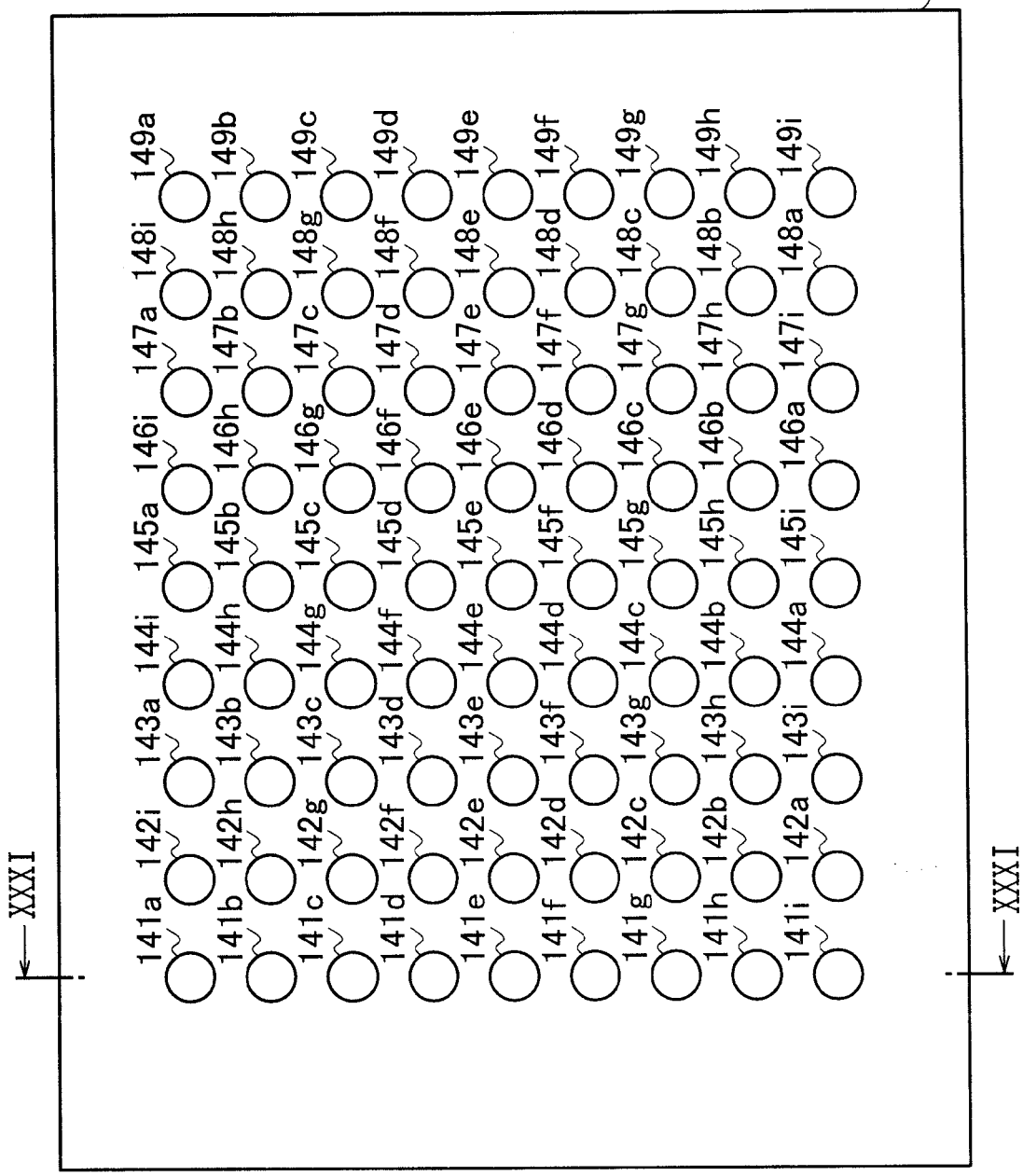
FIG. 30 shows a top view of the substrate for the biochip according to a third embodiment of the present invention.
Figure 31:
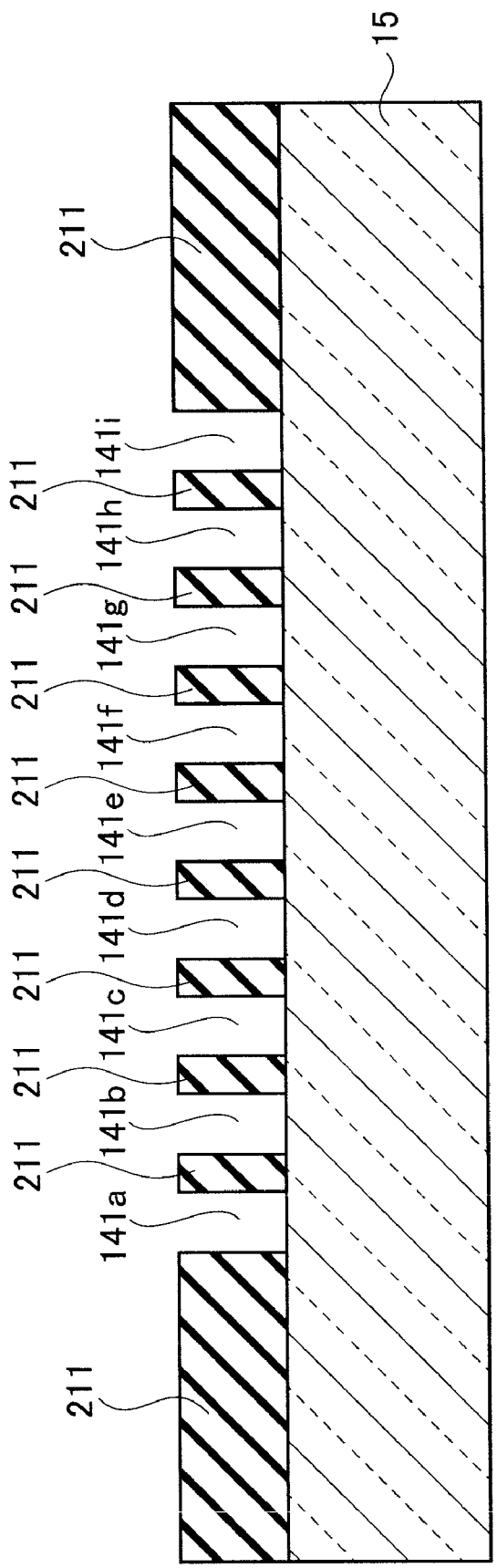
FIG. 31 shows a sectional view of the substrate for the biochip according to the third embodiment of the present invention.

With reference to FIG. 30 and FIG. 31 that is a sectional view taken on line XXXI-XXXI, a substrate for a biochip according to a third embodiment includes the base plate 15 having the surface on which the plurality of hydroxyl groups can be introduced, and a cover member 211 disposed on the base plate 15 when the probe biomolecules are bonded to the plurality of hydroxyl groups, and having a plurality of through holes 141a, 141b, 141c, 141d, 141e, 141f, 141g, 141h, 141i, 142a, 142b, 142c, 142d, 142e, 142f, 142g, 142h, 142i, 143a, 143b, 143c, 143d, 143e, 143f, 143g, 143h, 143i, 144a, 144b, 144c, 144d, 144e, 144f, 144g, 144h, 144i, 145a, 145b, 145c, 145d, 145e, 145f, 145g, 145h, 145i, 146a, 146b, 146c, 146d, 146e, 146f, 146g, 146h, 146i, 147a, 147b, 147c, 147d, 147e, 147f, 147g, 147h, 147i, 148a, 148b, 148c, 148d, 148e, 148f, 148g, 148h, 148i, 149a, 149b, 149c, 149d, 149e, 149f, 149g, 149h, 149i defining biding areas of the probe biomolecules on the surface of base plate 15.

During the probe biomolecules are introduced on the surface of the base plate 15 exposed from each of the plurality of through holes 141a-149i, the cover member 211 is close contact with the upper surface of base plate 15. A material having an anti peeling property against the nucleic acid synthetic agents such as the resin like SU-8, etc., silicon (Si) rubber, and Poly-dimethyl siloxane (PDMS) can be used as the material of the cover member 211. The method for introducing the probe biomolecules onto the surface of the base plate 15 is similar to the method explained with FIG. 15 to FIG. 25. Therefore, an explanation is omitted. After the probe biomolecules are introduced onto the base plate 15 exposed from each of the plurality of through holes 141a-149i, the cover member 211 is removed from the base plate 15. After the cover member 211 is removed from the base plate 15, the probe biomolecules are introduced only on the portions of the base plate 15 exposed form the plurality of through holes 141a-149i and the probe biomolecules are not introduced on other portions. Therefore, the target biomolecules are bonded to the portions of the base plate 15 exposed form the plurality of through holes 141a-149i and are not bonded to other portions. Consequently, in the process for detecting the target biomolecules, it is possible to cancel the background noise generated by the target biomolecules nonspecifically bonded to the surface of the base plate 15. It should be noted that the metallic membrane may be disposed between the base plate 15 and the cover member 211 as explained in the first and second embodiments.

(FOURTH EMBODIMENT)

Figure 32:
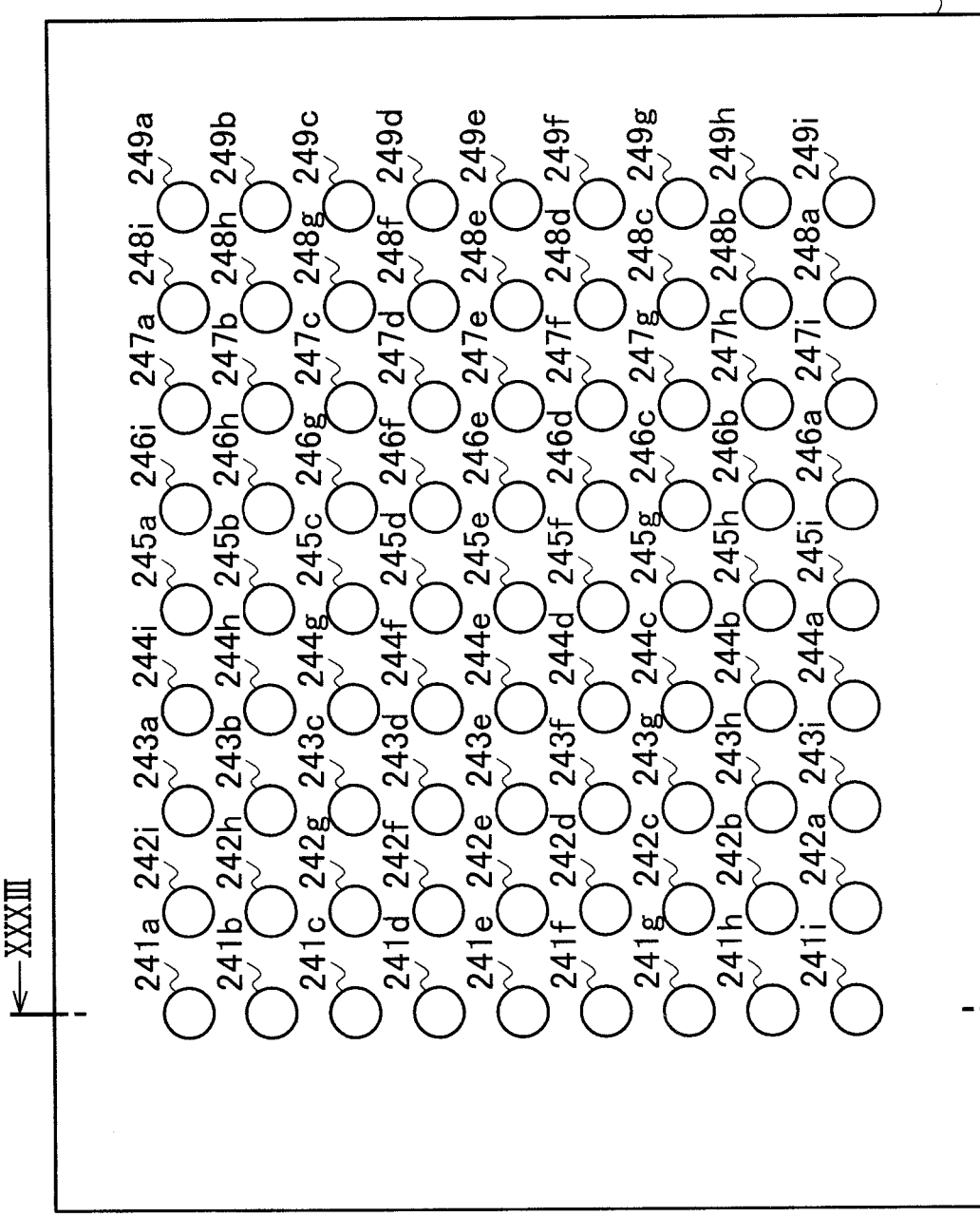
FIG. 32 shows a top view of the biochip according to a fourth embodiment of the present invention.
Figure 33:
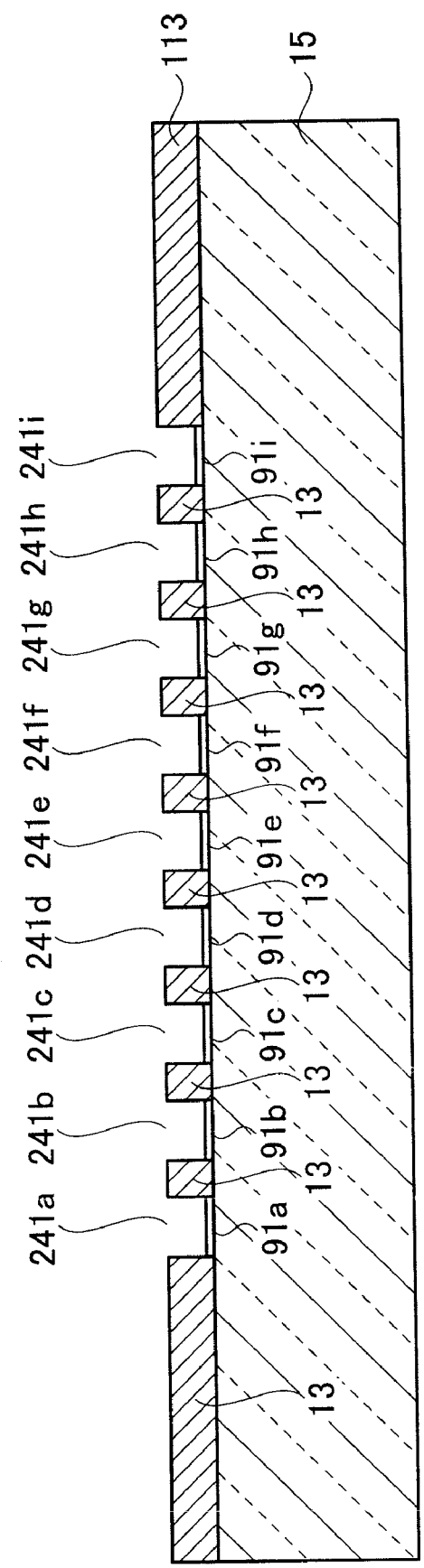
FIG. 33 shows a first sectional view of the biochip according to the fourth embodiment of the present invention.

With reference to FIG. 32 and FIG. 33 that is a sectional view taken on line XXXIII-XXXIII, a biochip according to a fourth embodiment of the present invention includes an optical transparency base plate 15 having a surface on which the plurality of hydroxyl groups (—OH) can be introduced, and a light shielding film 113 disposed on the base plate 15 and having a plurality of through holes 241a, 241b, 241c, 241d, 241e, 241f, 241g, 241h, 241i, 242a, 242b, 242c, 242d, 242e, 242f, 242g, 242h, 242i, 243a, 243b, 243c, 243d, 243e, 243f, 243g, 243h, 243i, 244a, 244b, 244c, 244d, 244e, 244f, 244g, 244h, 244i, 245a, 245b, 245c, 245d, 245e, 245f, 245g, 245h, 245i, 246a, 246b, 246c, 246d, 246e, 246f, 246g, 246h, 246i, 247a, 247b, 247c, 247d, 247e, 247f, 247g, 247h, 247i, 248a, 248b, 248c, 248d, 248e, 248f, 248g, 248h, 248i, 249a, 249b, 249c, 249d, 249e, 249f, 249g, 249h, 249i that reach the base plate 15. The transition metal such as Titan (Ti), platinum (Pt), chrome (Cr), niobium (Nb), tantalum (Ta), tungsten (W), etc., and the metal such as aluminum (Al), gold (Au), etc., can be used for the material of the light shielding film 113. In addition, the transition metallic oxide such as titanium monoxide (TiO), titanium dioxide ($TiO_2$), etc., and the transition metal nitride such as titanium nitride (TiN), etc., and the transition metal carbide such as titanium carbide (TiC), etc., can be used as the material of light shielding film 113, for example. Each diameter of the plurality of through holes 241a-249i is above 300 micrometers.

Further, as shown in FIG. 33, the biochip according to fourth embodiment includes a plurality of biomaterial films 91a, 91b, 91c, 91d, 91e, 91f, 91g, 91h, 91i disposed on the surface of the base plate 15 exposed from the plurality of through holes 241a-241i, respectively. In each of the plurality of biomaterial films 91a-91i, each functional group of the plurality of probe biomolecules such as the plurality of DNAs, the plurality of RNAs, the plurality of PNAs, the plurality of proteins, etc., is covalently bonded to the hydroxyl group (—OH) on the surface of the base plate 15, as explained with FIG. 9.

It should be noted that the fourth embodiment is not limited to the displacement where the plurality of biomaterial films 91a-91i directly displaced on the surface of the base plate 15, respectively. In a case shown in FIG. 34, silane coupling films 81a, 81b, 81c, 81d, 81e, 81f, 81g, 81h, 81i are disposed on the surface of the portions of the base plate 15 exposed from the plurality of through holes 241a-241i, respectively. In each of the silane coupling films 81a-81i, as explained with FIG. 11, each methyl group (—$CH_3$) or each ethyl group (—$C_2H_5$) of the plurality of silane coupling agents is chemically bonded to the hydroxyl group (—OH) on the surface of the base plate 15 by the acid-base reaction. Alternatively, the silane coupling agent and the probe biomolecule may be coupled via the cross linker. Here, each sectional view of the plurality of through holes 242a-242i, 243a-243i, 244a-244i, 245a-245i, 246a-246i, 247a-247i, 248a-248i, 249a-249i shown in FIG. 32 is similar to FIG. 33, so an explanation is omitted.

Figure 34:
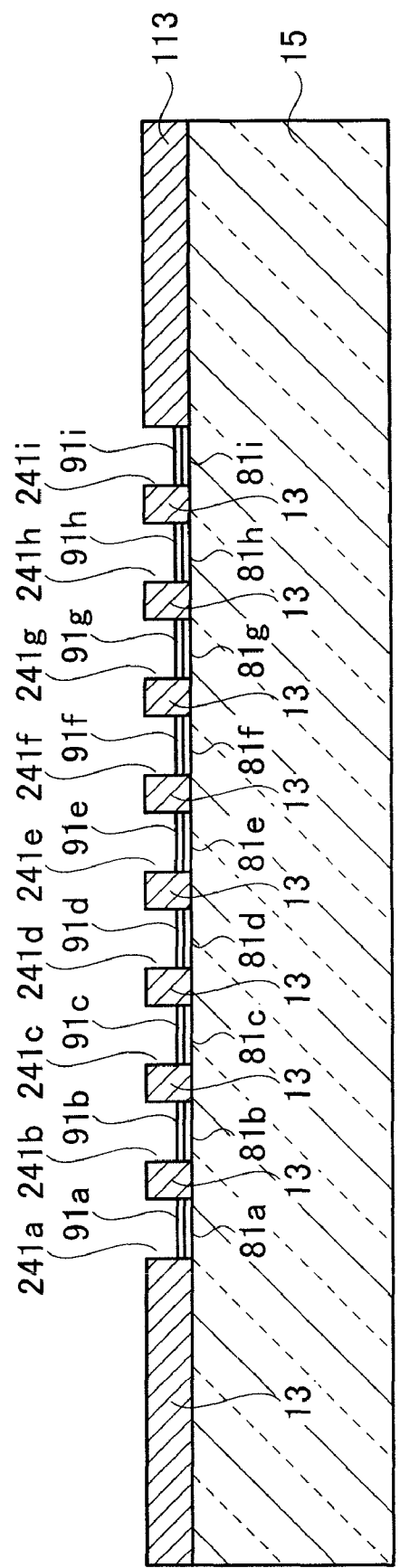
FIG. 34 shows a second sectional view of the biochip according to the fourth embodiment of the present invention.

As described above, in the biochip according to the fourth embodiment shown in FIG. 32 to FIG. 34, each of the plurality of biomaterial films 91a-91i is disposed on the optical transparency base plate 15 like a spot. Further, the light shielding film 113 is disposed around each of the plurality of biomaterial films 91a-91i. When an assay is performed with the biochip according to the fourth embodiment, the target biomolecules labeled with biotins are dropped into the plurality of biomaterial films 91a-91i, respectively. After the biochip is left for the time period required for interactions between the target biomolecules and the probe biomolecules, the biochip is washed to remove the unreacted target biomolecules. Then, a solution including streptavidins labeled with Horseradish Peroxidase (HRP) is dropped into each of the plurality of biomaterial films 91a-91i. After it is stilly left for 1 hour at room temperature, the biochip is washed to remove the unreacted streptavidin. After the washing, a solution including Tetramethyl benzidine (TMB) is dropped into each of the plurality of biomaterial films 91a-91i. When the target biomolecules are trapped in each of the plurality of biomaterial films 91a-91i, colors of TMB come out by the HRP of target biomolecule. Therefore, by emitting illuminating light from the back side opposite to the surface of the base plate 15 displaced with the light shielding film 113, it is possible to easily confirm whether the chromogenic reaction occurs in each of the plurality of biomaterial films 91a-91i by the transmitted light through the base plate 15, since the light shielding film 113 enhances the contrast. In addition, by setting each diameter of the plurality of through holes 241a-249i above 300 micrometers, it is possible to confirm whether the chromogenic reaction occurs in each of the plurality of biomaterial films 91a-91i by the naked eye.

Next, with reference to FIG. 35 to FIG. 40, the method for manufacturing the biochip according to fourth embodiment is described.

Figure 35:
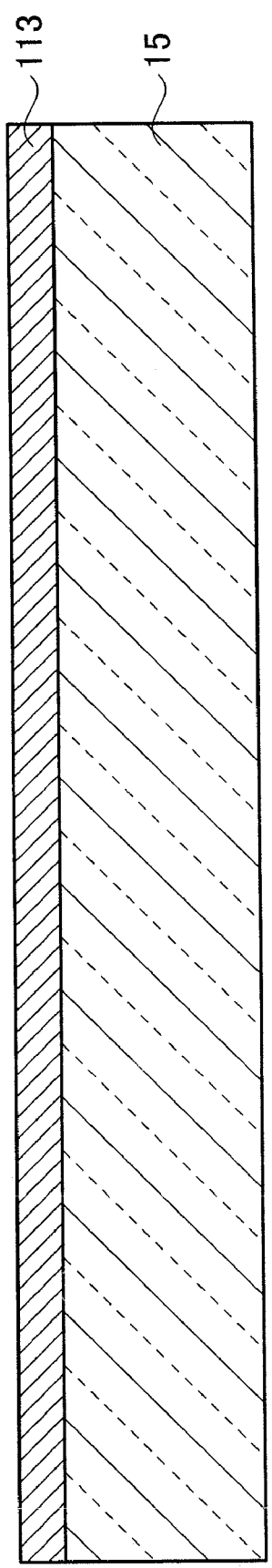
FIG. 35 shows a first sectional process drawing of the biochip according to the fourth embodiment of the present invention.
Figure 36:
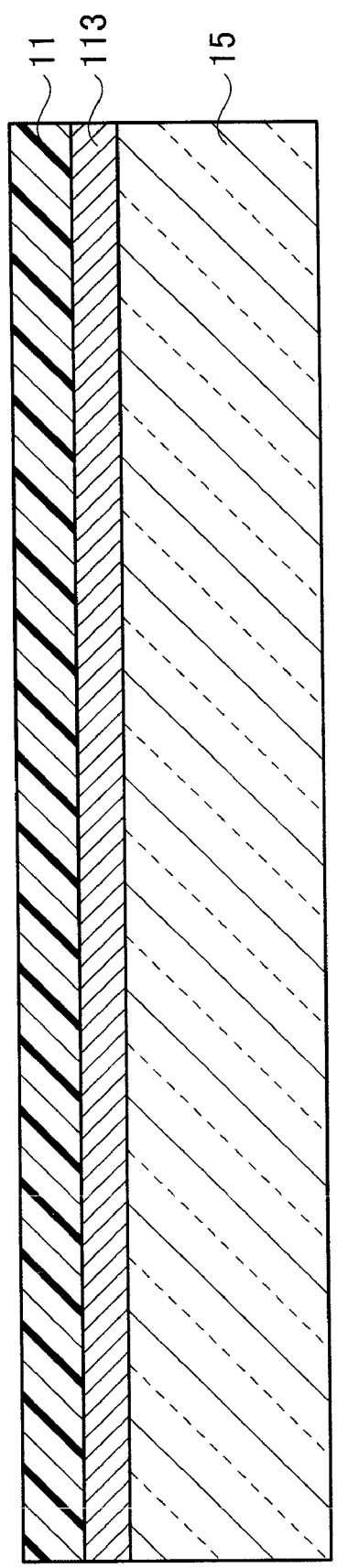
FIG. 36 shows a second sectional process drawing of the biochip according to the fourth embodiment of the present invention.
Figure 37:
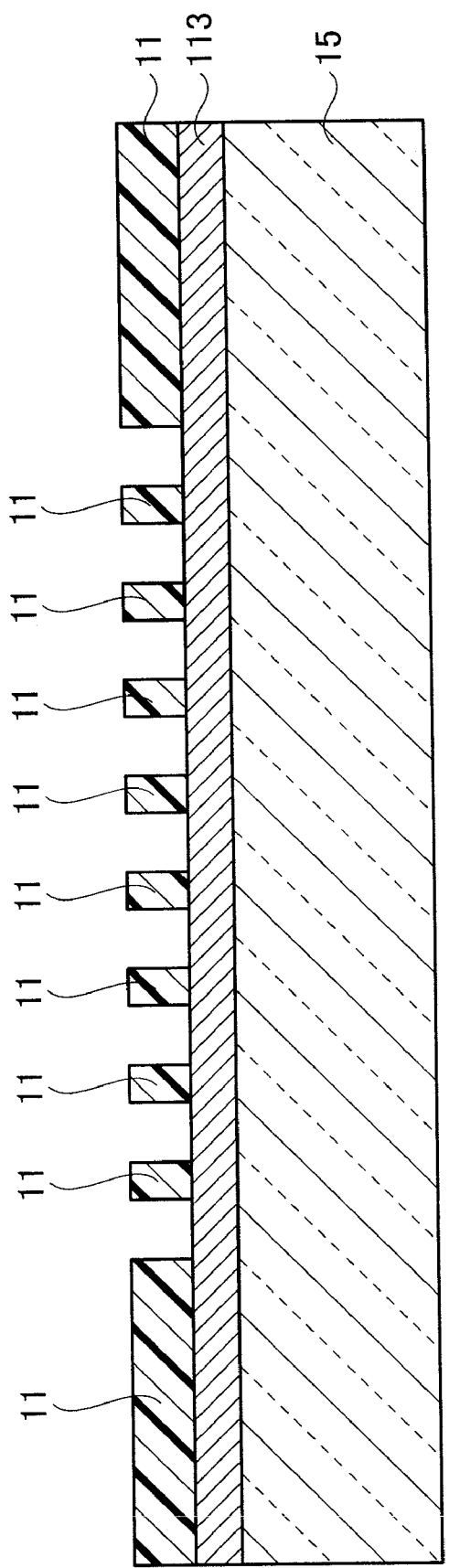
FIG. 37 shows a third sectional process drawing of the biochip according to the fourth embodiment of the present invention.

(a) As shown in FIG. 35, the base plate 15 composed of $SiO_2$, for example, is prepared and the light shielding film 113 composed of Ti, for example, is formed on the base plate 15 by using the sputtering method or the CVD method, for example. After the light shielding film 113 is formed, the surface is treated with $O_2$ plasma for 5 minutes. Next, as shown in FIG. 36, the solution including the photosensitive epoxy resin such as SU-8-3000 series is spin-coated on the light shielding film 113 to form the polymer membrane 11. After the polymer membrane 11 is formed, prebake is performed for the polymer membrane 11. Thereafter, by using a photomask having a mask pattern corresponding to each shape of the plurality of through holes 241a-241i, 242a-242i, 243a-243i, 244a-244i, 245a-245i, 246a-246i, 247a-247i, 248a-248i, 249a-249i shown in FIG. 32, portions of the polymer membrane 11 are selectively exposed to the ultraviolet rays. After the exposure, the PEB process is performed for the polymer membrane 11. Thereafter, the polymer membrane 11 is developed with SU-8 developer solution, for example, to selectively remove the portions of the polymer membrane 11, as shown in FIG. 37.

Figure 38:
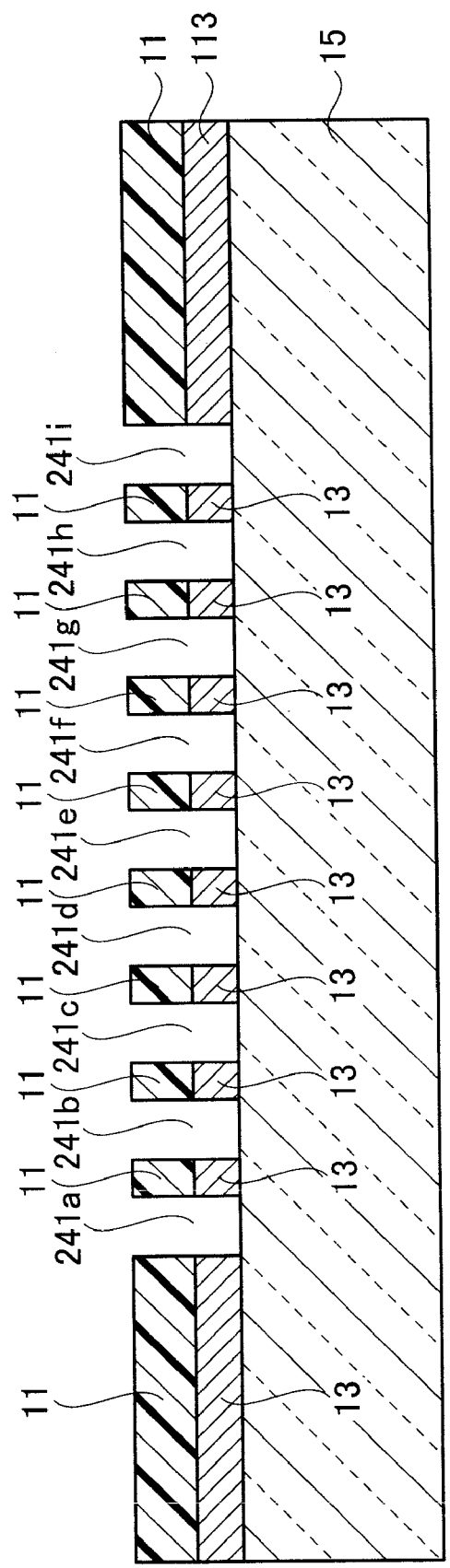
FIG. 38 shows a fourth sectional process drawing of the biochip according to the fourth embodiment of the present invention.

(b) By using the polymer membrane 11 of which the portions are selectively removed as an etching mask, portions of the light shielding film 113 are selectively removed by isotropic wet etching. By the selective removal, each of the plurality of through holes 241a-241i, 242a-242i, 243a-243i, 244a-244i, 245a-245i, 246a-246i, 247a-247i, 248a-248i, 249a-249i is formed as shown in FIG. 38. Then, the base plate 15 is left in the stirred sodium hydroxide (NaOH) solution at room temperature for 2 hours and the plurality of hydroxyl groups (—OH) are introduced on the surface of the base plate 15 exposed from each of the through holes 241a-241i, as explained with FIG. 13.

Figure 39:
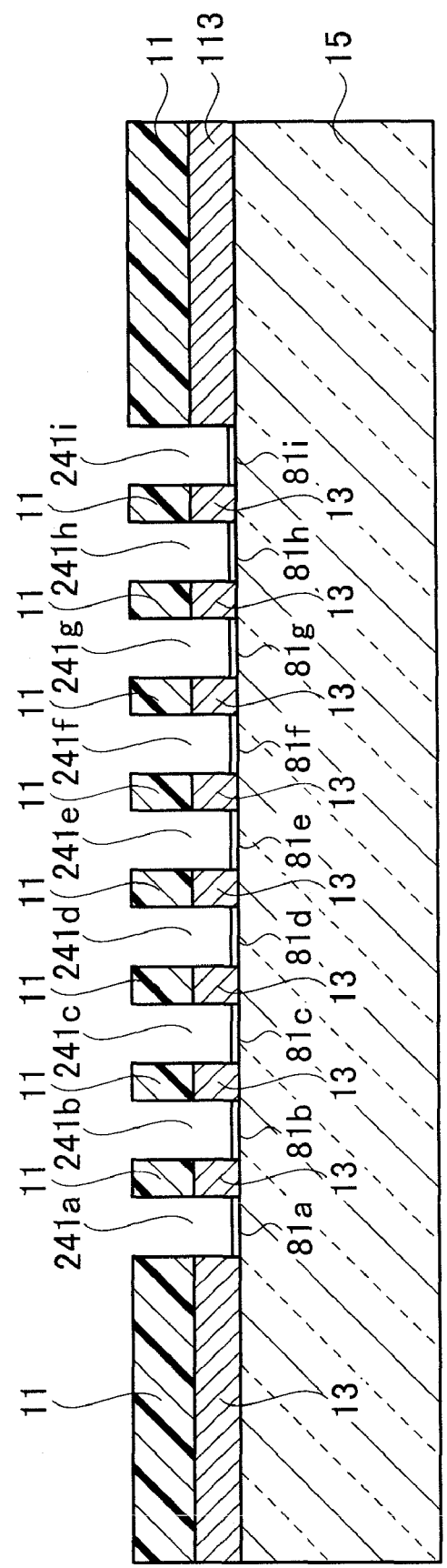
FIG. 39 shows a fifth sectional process drawing of the biochip according to the fourth embodiment of the present invention.

(c) For example, the silane coupling reagent of which functional group has amine is dropped onto the surface of the base plate 15 exposed from each of the through holes 241a-241i, shown in FIG. 38, to form each of the silane coupling films 81a, 81b, 81c, 81d, 81e, 81f, 81g, 81h, 81i shown in FIG. 39. When the silane coupling agent having the epoxy group is dropped under 15 degrees C. condition, for example, the plurality of epoxy groups are introduced on the surface of the base plate 15, as explained with FIG. 15. It should be noted that the locations of the through holes 241a-241i can be easily identified when the silane coupling agent is dropped, because of the contrast between the optical transparency base plate 15 and the light shielding film 113 shown in FIG. 39.

Figure 40:
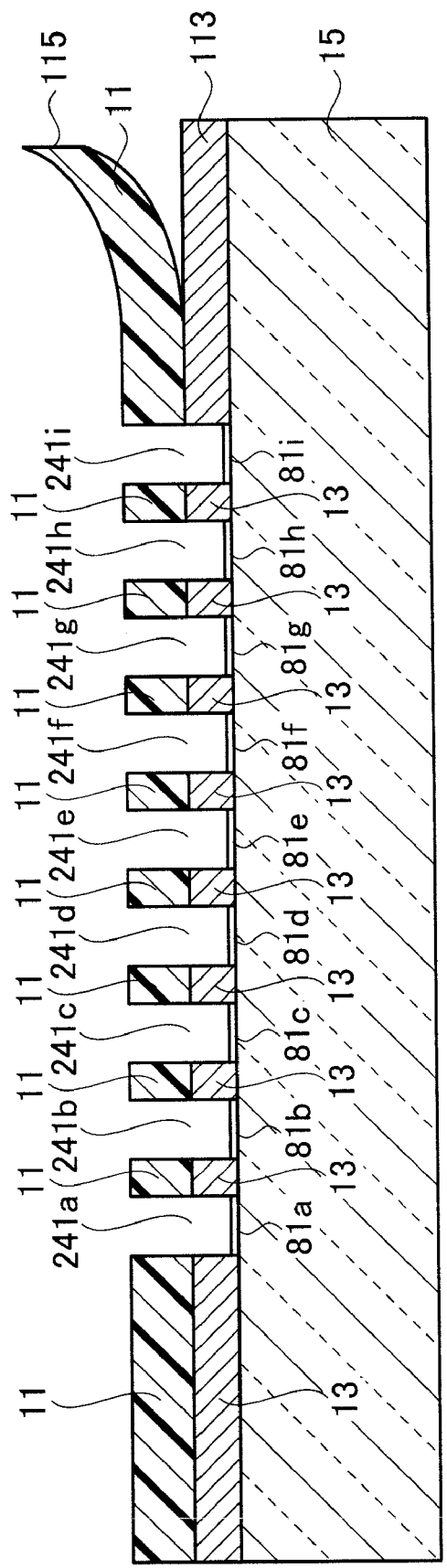
FIG. 40 shows a sixth sectional process drawing of the biochip according to the fourth embodiment of the present invention.

(d) The unreacted hydroxyl groups (—OH) remaining on the surface of the base plate 15 are acetylated to be capped. Next, as explained with FIG. 16, the epoxy groups of the silane coupling agents introduced onto the surface of the base plate 15 are hydrolyzed to introduce the hydroxyl groups (—OH) in each of the silane coupling films 81a-81i. Thereafter, by the method similar to the explanation of FIG. 17 to FIG. 23, the plurality of biomaterial films 91a-91i shown in FIG. 34 are formed. The base plate 15 is sunk in the alkaline solution so that the polymer membrane 11 is soaking. As explained with FIG. 24, the cyanoethyl protecting groups bonded to the phosphate group are detached. Also, the bases such as adenine (A), cytosine (C), guanine (G), etc., are deprotected, as explained with FIG. 25. In addition, by the treatment with the alkaline solution, adhesive strength between the light shielding film 113 and the polymer membrane 11 is decreased. Thereafter, the base plate 15 is took out from the NH$_4$OH solution. And, the lateral side 115 of the polymer membrane 11 shown in FIG. 40 is blown by gas such as air by using the air gun, for example, to peel off the polymer membrane 11 from the light shielding film 113. Finally, the terminal Dimethoxytrityl (DMTr) groups are deprotected, as explained with FIG. 27 and the method for manufacturing the biochip according to the fourth embodiment is completed.

Figure 41:
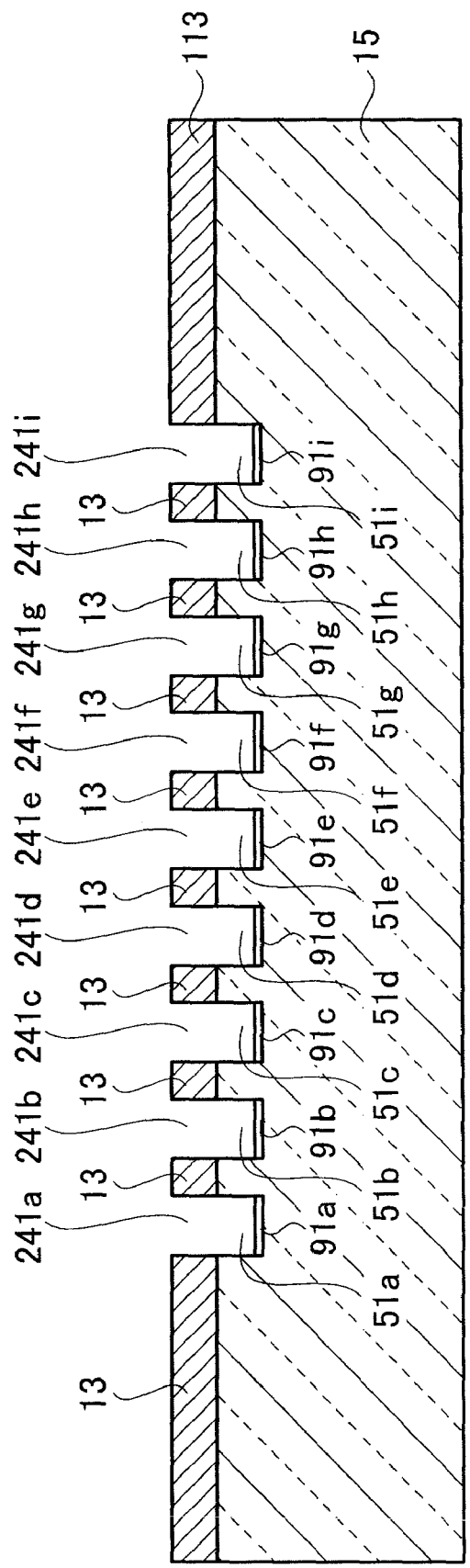
FIG. 41 shows a third sectional view of the biochip according to the fourth embodiment of the present invention.

It should be noted that the method for manufacturing the biochip according to the fourth embodiment is not limited to this. For example, it is explained that the light shielding film is formed on the base plate 15 shown in FIG. 35 by using the sputtering method or the CVD method. However, the light shielding film 113 having the plurality of through holes 241a-249i may be formed on the base plate 15, by using UV-curable black screen printing ink, for example. Alternatively, the light shielding film 113 having the through holes 241a-249i may be prepared in advance, and it may be pasted on the base plate 15 by a bonding agent, for example. Again, the material of the light shielding film 113 is not limited to metals. Resins or insoluble papers also can be used, for example. In addition, the light shielding film may be formed by using an ink-jet printer, for example. Also, as shown in FIG. 41, the base plate 15 of the biochip according to the fourth embodiment may have a plurality of wells 51a, 51b, 51c, 51d, 51e, 51f, 51g, 51h, 51i that open to the plurality of through holes 241a-241i of the light shielding film 113, respectively. The plurality of biomaterial films 91a-91i are disposed at each bottom of the plurality of wells 51a-51i. When the biochip shown in FIG. 41 is manufactured, the plurality of through holes 241a-241i are formed in the light shielding film 113, as shown in FIG. 38, and then, the base plate 15 may be selectively removed by the dry etching method by using the light shielding film 113 as the etching mask, for example. In the case where it is desired to secure the volume of the specimen solution, for example, the plurality of wells 51a-51i are formed.

(MODIFICATION OF THE FOURTH EMBODIMENT)

It is possible to synthesize the probe DNAs having the different base sequences on the surface of the base plate 15, shown in FIG. 32, exposed from the plurality of through holes 241a-241i, 242a-242i, 243a-243i, 244a-244i, 245a-245i, 246a-246i, 247a-247i, 248a-248i, 249a-249i, respectively. A method for synthesizing the probe DNAs having the different base sequences in the plurality of through holes 241a-241i, 242a-242i, 243a-243i, 244a-244i, 245a-245i, 246a-246i, 247a-247i, 248a-248i, 249a-249i, respectively, is described below.

Figure 42:
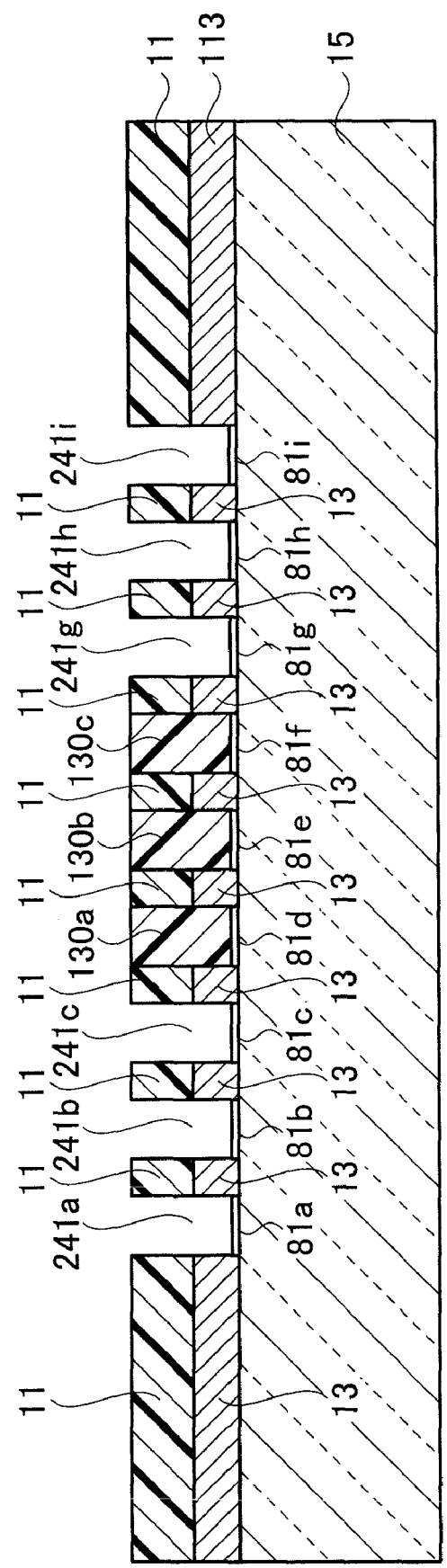
FIG. 42 shows a first sectional process drawing of the biochip according to a modification of the fourth embodiment of the present invention.

(a) As shown in FIG. 39, after each of the silane coupling films 81a-81i is formed, the epoxy groups of the silane coupling agents included in each of the silane coupling films 81a-81i are hydrolyzed to introduce the hydroxyl groups (—OH) in each of the silane coupling films 81a-81i. Thereafter, the 5 bases of nucleosides having thymines (T) are bonded to the silane coupling agent in series. Next, the buried resins are embedded into the through holes 241d, 241e, 241f, as shown in FIG. 42, to form the block layers 130a, 130b, 130c.

(b) Dimethoxytrityl (DMTr) groups of the nucleosides in each of the through holes 241a, 241b, 241c, 241g, 241h, 241i where the buried resins were not embedded are deprotected by the 3% trichloroacetic acid/dichloromethane acid solution. Thereafter, the block layers 130a, 130b, 130c are removed by the solvent. Next, new nucleosides of which 3' terminal hydroxyl groups are changed to the trivalent phosphoramidite derivatives are dropped into the through holes 241a-241i, and the new nucleosides only react and are bonded to the 5' hydroxyl groups (—OH) of the nucleosides of which Dimethoxytrityl (DMTr) groups were deprotected.

Figure 43:
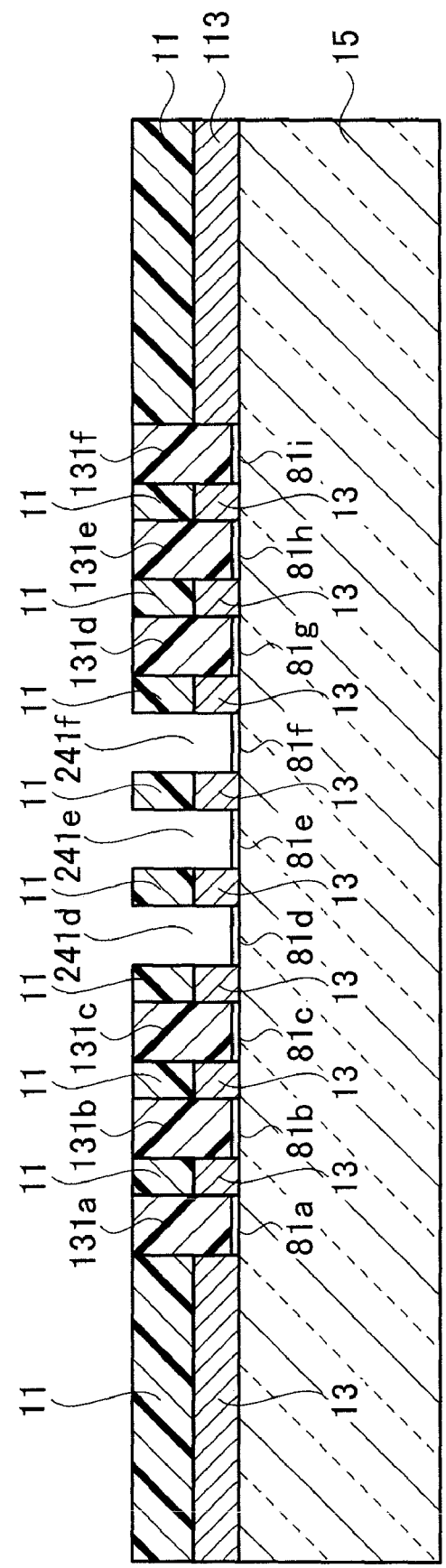
FIG. 43 shows a second sectional process drawing of the biochip according to the modification of the fourth embodiment of the present invention.

(c) As shown in FIG. 43, the buried resins are embedded in the through hole 241a, 241b, 241c, 241g, 241h, 241i shown in FIG. 39 to form the block layers 131a, 131b, 131c, 131d, 131e, 131f. Next, Dimethoxytrityl (DMTr) groups of the nucleosides in each of the through holes 241d, 241e, 241f where the buried resins were not embedded are deprotected by the 3% trichloroacetic acid/dichloromethane acid solution, and the block layers 131a, 131b, 131c, 131d, 131e, 131f are removed by the solvent. Thereafter, when new nucleosides of which 3' terminal hydroxyl groups were changed to the trivalent phosphoramidite derivatives are dropped in the through holes 241a-241i, the new nucleosides only react and are bonded to the 5' hydroxyl groups (—OH) of the nucleosides of which Dimethoxytrityl (DMTr) groups were deprotected in the through holes 241d, 241e, 241f.

(d) Thereafter, embedding the buried resin in any of the through holes 241a-241i, deprotection of the Dimethoxytrityl (DMTr) group, removal of the buried resins, and polymerization reaction of the nucleosides are repeated, and the probe DNAs having the different base sequences in the plurality of through holes 241a-241i, 242a-242i, 243a-243i, 244a-244i, 245a-245i, 246a-246i, 247a-247i, 248a-248i, 249a-249i are synthesized.

(FIFTH EMBODIMENT)

Figure 12:
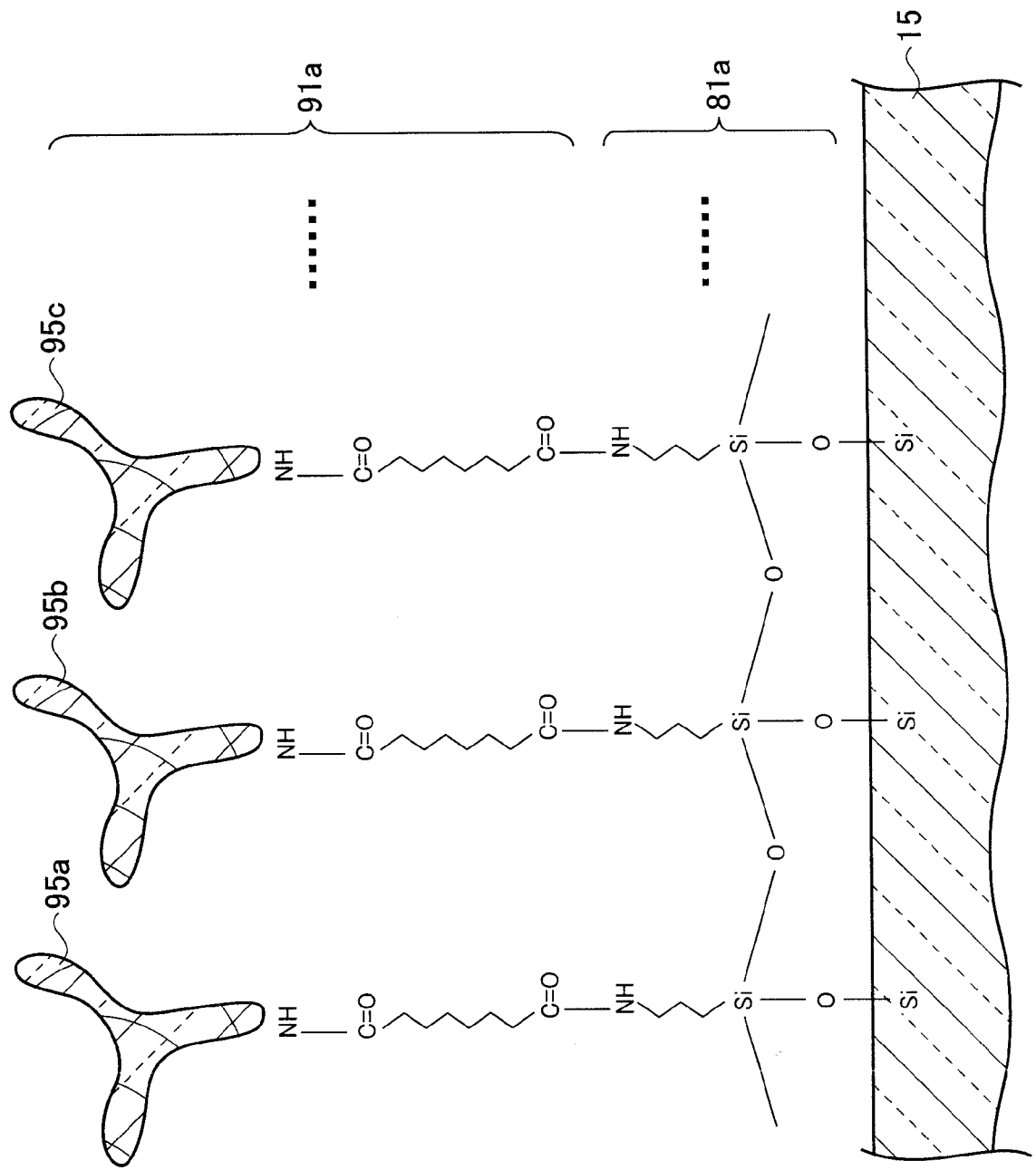
FIG. 12 shows a third enlarged sectional view of the biochip according to the second embodiment of the present invention.
Figure 44:
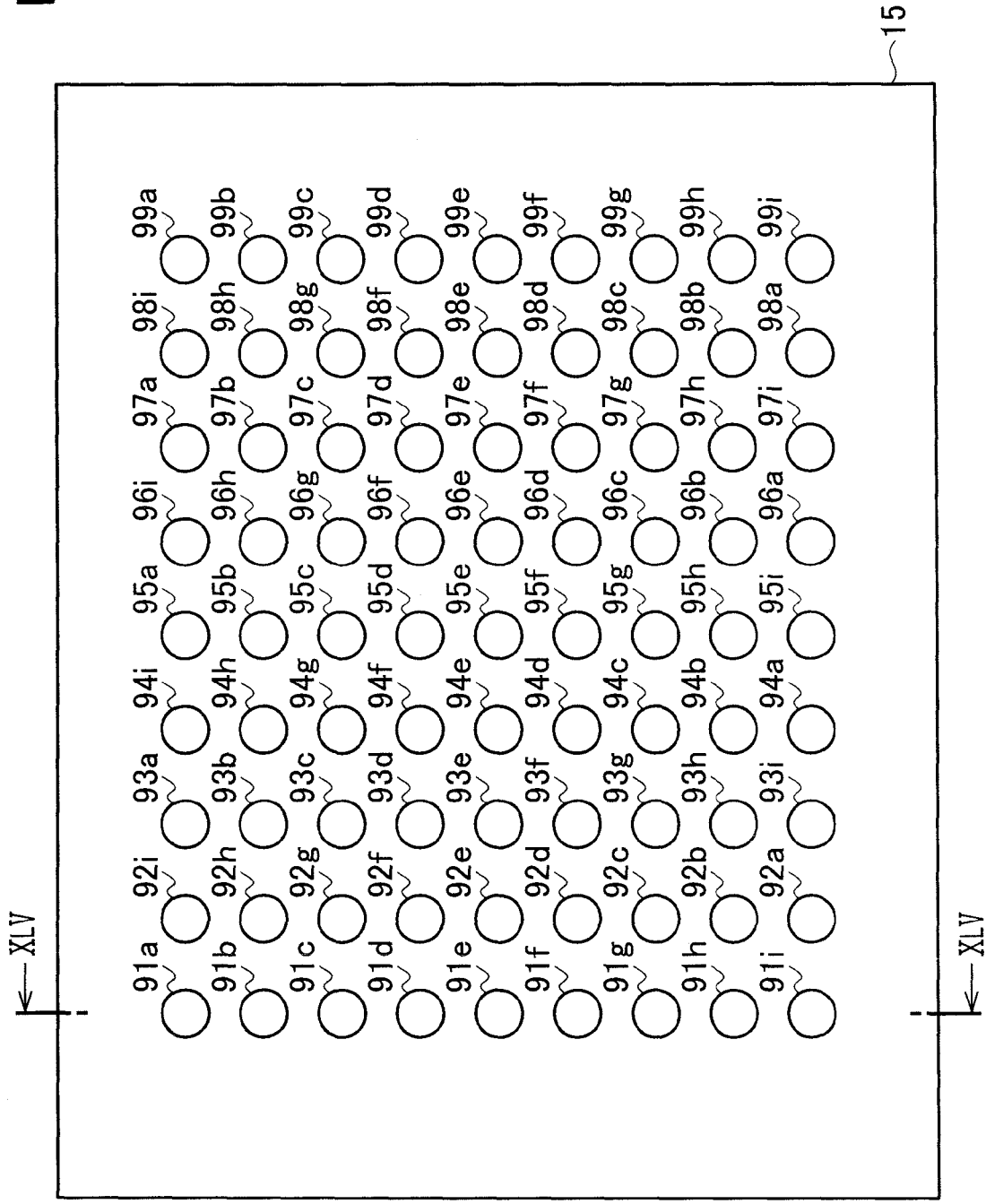
FIG. 44 shows a top view of the biochip according to a fifth embodiment of the present invention.
Figure 45:
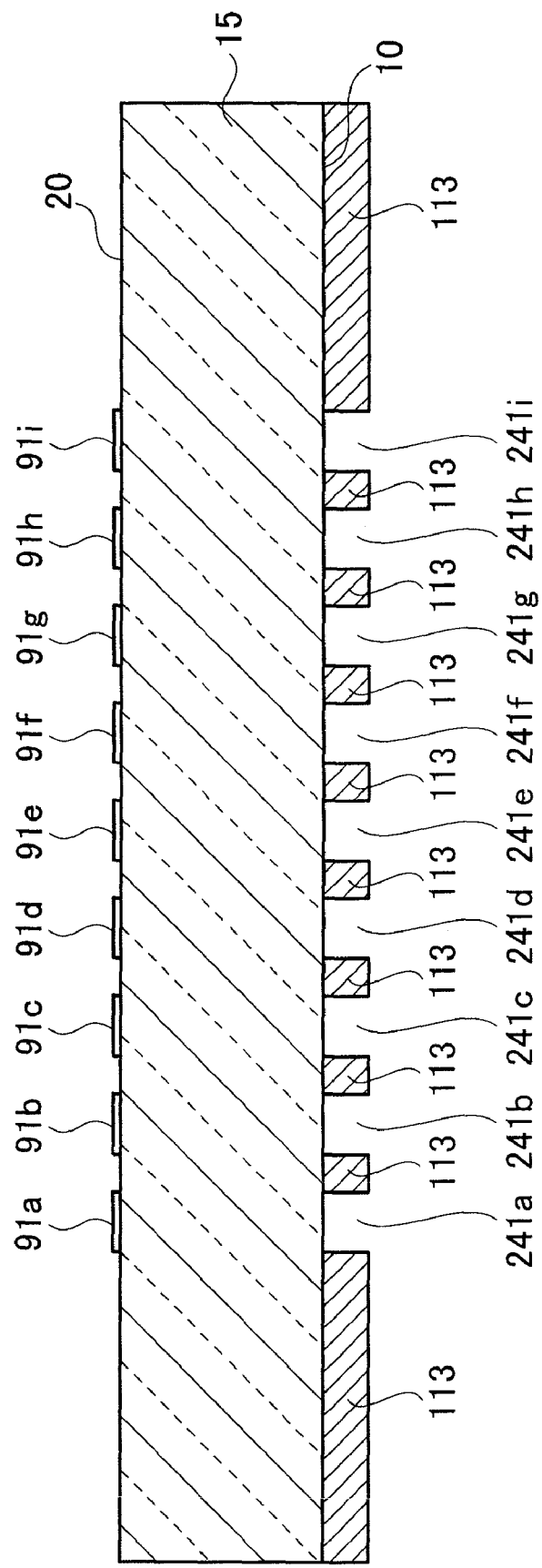
FIG. 45 shows a first sectional view of the biochip according to the fifth embodiment of the present invention.

With reference to FIG. 44 and FIG. 45 that is a sectional view taken on line XLV-XLV, a biochip according to a fifth embodiment includes an optical transparency base plate 15, a light shielding film 113 disposed on a first surface 10 of the base plate 15 and having a plurality of through holes 241a, 241b, 241c, 241d, 241e, 241f, 241g, 241h, 241i that reach the first surface 10, and a plurality of biomaterial films 91a, 91b, 91c, 91d, 91e, 91f, 91g, 91h, 91i, 92a, 92b, 92c, 92d, 92e, 92f, 92g, 92h, 92i, 93a, 93b, 93c, 93d, 93e, 93f, 93g, 93h, 93i, 94a, 94b, 94c, 94d, 94e, 94f, 94g, 94h, 94i, 95a, 95b, 95c, 95d, 95e, 95f, 95g, 95h, 95i, 96a, 96b, 96c, 96d, 96e, 96f, 96g, 96h, 96i, 97a, 97b, 97c, 97d, 97e, 97f, 97g, 97h, 97i, 98a, 98b, 98c, 98d, 98e, 98f, 98g, 98h, 98i, 99a, 99b, 99c, 99d, 99e, 99f, 99g, 99h, 99i having a plurality of probe biomolecules, respectively, that are bonded to a second surface 20 of the base plate 15 opposite to the first surface 10 of the base plate 15. Each enlarged sectional view of the plurality of biomaterial films 91a-99i is similar to FIG. 9, so an explanation is omitted. Also, as shown in FIG. 11 and FIG. 12, the plurality of probe biomolecules may be bonded to the base plate 15 via the silane coupling agent or the cross linking agent, for example. After a specimen solution including the biotin labeled target biomolecules is dropped into each of the plurality of biomaterial films 91a-99i shown in FIG. 44 and FIG. 45, a solution including HRP labeled streptavidin is dropped into each of the plurality of biomaterial films 91a-99i. After it is stilly left and washed, a solution including TMP is dropped into each of the plurality of biomaterial films 91a-91i. Here, if the target biomolecules are trapped in each of the plurality of biomaterial films 91a-91i, the colors of TMB come out by the HRP of the target biomolecule. Therefore, when the illuminating light is emitted from the first surface 10, it is possible to easily confirm whether the chromogenic reaction occurs by the transmitted light incident on the base plate 15 from the through holes 241a-241i.

Figure 46:
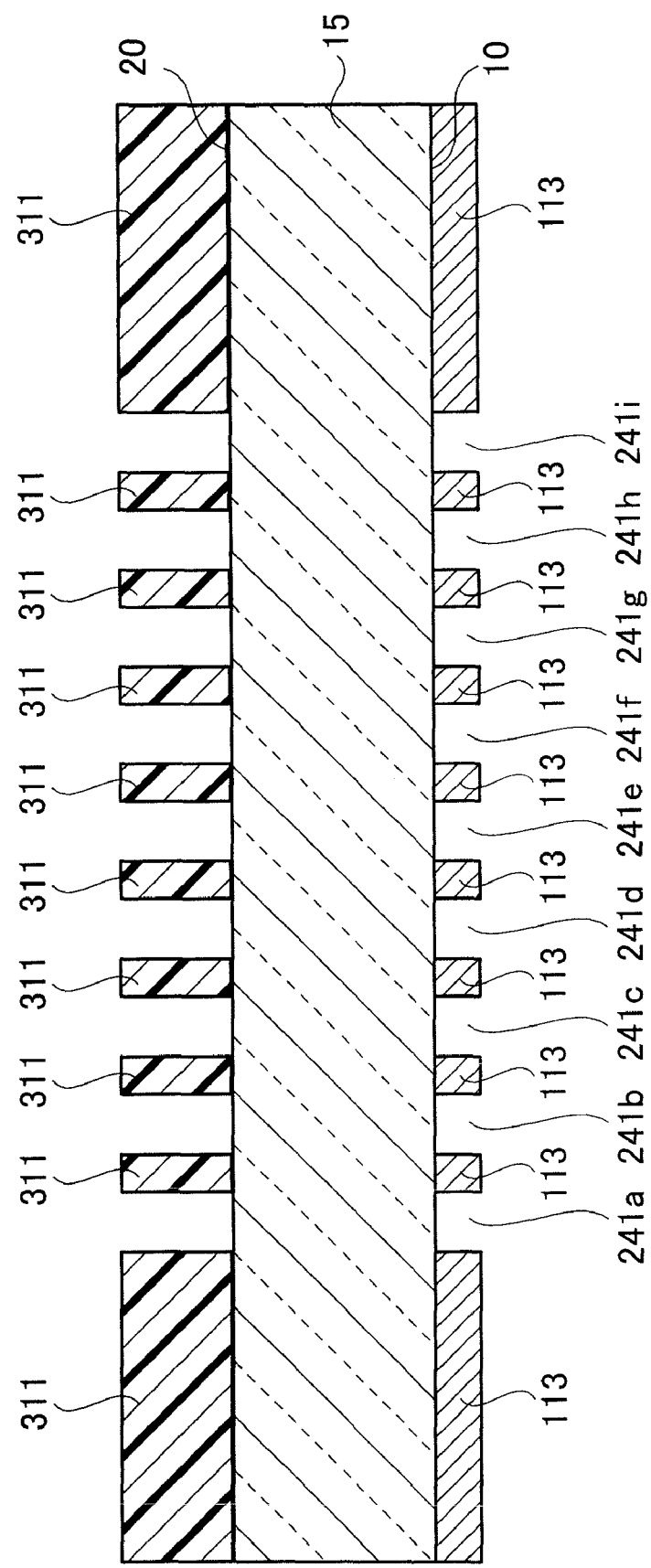
FIG. 46 shows a first sectional process drawing of the biochip according to the fifth embodiment of the present invention.
Figure 47:
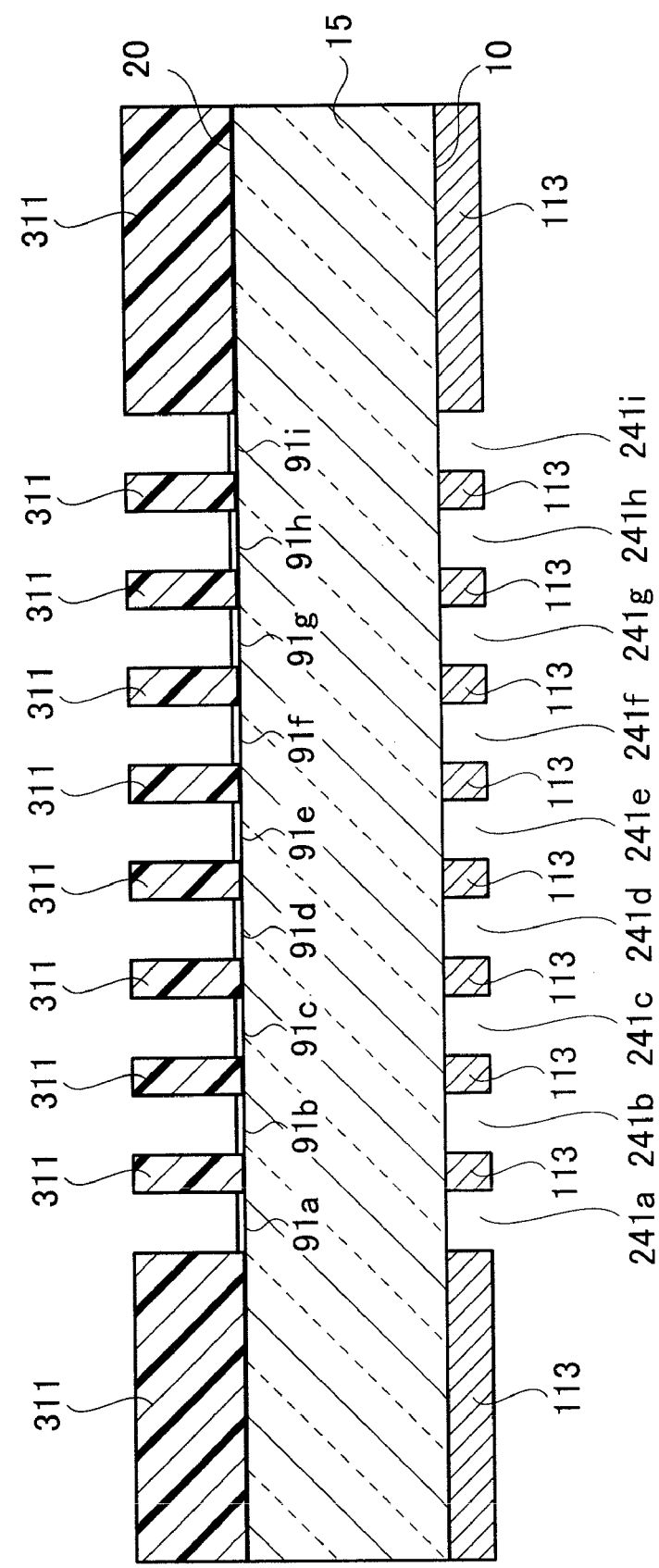
FIG. 47 shows a second sectional process drawing of the biochip according to the fifth embodiment of the present invention.

Next, a method for manufacturing the biochip according to the fifth embodiment is described. By using the method explained with FIG. 35 to FIG. 38, the light shielding film 113 having the plurality of through holes 241a-241i are formed on the first surface 10 of the base plate 15. In FIG. 46, a polymer membrane 311 having a plurality of openings is formed on the second surface of the base plate 15, by using a lithography method, for example. Here, locations of the plurality of formed openings of the polymer membrane 311 confront locations of the plurality of formed through holes 241a-241i of the light shielding film 113, respectively. In FIG. 47, the plurality of biomaterial films 91a-91i are formed on the second surface 20 of the base plate 15 exposed from the plurality of openings of the polymer membrane 311, respectively. Thereafter, the polymer membrane 311 is peeled off from the second surface 20 and the biochip according to the fifth embodiment is achieved.

Figure 48:
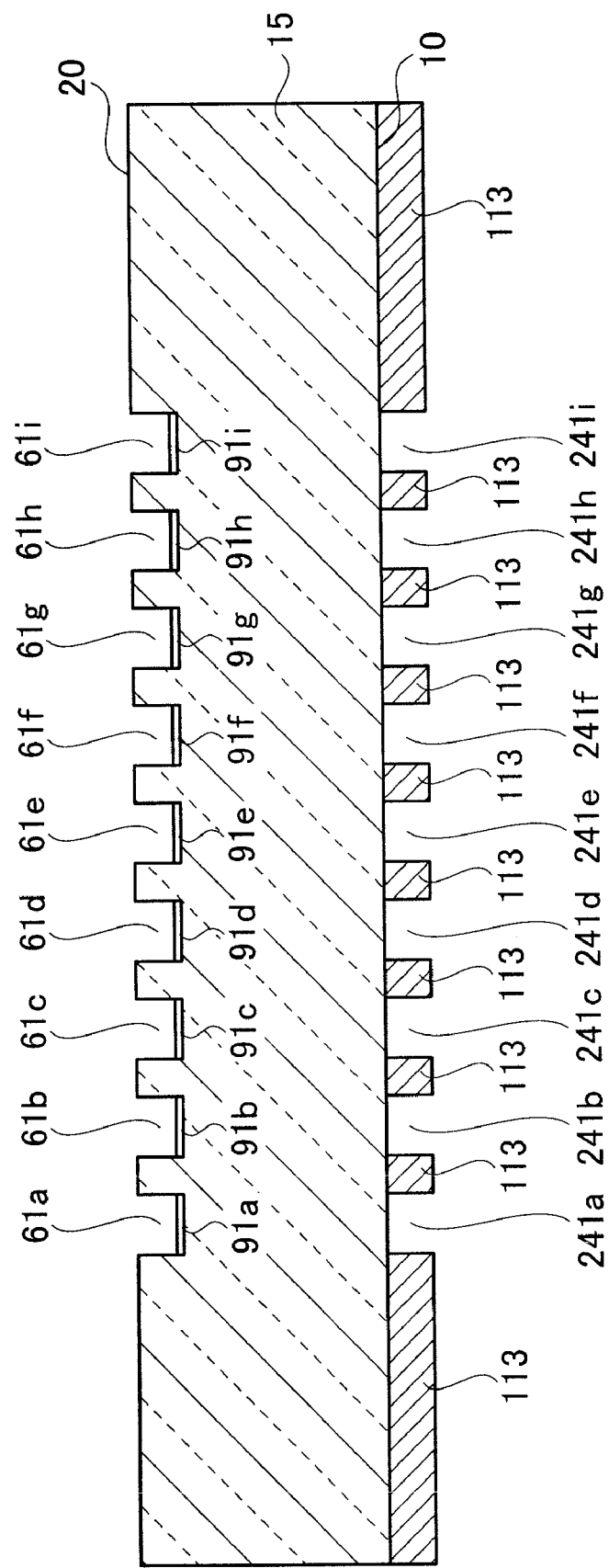
FIG. 48 shows a second sectional view of the biochip according to the fifth embodiment of the present invention.
Figure 49:
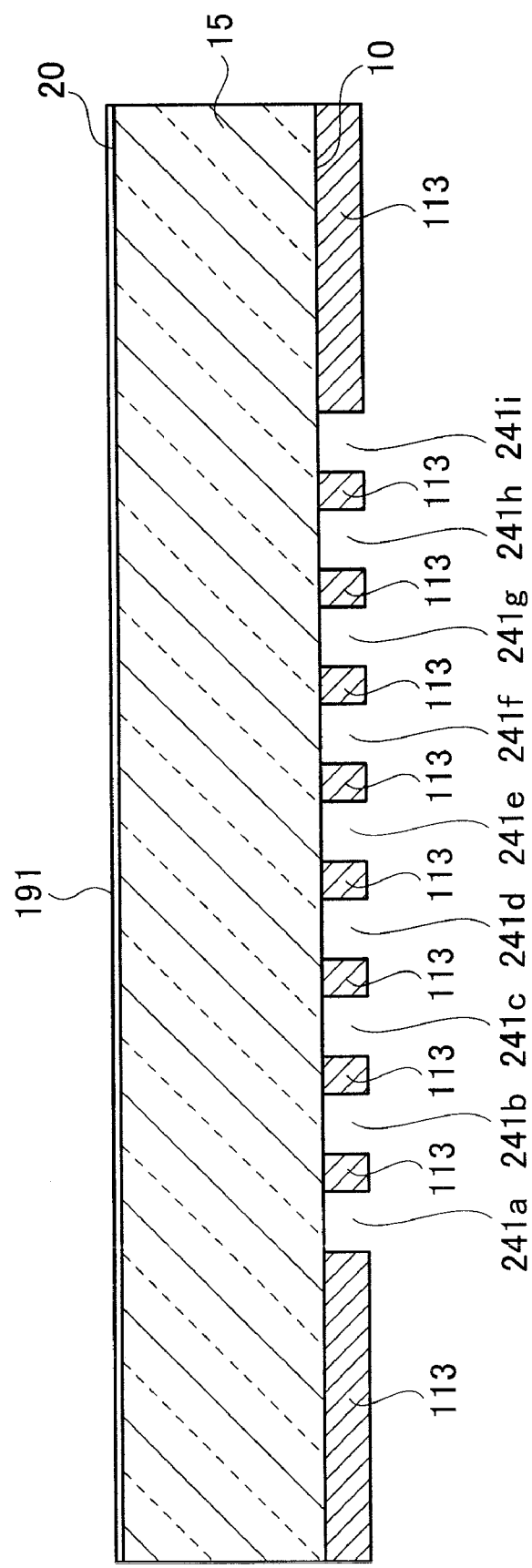
FIG. 49 shows a third sectional view of the biochip according to the fifth embodiment of the present invention.

It should be noted that the shape of the biochip according to the fifth embodiment is not limited to FIG. 45. For example, as shown in FIG. 48, wells 61a, 61b, 61c, 61d, 61e, 61f, 61g, 61h, 61i may be delineated in the base plate 15, and the plurality of biomaterial films 91a-99i may be disposed on the bottoms of the wells 61a-61i, respectively. Alternatively, a biomaterial film 191 may be disposed on the second surface 20, as shown in FIG. 49. When the illuminating light is emitted from the first surface 10 of the base plate 15, the light shielding film 113 restricts regions where the illuminating light penetrates. Therefore, even if the biomaterial film 191 are evenly disposed on the second surface 20, the contrast between presence and absence of chromogenic reaction becomes clear.

(SIXTH EMBODIMENT)

Figure 50:
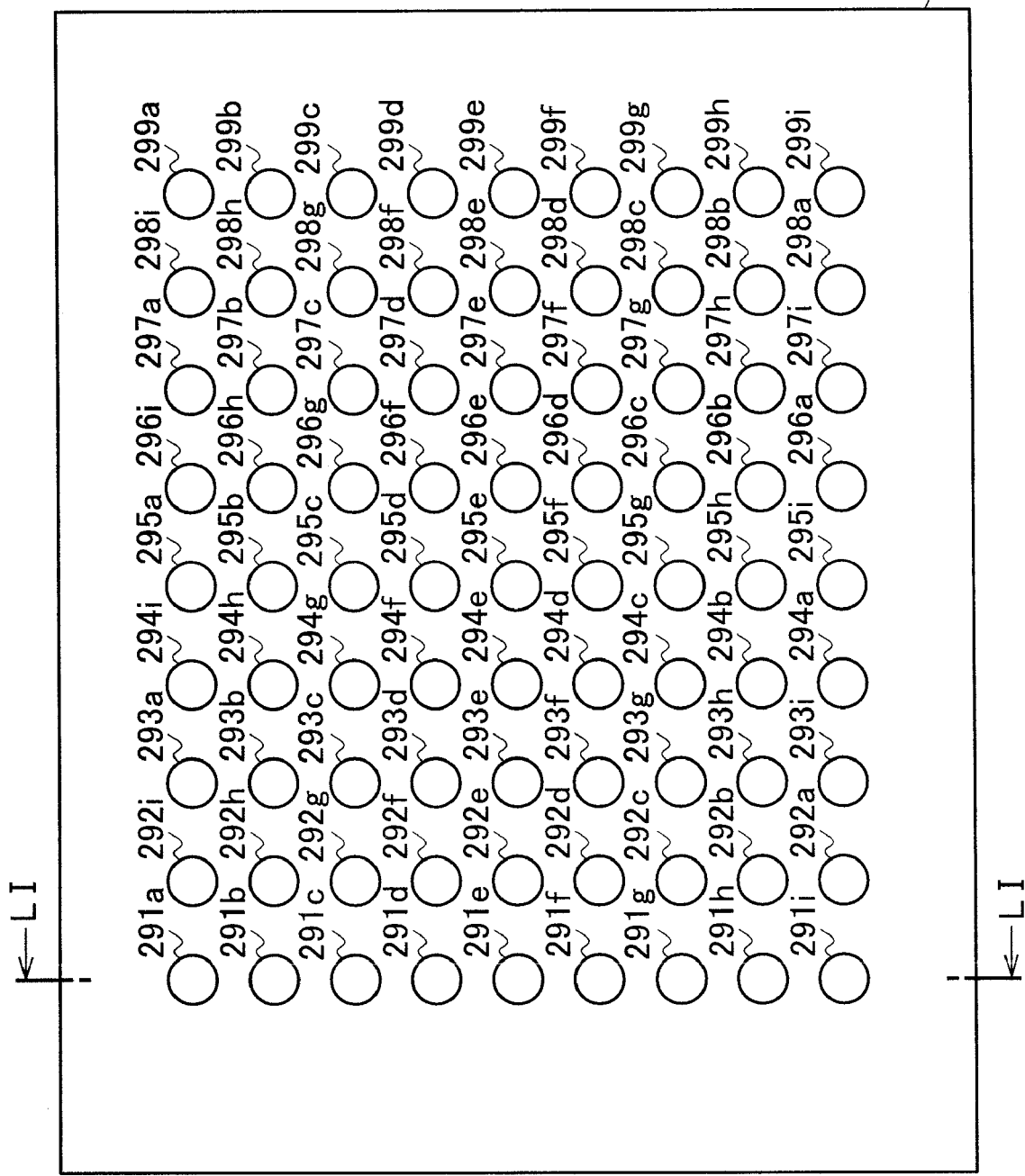
FIG. 50 shows a top view of the biochip according to a sixth embodiment of the present invention.
Figure 51:
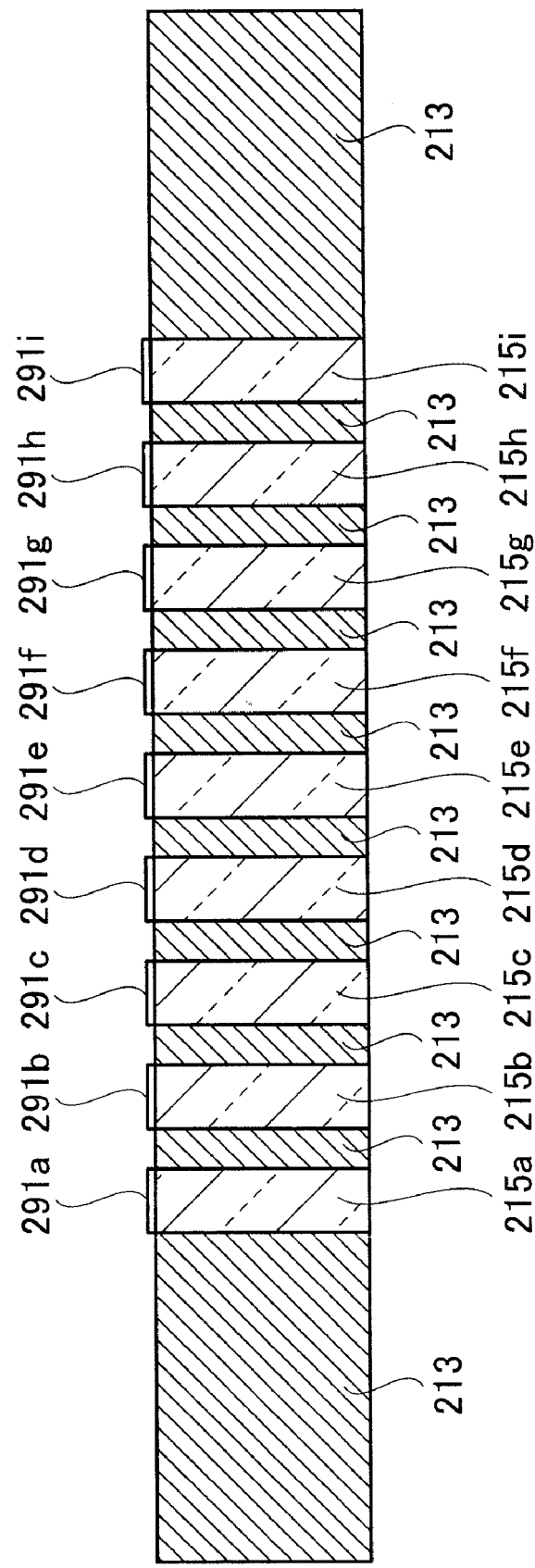
FIG. 51 shows a first sectional view of the biochip according to the sixth embodiment of the present invention.

With reference to FIG. 50 and FIG. 51 that is a sectional view taken on line LI-LI, a biochip according to a sixth embodiment includes a plurality of optical transparency base members 215a, 215b, 215c, 215d, 215e, 215f, 215g, 215h, 215i, a plurality of biomaterial films 291a, 291b, 291c, 291d, 291e, 291f, 291g, 291h, 291i having a plurality of probe biomolecules bonded to the plurality of base members 215a-215i, respectively, and a light shielding member 213 disposed around each of the base members 215a-215i. $SiO_2$ can be used as a material of each of the plurality of base members 215a-215i, for example. The metals and the resins can be used as a material of the light shielding member 213, for example. Also, the base members are disposed on the bottoms of the plurality of biomaterial films 292a, 292b, 292c, 292d, 292e, 292f, 292g, 292h, 292i, 293a, 293b, 293c, 293d, 293e, 293f, 293g, 293h, 293i, 294a, 294b, 294c, 294d, 294e, 294f, 294g, 294h, 294i, 295a, 295b, 295c, 295d, 295e, 295f, 295g, 295h, 295i, 296a, 296b, 296c, 296d, 296e, 296f, 296g, 296h, 296i, 297a, 297b, 297c, 297d, 297e, 297f, 297g, 297h, 297i, 298a, 298b, 298c, 298d, 298e, 298f, 298g, 298h, 298i, 299a, 299b, 299c, 299d, 299e, 299f, 299g, 299h, 299i, shown in FIG. 50, respectively. Each enlarged sectional view of the plurality of biomaterial films 291a-299i is similar to the enlarged sectional view of the biomaterial film 91a shown in FIG. 9. So, an explanation is omitted. As a matter of course, the plurality of probe biomolecules may be bonded to the plurality of base members 215a-215i via the silane coupling agents or the cross coupling agents, respectively, as shown in FIG. 11 and FIG. 12, for example. After the specimen solution including the biotin labeled target biomolecules is dropped onto each of the plurality of biomaterial films 291a-299i shown in FIG. 50 and FIG. 51, the solution including HRP labeled streptavidin is dropped onto each of the plurality of biomaterial films 291a-291i. After it is stilly left and washed, the solution including TMP is dropped into each of the plurality of biomaterial films 291a-291i. In the case where the target biomolecules are trapped in each of the plurality of biomaterial films 291a-291i, the colors of TMB come out by the HRP of the target biomolecule. Therefore, when the illuminating light is emitted from the side where the plurality of biomaterial films 291a-299i are not disposed, it is possible to easily confirm the presence or absence of the chromogenic reaction, because of the contrast between the transmitted light of the illuminating light incident on each of the plurality of base members 215a-215i and the light shielding member 213.

Figure 52:
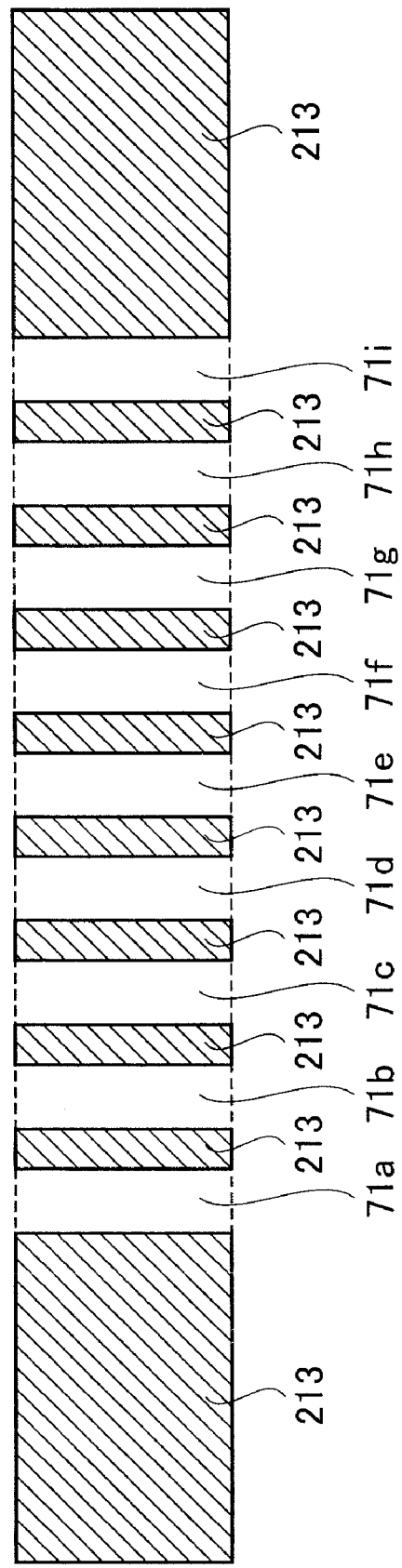
FIG. 52 shows a first sectional process drawing of the biochip according to the sixth embodiment of the present invention.
Figure 53:
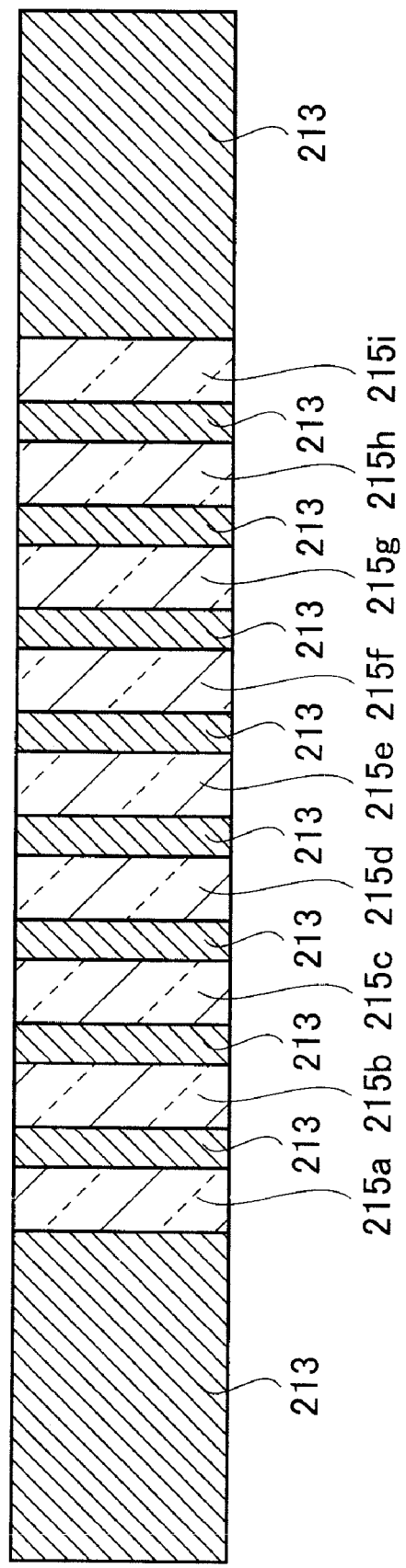
FIG. 53 shows a second sectional process drawing of the biochip according to the sixth embodiment of the present invention.
Figure 54:
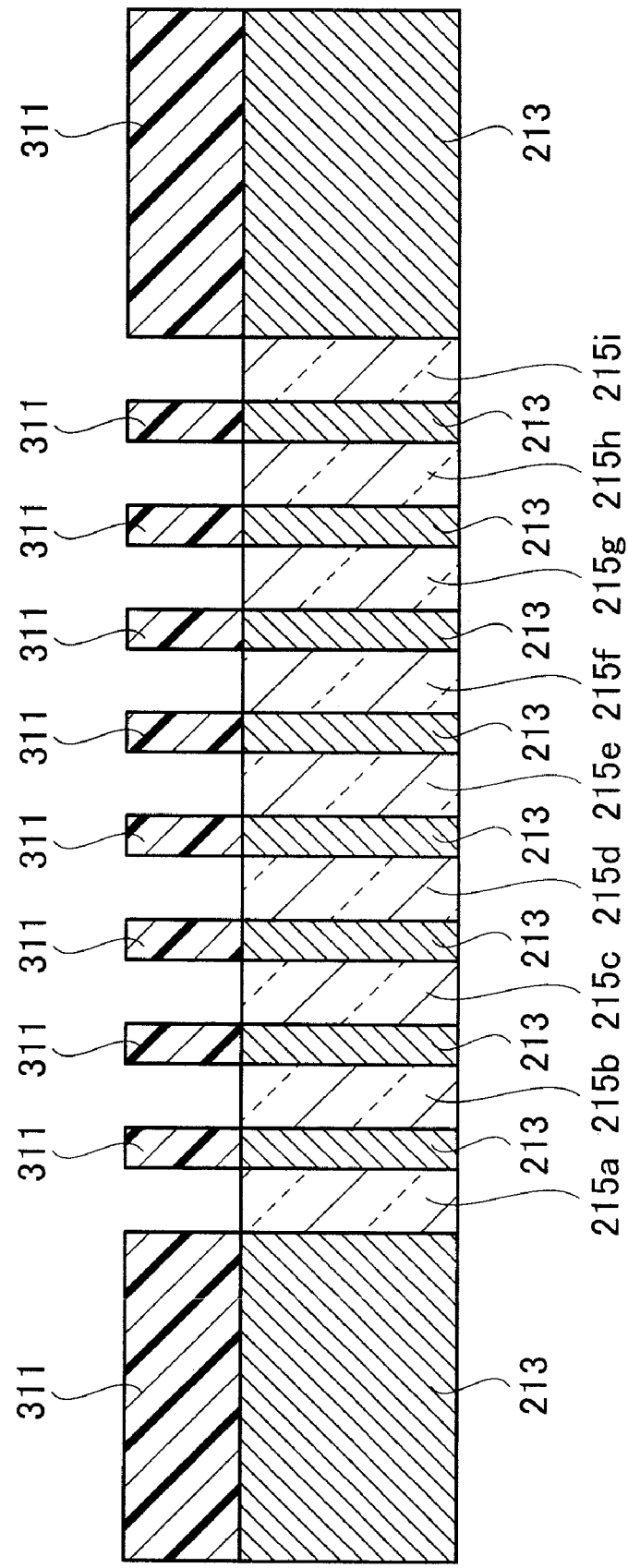
FIG. 54 shows a third sectional process drawing of the biochip according to the sixth embodiment of the present invention.
Figure 55:
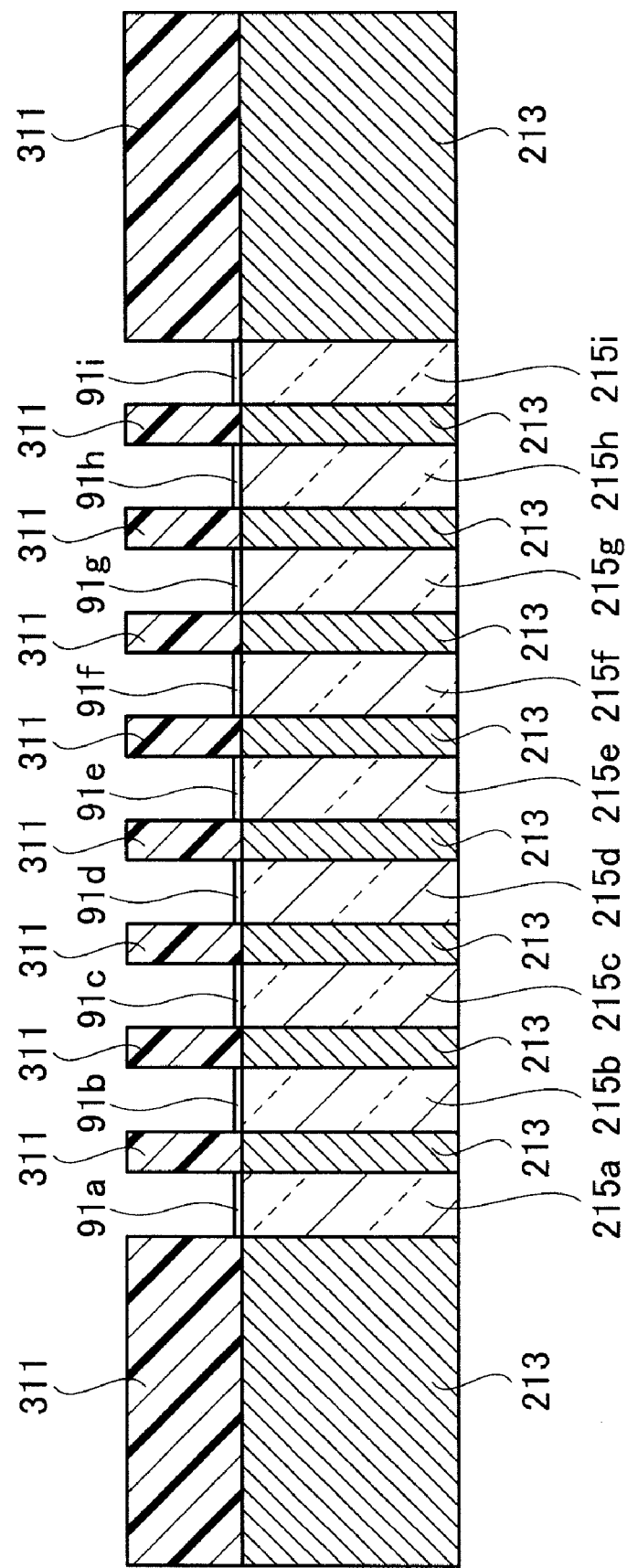
FIG. 55 shows a fourth sectional process drawing of the biochip according to the sixth embodiment of the present invention.

Next, a method for manufacturing the biochip according to the sixth embodiment is described. First, as shown in FIG. 52, the light shielding member 213 having the plurality of through holes 71a, 71b, 71c, 71d, 71e, 71f, 71g, 71h, 71i is prepared. In FIG. 53, the plurality of base members 215a-215i are inserted into the plurality of through holes 71a-71i, respectively. In FIG. 54, the polymer membrane 311 having the plurality of openings exposing the plurality of base members 215a-215i is formed on the light shielding member 213, by the lithography method. In FIG. 55, the plurality of biomaterial films 91a-91i are formed on the plurality of base members 215a-215i, respectively. Thereafter, the polymer membrane 311 is removed and the biochip according to the sixth embodiment is achieved.

Figure 56:
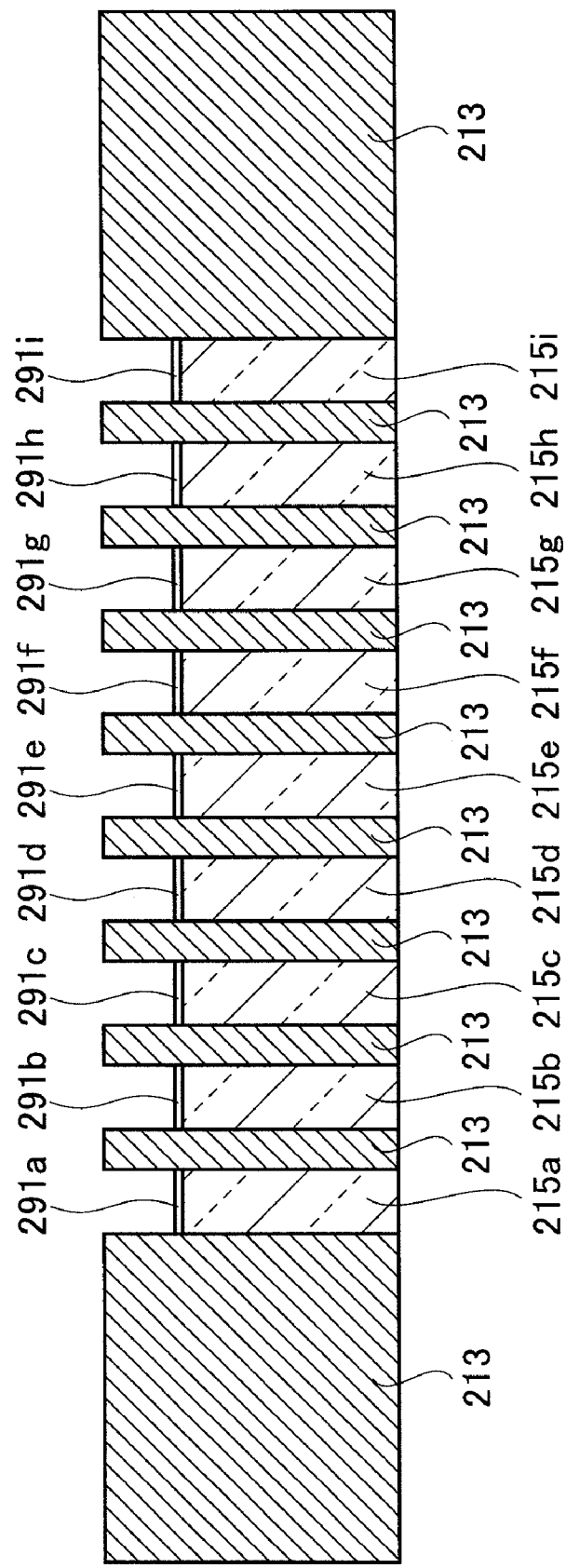
FIG. 56 shows a second sectional view of the biochip according to the sixth embodiment of the present invention.

It should be noted that the shape of the biochip according to the sixth embodiment is not limited to FIG. 51. For example, as shown in FIG. 56, each thickness of the plurality of base members 215a-215i may be different from the thickness of the light shielding member 213. By setting the thickness of the light shielding member 213 thicker than each thickness of the plurality of base members 215a-215i, a plurality of wells of which side walls are the light shielding member 213 and bottoms are the surfaces of the plurality of base members 215a-215i, respectively, are provided. The biomaterial films 291a, 291b, 291c, 291d, 291e, 291f, 291g, 291h, 291i may be disposed on the bottoms of the plurality of wells, respectively.

(OTHER EMBODIMENT)

Figure 57:
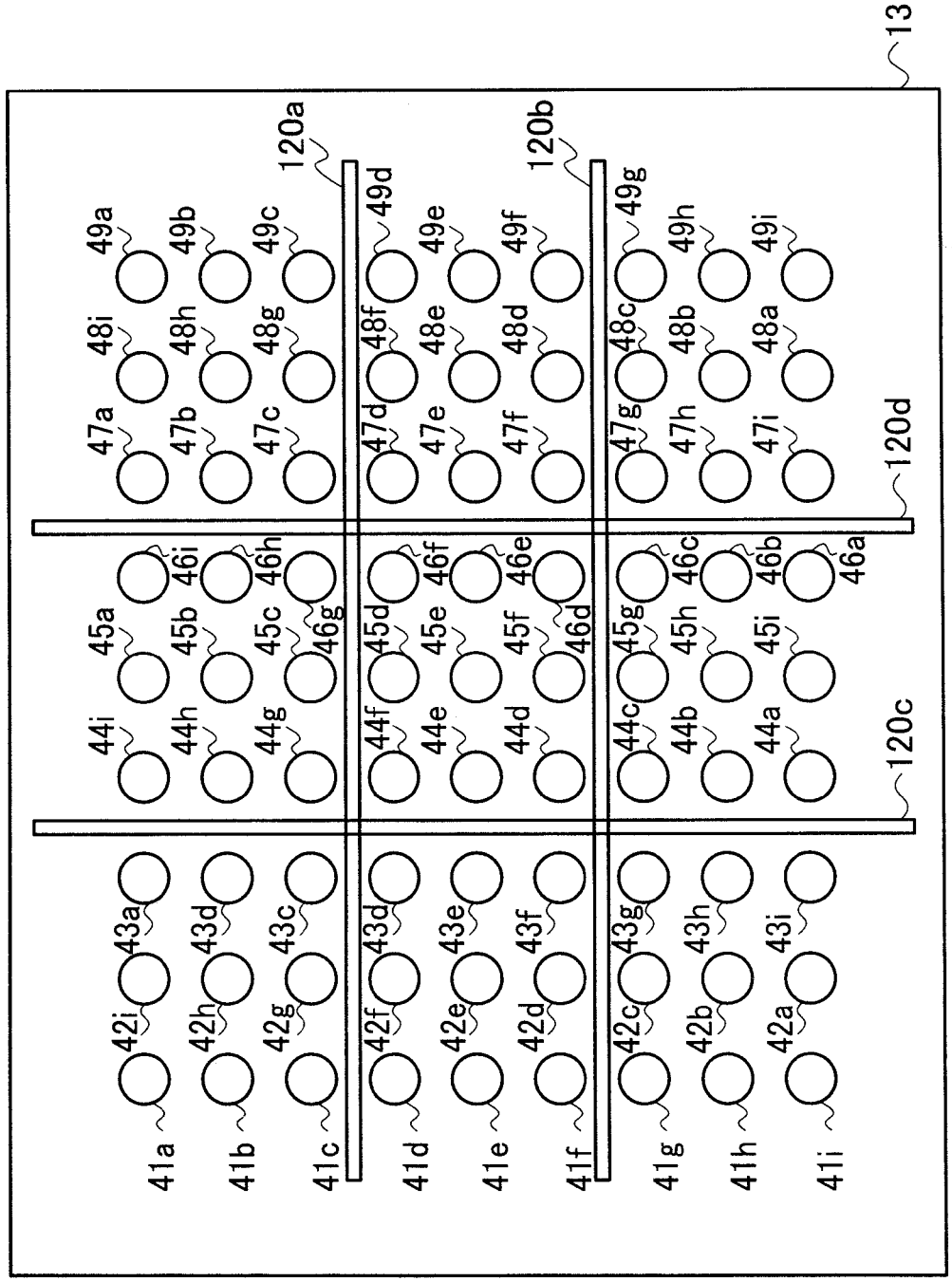
FIG. 57 shows a top view of the biochip according to other embodiment of the present invention.

Although the invention has been described above by reference to the embodiment of the present invention, the present invention is not limited to the embodiment described above. Modifications and variations of the embodiment described above will occur to those skilled in the art, in the light of the above teachings. For example, as shown in FIG. 57, by delineating grooves 120*a*, 120*b*, 120*c*, 120*d* between the plurality of wells 41*a*-41*i*, 42*a*-42*i*, 43*a*-43*i*, 44*a*-44*i*, 45*a*-45*i*, 46*a*-46*i*, 47*a*-47*i*, 48*a*-48*i*, 49*a*-49*i* in the metallic membrane 13, it becomes easy to determine the locations where the plurality of wells 41*a*-41*i*, 42*a*-42*i*, 43*a*-43*i*, 44*a*-44*i*, 45*a*-45*i*, 46*a*-46*i*, 47*a*-47*i*, 48*a*-48*i*, 49*a*-49*i* are present, by naked eye. In addition, by delineating the grooves 120*a*-120*d* in the metallic membrane 13, it becomes easy to peel off the polymer membrane 11 from the metallic membrane 13 in the process for manufacturing the biochip. As described above, the present invention includes many variations of embodiments that are not described here. Therefore, the scope of the invention is defined with reference to the following claims that are appropriate from this disclosure.

Industrial Applicability

The substrate for the biochip, the biochip, the method for manufacturing the substrate for the biochip, the method for manufacturing the biochip according to the present invention can be utilized in a healthcare industry, a household industry, and a cosmetic industry, for example.

The invention claimed is:

1. A method for manufacturing a biochip including:
   preparing a base plate;
   forming a metallic membrane on the base plate;
   forming a crosslinkable polymer membrane on the metallic membrane;
   selectively removing portions of the polymer membrane;
   delineating a plurality of wells reaching the base plate in the metallic membrane by using the polymer membrane as an etching mask;
   introducing a plurality of hydroxyl groups on a surface of the base plate exposed from the plurality of wells;
   bonding a plurality of probe biomolecules including protected amino groups to the plurality of hydroxyl groups; and
   soaking the base plate, the metallic membrane and the polymer membrane in an alkaline solution to deprotect the amino groups included in the plurality of probe biomolecules and peel off the polymer membrane from the metallic membrane after the probe biomolecules are introduced on the base plate,
   wherein the crosslinkable polymer membrane protects the metallic membrane while the probe biomolecules are introduced on the plate exposed from the plurality of wells.

2. The method for manufacturing the biochip of claim 1, wherein the base plate is composed of a silicon oxide.

3. The method for manufacturing the biochip of claim 1, wherein the metallic membrane is composed of titanium.

4. The method for manufacturing the biochip of claim 1, wherein the metallic membrane is composed of a transition metallic oxide.

5. The method for manufacturing the biochip of claim 1, wherein the metallic membrane is composed of a transition metal nitride.

6. The method for manufacturing the biochip of claim 1, wherein the metallic membrane is composed of a transition metal carbide.

7. The method for manufacturing the biochip of claim 1, wherein the polymer membrane is composed of an epoxy resin.

8. The method for manufacturing the biochip of claim 1, wherein the step for peeling off the polymer membrane from the metallic membrane includes a step for blowing the polymer membrane with an air.

9. A method for manufacturing a biochip including:
   preparing a substrate for the biochip comprising a base plate, a metallic membrane disposed on the base plate and having a plurality of wells reaching the base plate, a crosslinkable polymer membrane disposed on the metallic membrane, and a plurality of hydroxyl groups introduced on a surface of the base plate exposed from the plurality of wells;
   bonding a plurality of probe biomolecules including protected amino groups to the plurality of hydroxyl groups; and
   soaking the base plate, the metallic membrane and the polymer membrane in an alkaline solution to deprotect amino groups included in the plurality of probe biomolecules and peel off the polymer membrane from the metallic membrane after the probe biomolecules are introduced on the base plate,
   wherein the crosslinkable polymer membrane protects the metallic membrane while the probe biomolecules are introduced on the plate exposed from the plurality of wells.

10. The method for manufacturing the biochip of claim 9, wherein the metallic membrane is composed of titanium.

11. The method for manufacturing the biochip of claim 9, wherein the metallic membrane is composed of a transition metallic oxide.

12. The method for manufacturing the biochip of claim 9, wherein the metallic membrane is composed of a transition metal nitride.

13. The method for manufacturing the biochip of claim 9, wherein the metallic membrane is composed of transition metal carbide.

14. The method for manufacturing the biochip of claim 9, wherein the polymer membrane is composed of an epoxy resin.

* * * * *